US011215608B2

(12) United States Patent
Letai

(10) Patent No.: US 11,215,608 B2
(45) Date of Patent: *Jan. 4, 2022

(54) METHODS OF DETERMINING CELLULAR CHEMOSENSITIVITY

(71) Applicant: Dana-Farber Cancer Institute, Inc., Boston, MA (US)

(72) Inventor: Anthony Letai, Medfield, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/335,238

(22) Filed: Oct. 26, 2016

(65) Prior Publication Data

US 2017/0184567 A1 Jun. 29, 2017

Related U.S. Application Data

(63) Continuation of application No. 13/478,831, filed on May 23, 2012, now Pat. No. 9,540,674, which is a continuation of application No. 11/695,321, filed on Apr. 2, 2007, now Pat. No. 8,221,966.

(60) Provisional application No. 60/788,138, filed on Mar. 31, 2006.

(51) Int. Cl.
C12Q 1/25 (2006.01)
G01N 33/50 (2006.01)
G01N 33/574 (2006.01)
C12Q 1/02 (2006.01)
C12N 15/10 (2006.01)
G01N 33/52 (2006.01)

(52) U.S. Cl.
CPC ..... *G01N 33/5011* (2013.01); *C12N 15/1037* (2013.01); *C12Q 1/025* (2013.01); *G01N 33/521* (2013.01); *G01N 33/574* (2013.01); *G01N 33/5748* (2013.01); *G01N 2510/00* (2013.01); *G01N 2800/52* (2013.01)

(58) Field of Classification Search
CPC .................................................. G01N 33/5011
USPC .......................................................... 435/4
See application file for complete search history.

(56) References Cited

U.S. PATENT DOCUMENTS

| | | | |
|---|---|---|---|
| 4,522,811 A | 6/1985 | Eppstein et al. |
| 4,676,980 A | 6/1987 | Segal et al. |
| 4,816,567 A | 3/1989 | Cabilly et al. |
| 4,946,778 A | 8/1990 | Ladner et al. |
| 5,225,539 A | 7/1993 | Winter |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,674,980 A | 10/1997 | Frankel et al. |
| 5,804,604 A | 9/1998 | Frankel et al. |
| 5,916,771 A | 6/1999 | Hori et al. |
| 5,939,598 A | 8/1999 | Kucherlapati et al. |
| 5,965,703 A | 10/1999 | Horne et al. |
| 7,064,193 B1 | 6/2006 | Cory et al. |
| 7,714,005 B2 | 5/2010 | Chen et al. |
| 7,868,133 B2 | 1/2011 | Korsmeyer et al. |
| 8,221,966 B2 | 7/2012 | Letai |
| 8,466,140 B2 | 6/2013 | Altieri et al. |
| 9,360,473 B2 | 6/2016 | Cardone |
| 9,540,674 B2 | 1/2017 | Letai |
| 9,856,303 B2 | 1/2018 | Korsmeyer et al. |
| 9,902,759 B2 | 2/2018 | Korsmeyer et al. |
| 10,393,733 B2 | 8/2019 | Letai et al. |
| 10,739,333 B2 | 8/2020 | Ryan et al. |
| 10,761,086 B2 | 9/2020 | Letai et al. |
| 2002/0115613 A1 | 8/2002 | Kumar |
| 2004/0171809 A1 | 9/2004 | Korsmeyer et al. |
| 2007/0027175 A1 | 2/2007 | Shaughnessy et al. |
| 2008/0199890 A1 | 8/2008 | Letai |
| 2008/0234201 A1 | 9/2008 | Korsmeyer et al. |
| 2010/0286057 A1 | 11/2010 | Walensky et al. |
| 2011/0130309 A1 | 6/2011 | Cardone |
| 2011/0154522 A1 | 6/2011 | Korsmeyer et al. |
| 2013/0122492 A1 | 5/2013 | Khosravi et al. |
| 2013/0149718 A1 | 6/2013 | Letai |
| 2015/0362479 A1 | 12/2015 | Letai et al. |
| 2016/0178612 A1 | 6/2016 | Cardone |
| 2016/0200786 A1 | 7/2016 | Korsmeyer et al. |
| 2016/0231314 A1 | 8/2016 | Ryan et al. |
| 2016/0258933 A1 | 9/2016 | Letai |
| 2017/0160267 A9 | 6/2017 | Letai |
| 2018/0120297 A1 | 5/2018 | Letai et al. |
| 2018/0128813 A1 | 5/2018 | Bhola et al. |
| 2018/0244740 A1 | 8/2018 | Korsmeyer et al. |
| 2020/0096499 A1 | 3/2020 | Letai et al. |

FOREIGN PATENT DOCUMENTS

| | | |
|---|---|---|
| JP | H10-510059 A | 9/1998 |
| JP | 2005-130867 | 5/2005 |
| JP | 2005-518393 A | 6/2005 |

(Continued)

OTHER PUBLICATIONS

Hermine et al (Blood, 1996, 87(1): 265-272.*
Schmitt et al (Nature Medicine, 2000, 6(8): 1029-1035).*
U.S. Appl. No. 15/568,994, filed Oct. 24, 2017, Pending.
U.S. Appl. No. 15/569,851, filed Oct. 27, 2017, Pending.
EP14845952.2, Mar. 27, 2017, Extended European Search Report.
PCT/US2016/029495, Oct. 31, 2017, International Preliminary Report on Patentability.
PCT/US2016/029510, Oct. 31, 2017, International Preliminary Report on Patentability.
Extended European Search Report for EP14845952.2 dated Mar. 27, 2017.

(Continued)

Primary Examiner — Sean E Aeder
(74) Attorney, Agent, or Firm — Wolf, Greenfield & Sacks, P.C.

(57) ABSTRACT

The present invention provides methods of determining cell sensitivity to a therapeutic agent.

12 Claims, 36 Drawing Sheets
Specification includes a Sequence Listing.

(56) References Cited

FOREIGN PATENT DOCUMENTS

| | | |
|---|---|---|
| JP | 2006-520606 | 9/2006 |
| JP | 2009-532033 A | 9/2009 |
| JP | 2009-240173 | 10/2009 |
| JP | 2009-542195 A | 12/2009 |
| JP | 2009-543044 | 12/2009 |
| JP | 2011-501731 | 1/2011 |
| JP | 2012-529890 | 11/2012 |
| JP | 2014-81365 | 5/2014 |
| JP | 6663852 | 3/2020 |
| WO | WO 91/00360 A1 | 1/1991 |
| WO | WO 92/20373 A1 | 11/1992 |
| WO | WO 93/08829 A1 | 5/1993 |
| WO | WO 94/02602 A1 | 2/1994 |
| WO | WO 94/11026 A2 | 5/1994 |
| WO | WO 96/27011 A1 | 9/1996 |
| WO | WO 96/33735 A1 | 10/1996 |
| WO | WO 96/34096 A1 | 10/1996 |
| WO | WO 97/05265 A1 | 2/1997 |
| WO | WO 99/53049 A1 | 10/1999 |
| WO | WO 00/59526 A1 | 10/2000 |
| WO | WO 01/12661 A2 | 2/2001 |
| WO | WO 02/20568 A2 | 3/2002 |
| WO | WO 03/040168 A2 | 5/2003 |
| WO | WO 2004/022580 A2 | 3/2004 |
| WO | WO 2004/058804 A1 | 7/2004 |
| WO | WO 2005/044839 A2 | 5/2005 |
| WO | WO 2006/099667 A1 | 9/2006 |
| WO | WO 2007/123791 A2 | 11/2007 |
| WO | WO 2007/149270 A2 | 12/2007 |
| WO | WO 2008/021484 A2 | 2/2008 |
| WO | WO 2010/147961 A1 | 12/2010 |
| WO | WO 2013/170176 A2 | 11/2013 |
| WO | WO 2013/188978 A1 | 12/2013 |
| WO | WO 2014/047342 A1 | 3/2014 |
| WO | WO 2015/010094 A1 | 1/2015 |
| WO | WO 2015/042249 A1 | 3/2015 |
| WO | WO 2016/176288 A1 | 11/2016 |
| WO | WO 2016/176299 A1 | 11/2016 |

OTHER PUBLICATIONS

International Preliminary Report on Patentability for PCT/US2016/0295495 dated Nov. 9, 2017.
International Preliminary Report on Patentability for PCT/US2016/029510 dated Nov. 9, 2017.
Quinsay et al., Pro-Apoptotic Bnip3 Mediates Permeabilization of Mitochondria and Release of Cytocrome c via a Novel Mechanism. Circulation. Oct. 28, 2008;118(18):S388. Abstract.
Soltow et al., Overexpression of CuZnSOD or MnSOD protects satellite cells from doxorubicin-induced apoptosis. FASEB Journal. Apr. 2007;21:A449. Abstract.
Sugiyama et al., Activation of mitochondrial voltage-dependent anion channel by apro-apoptotic BH3-only protein Bim. Oncogene. Jul. 25, 2002;21(32):4944-56.
U.S. Appl. No. 10/658,028, filed Sep. 9, 2003, Abandoned, 2004-0171809.
U.S. Appl. No. 11/789,557, filed Apr. 24, 2007, Granted, U.S. Pat. No. 7,868,133.
U.S. Appl. No. 12/966,821, filed Dec. 13, 2010, Published, 2011-0154522.
U.S. Appl. No. 15/073,356, filed Mar. 17, 2016, Published, 2016-0200786.
U.S. Appl. No. 11/695,321, filed Apr. 2, 2007, Granted, U.S. Pat. No. 8,221,966.
U.S. Appl. No. 13/478,831, filed May 23, 2012, Granted, U.S. Pat. No. 9,540,674.
U.S. Appl. No. 15/073,391, filed Mar. 17, 2016, Published, 2016-0258933.
U.S. Appl. No. 14/429,272, filed Mar. 18, 2015, Published, 2015-0362479.
U.S. Appl. No. 15/022,987, filed Mar. 18, 2016, Published, 2016-0231314.
EP03749602.3, Jun. 7, 2006, Supplementary Partial European Search Report.
EP03749602.3, Sep. 28, 2006, Supplementary Partial European Search Report.
PCT/US2003/028482, Dec. 8, 2005, International Search Report.
PCT/US2007/008055, Jan. 2, 2008, International Search Report and Written Opinion.
PCT/US2007/008055, Sep. 30, 2008, International Preliminary Report on Patentability.
PCT/US2013/060707, Jan. 9, 2014, International Search Report and Written Opinion.
PCT/US2013/060707, Apr. 2, 2015, International Preliminary Report on Patentability.
PCT/US2014/056284, Dec. 31, 2014, International Search Report and Written Opinion.
PCT/US2014/056284, Mar. 31, 2016, International Preliminary Report on Patentability.
PCT/US2016/029495, Aug. 5, 2016, International Search Report and Written Opinion.
PCT/US2016/029510, Aug. 12, 2016, International Search Report and Written Opinion.
Supplementary Partial European Search Report for EP03749602.3 dated Jun. 7, 2006.
Supplementary Partial European Search Report for EP03749602.3 dated Sep. 28, 2006.
International Search Report for PCT/US2003/028482 dated Dec. 8, 2005.
International Search Report and Written Opinion for PCT/US2007/008055 dated Jan. 2, 2008.
International Preliminary Report on Patentability for PCT/U2007/008055 dated Sep. 30, 2008.
International Search Report and Written Opinion for PCT/US2013/060707 dated Jan. 9, 2014.
International Preliminary Report on Patentability for PCT/US2013/060707 dated Apr. 2, 2015.
International Search Report and Written Opinion for PCT/US2014/056284 dated Dec. 31, 2014.
International Preliminary Report on Patentability for PCT/US2014/056284 dated Mar. 31, 2016.
International Search Report and Written Opinion for PCT/US2016/029495 dated Aug. 5, 2016.
International Search Report and Written Opinion for PCT/US2016/029510 dated Aug. 12, 2016.
Adams, et al., The Bcl-2 Protein Family: Arbiters of Cell Survival. Science. 1998;281(5381):1322-1326.
Ait-IkhleF et al. The motoneuron degeneration in the wobbler mouse is independent of the overexpression of a Bcl2 transgene in neurons. Neurosci. Lett. 1995;199:163-6.
Bae et al., Underphosphorylated BAD interacts with diverse antiapoptotic Bcl-2 family proteins to regulate apoptosis. Apoptosis. 2001;6:319-30.
Bouillet et al., Proapoptotic Bcl-2 Relative Bim Required for Certain Apoptotic Responses, Leukocyte Homeostatis, and to Preclude Autoimmunity. Science. 1999;286:1735-8.
Boyd et al., Bik, a novel death-inducing protein shares a distinct sequence motif with Bcl-2 family proteins and interacts with viral and cellular survival-promoting proteins. Oncogene. 1995;11:1921-8.
Brady et al., Reflections on a peptide. Nature. 1994;368:692-3.
Brennan et al., Preparation of Bispecific Antibodies by Chemical Recombination of Monoclonal Immunoglobulin $G_1$ Fragments. Science. 1985;229:81.
Buron et al., Use of human cancer cell lines mitochondria to explore the mechanisms of BH3 peptides and ABT-737-induced mitochondrial membrane permeabilization. PLoS One. Mar. 31, 2010;5(3):e9924. doi:10.1371/journal.pone.0009924.
Calin et al., A MicroRNA Signature Associated with Prognosis and Progression in Chronic Lymphocytic Leukemia. N. Engl. J. Med. 2005;353:1793-801.
Caron et al., Engineered Humanized Dimeric Forms of IgG Are More Effective Antibiotics. J. Exp. Med. 1992;176:1191-5.

(56) References Cited

OTHER PUBLICATIONS

Cartron et al., The first α Helix of Bax Play a Necessary Role in Its Ligand-Induced Activation by the BH3-Only Proteins Bid and PUMA. Mol. Cell 2004;16:807-18.
Certo et al., Mitochondria Primed by Death Signals Determine Cellular Addiction to Antiapoptotic BCL-2 Family Members. Cancer Cell. May 2006;9:351-65.
Chen et al., Caspase cleavage of BIM$_{EL}$ triggers a positive feedback amplification of apoptotic signaling. Proc. Natl. Acad. Sci. USA. 2004;101(5):1235-40.
Chen et al., Differential Targeting of Prosurvival Bcl-2 Proteins by Their BH3-Only Ligands Allows Complementary Apoptotic Function. Mol. Cell. 2005;17:393-403.
Cheng et al., Bax-independent inhibition of apoptosis by Bcl-X$_L$. Nature. 1996;379:554-6.
Cheng et al., BCL-2, BCL-X$_L$ Sequester BH3 Domain-Only Molecules Preventing BAX- and BAK-Mediated Mitochondrial Apoptosis. Mol. Cell. 2001;8:705-11.
Chipuk et al., Direct Activation of Bax by p53 Mediates Mitochondrial Membrane Permeabilization and Apoptosis. Science. 2004;303:1010-4.
Chittenden et al., A conserved domain in Bak, distinct form BH1 and BH2, mediates cell death and protein binding functions. EMBO J. 1995;14(22):5589-96.
Chittenden et al., Induction of apoptosis by the Bcl-2 homologue Bak. Nature. 1995;374(6524):733-6.
Chonghaile et al., Pretreatment mitochondrial priming correlates with clinical response to cytotoxic chemotherapy. Science. Nov. 25, 2011;334(6059):1129-33. doi: 10.1126/science.1206727. Epub Oct. 27, 2011.
Cole et al., The EBV-Hybridoma technique and its application to human lung cancer. Monoclonal Antibodies and Cancer Therapy. 1985:77-96.
Cory et al., The Bcl2 Family: Regulators of the Cellular Life-Or-Death Switch. Nat. Rev. Cancer. 2002;2(9):647-56.
Cosulich et al., Regulation of apoptosis by BH3 domains in a cell-free system. Curr. Biol. 1997;7(12):913-20.
Cote et al., Generation of human monoclonal antibiotics reactive with cellular antigens. Proc. Natl. Acad. Sci. USA. 1983;80:2026-30.
Czabotar et al., Bax Activation by Bim? Cell Death and Differentiation. Sep. 2009;16:1187-91.
Davids et al., BH3 profiling demonstrates that restoration of apoptotic priming contributes to increased sensitivity to PI3K inhibition in stroma-exposed chronic lymphocytic leukemia cells. Blood 118(21). Nov. 18, 2011. Abstract.
Davids et al., Targeting the B-cell lymphoma/leukemia 2 family in cancer. J Clin Oncol. Sep. 1, 2012;30(25):3127-35. doi: 10.1200/JCO.2011.37.0981. Epub May 29, 2012.
Degrado, Designs of peptides and proteins. Adv Protein Chem. 1988;39:51-124.
Deng et al., BH3 Profiling Identifies Three Distinct Classes of Apoptotic Blocks to Predict Response to ABT-737 and Conventional Chemotherapeutic Agents. Cancer Cell. Aug. 2007;12:171-85.
Derenne et al., Antisense strategy shows that Mcl-1 rather than Bcl-2 or Bcl-xL is an essential survival protein of human myeloma cells. Blood. 2002;100:194-9.
Desagher et al., Bid-induced Conformational Change of Bax Is Responsible for Mitochondrial Cytochrome c Release during Apoptosis. J. Cell Biol. 1999;144(5):891-901.
Di Lisa et al., Mitochondrial Function and Cell Injury in Single Cardiac Myocytes Exposed to Anoxia and Reoxygenation. Transplant Proc. 1995;27(5):2829-30.
Di Lisa et al., Mitochondrial membrane potential in single living adult rat cardiac myocytes exposed to anoxia or metabolic inhibition. J. Physiol. 1995;486(1):1-13.
Dohner et al., Genomic Aberrations and Survival in Chronic Lymphocytic Leukemia. N. Engl. J. Med. 2000;343:1910-16.

Egle et al., Bim is a suppressor of Myc-induced mouse B cell leukemia. Proc. Natl. Acad. Sci. USA. 2004;101(16):6164-9.
Ellerby, et al., Anti-cancer activity of targeted pro-apoptotic peptides. Nat. Med. 1999;5(9):1032-8.
Elliott et al., Intercellular Trafficking and Protein Delivery by a Herpesvirus Structural Protein. Cell. 1997;88:223-33.
Eskes et al., Bid Induces the Oligomerization and Insertion of Bax into the Outer Mitochondrial Membrane. Mol. Cell. Biol. 2000;20(3):929-35.
Fanidi et al., Cooperative interaction between c-myc and -2 proto-oncogenes. Nature. 1992;359:554-6.
Fishwild et al., High-avidity human IgGk monoclonal antibodies from a novel strain of minilocus transgenic mice. Nature Biotechnology. 1996;14:845-51.
Frankel et al., Activity of synthetic peptides from the Tat protein of human immunodeficiency virus type 1. Proc. Natl. Acad. Sci. USA. 1989;86:7397-401.
Fuchs et al., Pathway for Polyarginine Entry into Mammalian Cells. Biochemistry Mar. 2004;43(9):2438-44.
Futaki et al., Arginine-rich Peptides: An Abundant Source of Membrane-Permeable Peptides Having Potential as Carriers for Intracellular Protein Delivery. J. Biol. Chem. 2001;276(8):5836-40.
Green et al., A matter of life and death. Cancer Cell. 2002;1:19-30.
Green et al., The Pathophysiology of Mitochondrial Cell Death. Science. 2004;305:626-9.
Green, Life, Death, BH3 Profiles, and the Salmon Mousse. Cancer Cell. Aug. 2007;12:97-9.
Griffiths et al., Cell Damage-induced Conformational Changes of the Pro-Apoptotic Protein Bak In Vivo Precede the Onset of Apoptosis. J. Cell Biol. 1999;144(5):903-14.
Gross et al., Enforced dimerization of BAX results in its translocation, mitochondrial dysfunction and apoptosis. EMBO J. 1998;17(14):3878-85.
Grosschedl et al., Introduction of a μ immunoglobulin gene into the mouse germ line: specific expression in lymphoid cells and synthesis of functional antibody. Cell. 1984;38:647-58.
Gruber et al., Efficient Tumor Cell Lysis Mediated by a Bispecific Single Chain Antibody Expressed in *Escherichia coli*. J. Immunol. 1994;152:5368-74.
Gul et al., Apoptotic blocks and chemotherapy resistance: strategies to identify Bcl-2 protein signatures. Briefings in Functional Genomics and Proteomics. Jan. 2008;7(1):27-34.
Hanahan et al., Heritable formation of pancreatic β-cell tumors in transgenic mice expressing recombinant insulin/simian virus 40 oncogenes. Nature. 1985;315:115-22.
Hanahan et al., The Hallmarks of Cancer. Cell. 2000;100:57-70.
Hans et al., Beta-carbolines induce apoptosis in cultured cerebellar granule neurons via the mitochondrial pathway. Neuropharmacology. Jan. 2005;48(1):105-17.
Harada et al., Survival factor-induced extracellular signal-regulated kinase phosphorylates BIM, inhibiting its association with BAX and proapoptotic activity. Proc. Natl. Acad. Sci. USA. 2004;101(43):15313-7.
Hemann et al., Evasion of the p53 tumour surveillance network by tumour-derived MYC mutants. Nature. 2005;436:807-11.
Hemann et al., Suppression of tumorigenesis by the p53 target PUMA. Proc. Natl. Acad. Sci. USA. 2004;101(25):9333-8.
Hengartner et al., C. elegans Cell Survival Gene ced-9 Encodes a functional Homolog of the Mammalian Proto-Oncogene bcl-2. Cell. 1994;76:665-76.
Holinger et al., Bak BH3 Peptides Antagonize Bcl-x.sub.L Function and Induce Apoptosis through Cytochrome c-independent Activation of Caspases. J. Biol. Chem. 1999;274(19):13298-304.
Holliger et al., Diabodies: Small bivalent and bispecific antibody fragments. Proc. Natl. Acad. Sci. USA. 1993;90:6444-8.
Hoogenboom et al., By-passing Immunisation, Human Antibodies from Synthetic Repertoires of Germline VH Gene segments rearranged in Vitro. J. Mol. Biol. 1992;227:381-8.
Hopp et al., Prediction of protein antigenic determinants from amino acid sequences. Proc. Natl. Acad. Sci. USA. 1981;78:3824-8.
Hsu et al., Nonionic Detergents Induce Dimerization among Members of the Bcl-2 Family. J. Biol. Chem. 1997;272(21):13829-34.

(56) References Cited

OTHER PUBLICATIONS

Huang et al., BH3-Only Proteins—Essential Initiators of Apoptotic Cell Death. Cell. 2000;103:839-42.
Huse et al., Generation of a large Combinatorial Library of the Immunoglobulin Repertoire in Phage Lambda. Science. 1989;246:1275-81.
Inohara et al., Harakiri, a novel regulator of cell death, encodes a protein that activates apoptosis and interacts selectively with survival-promoting proteins Bcl-2 and Bcl-$X_L$. Embo J. 1997;16(7):1686-94.
Jackson et al., Heat shock induces the release of fibroblast growth factor 1 from NIH 3T3 cells. Proc. Natl. Acad. Sci. USA. 1992;89:10691-5.
Jameson et al., A rationally designed CD4 analogue inhibits experimental allergic encephalomyelitis. Nature. 1994;368:744-6.
Jones et al., Nature, Replacing the complementarily—determining regions in a human antibody with those from a mouse. 1986;321:522-5.
Jonkers et al., Oncogene addiction: Sometimes a temporary slavery. Cancer Cell. 2004;6:535-8.
Kelekar et al., Bad is a BH3 Domain-Containing Protein that Forms an Inactivating Dimer with Bcl-$X_L$. Mol. Cell Biol. 1997;17(12):7040-6.
Kelekar et al., Bcl-2-family proteins: the role of the BH3 domain in apoptosis. Trends Cell Biol. 1998;8:324-30.
Kohler et al., Continuous cultures of fused cells secreting anti-body of predefined specificity. Nature. 1975;256:495-7.
Korsmeyer et al., Pro-apoptotic cascade activates BID, which oligomerizes BAK or BAX into pores that result in the release of cytochrome c. Cell Death Differ. Dec. 2000;7(12):1166-73.
Kostelny et al., Formation of a Bispecific antibody by the Leucine Zippers. J. Immunol. 1992;148(5):1547-53.
Kozbor et al., The production of monoclonal antibodies from human lymphocytes. Immunol Today. 1983;4:72-9.
Kozbor, A human hybrid Myeloma for production of human monoclonal antibodies. J. Immunol. 1984;133:3001-5.
Krieg, Mechanisms and applications of immune stimulatory CpG oligodeoxynucleotides. Biochim Biophys Acta. 1999;1489(1):107-16.
Kuwana et al., BH3 Domains of BH3-Only Proteins Differentially Regulate Bax-Mediated Mitochondrial Membrane Permeabilization Both Directly and Indirectly. Mol. Cell. 2005;17:525-35.
Kuwana et al., Bid, Bax, and Lipids Cooperate to Form Supramolecular Openings in the Outer Mitochondrial Membrane. Cell. 2002;111:331-42.
Kyte et al., A Simple Method for displaying the Hydropathic Character of a protein. J. Mol. Biol. 1982;157:105-42.
La Vieira, et al., Cell permeable BH3-peptides overcome the cytoprotective effect of Bcl-2 and Bcl-$X_L$. Oncogene. 2002;21(13):1963-77.
Leo et al., Characterization of the Antiapoptotic Bcl-2 Family Member Myeloid Cell Leukemia-1 (Mcl-1) and the Stimulation of Its Message by Gonadotropins in the Rat Ovary. Endocrinol. 1999;140(12):5469-77.
Letai et al., Antiapoptotic BcL-2 is required for maintenance of a model leukemia. Cancer Cell. 2004;6:241-9.
Letai et al., Distinct BH3 domains either sensitize or activate mitochondrial apoptosis, serving as prototype cancer therapeutics. Cancer Cell. Sep. 2002;2(3):183-92.
Letai, BH3 domains as BCL-2 inhibitors: prototype cancer therapeutics. Expert Opin Biol Ther. Apr. 2003;3(2):293-304.
Letai, The BCL-2 network: Mechanistic insights and therapeutic potential. Drug Disc.Today: Disease Mechanisms. 2005;2(2):145-51.
Li et al., Cleavage of BID by Caspase 8 Mediates the Mitochondrial Damage in the Fas Pathway of Apoptosis. Cell. 1998;94(4):491-501.
Li et al., Endonuclease G is an apoptotic DNase when released from mitochondria. Nature. 2001;412:95-9.
Li et al., tsg 101: A novel tumor susceptibility gene isolated by controlled Homozygous functional knockout of Allelic Loci in Mammalian Cells. Cell. 1996;85:319-29.
Liu et al., Bax conformational change is a crucial step for PUMA-mediated apoptosis in human leukemia. Biochem Biophys Res Commun. 2003;310(3):956-62.
Lonberg et al., Antigen-specific human antibodies from mice comprising four distinct genetic modifications. Nature. 1994;368:856-9.
Lonberg et al., Human Antibodies from Transgenic Mice. Intern Rev Immunol. 1995;13:65-93.
Long et al., Optimization and validation of mitochondria-based functional assay as a useful tool to identify BH3-like molecules selectively targeting anti-apoptotic Bcl-2 proteins. BMC Biotechnol. May 24, 2013;13:45. doi: 10.1186/1472-6750-13-45.
Luo et al., Bid, a Be 12 interacting protein, mediates cytochrome c release from mitochondria in response to activation of cell surface death receptors, Cell. 1998;94(4):481-90.
Lutter et al., The pro-apoptotic Bcl-2 family member tBid localizes to mitochondrial contact sites. BMC Cell Biology. 2001;2:22.
Marani et al., Identification of Novel Isoforms of the BH3 Domain Protein Bim which Directly Activate Bax to Trigger Apoptosis. Mol Cell Biol. 2002;22(11):3577-89.
Marks et al., By-passing Immunization human Antibodies from v-gene libraries displayed on phage. J. Mol. Biol. 1991;222:581.
Marks et al., By-passing immunization: building high affinity human antibodies by chin shuffling. Bio/Technology. 1992;10:779-83.
Martin, Opening the Cellular Poison Cabinet. Science. Dec. 2010;330:1330-1.
Mason et al., The Hypogonadal mouse: reproductive functions restored by gene therapy. Science. 1986;234:1372-8.
Matsushita et al., A high-efficiency protein transduction system demonstrating the role of PKA in long-lasting long-term potentiation. J. Neuroscience. 2001;21(16):6000-7.
Matsuzaki, Why and how are peptide-lipid interactions utilized for self-defense? Biochem. Soc. Transactions. 2001;29:598-601.
McDonnell et al., bcl-2-Immunoglobulin Transgenic Mice Demonstrate Extended B Cell Survival and Follicular Lymphoproliferation. Cell. 1989;57:79-88.
Means et al., Modifications to change properties in Chemical Modification of Protein. 1974. Chapter 3, pp. 35-54, Holden-Day.
Milstein et al., Hybrid hybridomas and their use in immunohistochemistry. Nature. 1983;305:537-9.
Montero et al., Drug-induced death signaling strategy rapidly predicts cancer response to chemotherapy. Cell. Feb. 26, 2015;160(5):977-90. doi:10.1016/j.cell.2015.01.042.
Morrison et al., Success in specification. Nature. 1994;368:812-3.
Muchmore et al., X-ray and NMR structure of human Bcl-x.sub.L, an inhibitor of programmed cell death. Nature. 1996;381:335-41.
Munson et al., LIGAND: A Versatile Computerized Approach for Characterization of Ligand-Binding Systems. Analytical Biochemistry. 1980;107:220-39.
Nakano et al., PUMA, a Novel Proapoptotic Gene, is Induced by p53. Mol. Cell. 2001;7:683-94.
Narita, et al., bax interacts with the permeability transition pore to induce permeability transition and cytochrome c release in isolated mitochondria. Proc. Natl. Acad. Sci. USA. 1998;95:14681-6.
Neuberger et al., Generating high-avidity human Mabs in mice. Nature Biotechnology. 1996;14:826.
O'Brien et al., Phase I and II Multicenter Study of Oblimersen Sodium, a Bcl-2 Antisense Oligonucleotide, in Patients With Advanced Chronic Lymphocytic Leukemia. J. Clin. Oncol. 2005;23(30):7697-702.
O'Connor et al., Bim: a novel member of the Bcl-2 family that promotes apoptosis. Embo J. 1998;17(2):384-95.
Oda et al., Noxa, a BH3-Only Member of the Bcl-2 Family and Candidate Mediator of p53-Induced Apoptosis. Science. 2000;288:1053-8.
Oh et al., Conformational Changes in BID, a Pro-apoptotic BCL-2 Family Member, upon Membrane Binding. J. Biol. Chem. 2005;280(1):753-67.
Oliver et al., Permeabilization of Cell Membranes. C. Oliver and M.C. Jamur (eds.), Immnunocytochemical Methods and Protocols, Methods in Molecular Biology, vol. 588, DOI 10.1007/978-1-59745-

(56) References Cited

OTHER PUBLICATIONS 324-0_9, © Humana Press, a part of Springer Science + Business Media, LLC 1995, 1999, 2010. Chapter 9: 4 pages.
Oltersdorf et al., An inhibitor of Bcl-2 family proteins induces regression of solid tumours. Nature. 2005;435:677-81.
Opferman et al., Development and maintenance of B and T lymphocytes requires antiapoptotic MCL-1. Nature. 2003;426:671-6.
Pinkert et al., An albumin enhancer located 10 kb upstream functions along with its promoter to direct efficient, liver-specific expression in transgenic mice. Genes and Dev. 1987;1:268-276.
Polster et al., BH3 Death Domain Peptide Induces Cell Type-selective Mitochondrial Outer Membrane Permeability. J. Biol. Chem. 2001;276 (41):37887-94.
Presta, Antibody engineering. Curr. Op. Struct. Biol. 1992;2:593-6.
Putcha et al., Induction of BIM, a Proapoptotic Bh3-Only BCL-2 Family Member, Is Critical for Neuronal Apoptosis. Neuron. 2001;29(3):615-28.
Puthalakath et al., Bmf: a Proapoptotic BH3-Only Protein Regulated by Interaction with the Myosin V Actin Motor Complex, Activated by Anoikis. Science. 2001;293:1829-32.
Puthalakath et al., Keeping killers on a tight leash: transcriptional and post-translational control of the pro-apoptotic activity of BH3-only proteins. Cell Death Differ. 2002;9:505-12.
Puthalakath et al., The Proapoptotic Activity of the Bcl-2 Family Member Bim is Regulated by Interaction with the Dynein Motor Complex. Mol. Cell. 1999;3:287-96.
Raff, Social controls on cell survival and cell death. Nature. 1992;356:397-400.
Rassenti et al., ZAP-70 Compared with Immunoglobulin Heavy-Chain Gene Mutation Status as a predictor of Disease Progression in Chronic Lymphocytic Leukemia. N. Engl. J. Med. 2004;351:893-901.
Ray et al., BNIP3 Heterodimerizes with Bcl-2/Bcl-$X_L$ and Induces Cell Death Independent of a Bcl-2 Homology 3 (BH3) Domain at Both Mitochondrial and Nonmitochondrial Sites. J. Biol. Chem. 2000;275(2):1439-48.
Readhead et al., Expression of a myelin basic protein gene in transgenic shiverer mice: correction of the dysmyelinating phenotype. Cell. 1987;48:703-12.
Ren et al., BID, BIM, and PUMA Are Essential for Activation of the BAX- and BAK-Dependent Cell Death Program. Science. Dec. 2010;330:1390-3.
Riechmann et al., Reshaping human antibodies for therapy. Nature. 1988;332:323-7.
Rothbard et al., Conjugation of arginine oligomers to cyclosporine A facilitates topical delivery and inhibition of inflammation. Nature Med. 2000;6(11):1253-7.
Ryan et al., Heightened mitochondrial priming is the basis for apoptotic hypersensitivity of CD4+ CD8+ thymocytes. Proc Natl Acad Sci U S A. Jul. 20, 2010;107(29):12895-900. doi: 10.1073/pnas.0914878107. Epub Jul. 6, 2010.
Samson et al., A 35 amino acid fragment of leptin inhibits feeding in the rat. Endocrinology. 1996;137:5182-5.
Sattler et al., Structure of Bcl-x.sub.L-Bak Peptide Complex: Recognition Between Regulators of Apoptosis. Science. 1997;275:983-6.
Schimmer et al., Cell Death and Differentiation. 2001;8(7):725-33.
Sen et al., Artemisinin triggers induction of cell-cycle arrest and apoptosis in Leishmania donovani promastigotes. J Med Microbiol. Sep. 2007;56(Pt 9):1213-8.
Sequence Search Result.
Shalaby et al., Development of humanized bispecific antibodies reactive with cytotoxic lymphocytes and tumor cells overexpressing the HER2 protooncogene. Exp. Med. 1992; 175:217-25.
Shangary et al., Peptides derived from BH3 domains of Bcl-2 family members: a comparative analysis of inhibition of Bcl-2, Bcl-x(L) and Bax oligomerization, induction of cytochrome c release, and activation of cell death. Biochemistry. Jul. 30, 2002;41(30):9485-95.

Shimizu et al., Proapoptotic BH3-only Bcl-2 family members induce cytochrome c release, but not mitochondrial membrane potential loss, and do not directly modulate voltage-dependent anion channel activity. Proc Natl Acad Sci U S A. Jan. 18, 2000;97(2):577-82.
Shopes, A genetically engineered human IgG mutant with enhanced cytolytic activity. J Immunol. 1992. 148:2918-2922.
Song et al., Carbon monoxide promotes Fas/CD95-induced apoptosis in Jurkat cells. J Biol Chem. Oct. 22, 2004;279(43):44327-34. Epub Jul. 27, 2004. Erratum in: J Biol Chem. Jun. 10, 2005;280(23):22555.
Stevenson et al., A chimeric antibody with dual Fc regions (bisFabFc) prepared by manipulations at the IgG hinge. Anti-Cancer Drug Design. 1989;3:219-30.
Strupp et al., Treatment of Cells with Detergent Activates Caspases and Induces Apoptotic Cell Death. J. Membrane Biology. Jun. 2000;175(3): 181-9.
Suresh et al., Bispecific Monoclonal Antibodies from Hybrid Hybridomas. Methods in Enzymology. 1986;121:210-28.
Suzuki et al., Possible Existence of Common Internalization Mechanisms among Arginine-rich Peptides. J. Biol. Chem. 2002;277:2437-43.
Terradillos et al. FEBS Lett. 2002;522(1-3):29-34.
Traunecker et al., Bispecific single chain molecules (Janusins) target cytotoxic lymphocytes on HIV infected cells. EMBO J. 1991;10:3655-9.
Tutt et al., Trispecific F(ab')3 derivatives that use cooperative signaling via the TCR/CD3 complex and CD2 to activate and redirect resting cytotoxic T cells. J. Immunol. 1991;147:60.
Vaquero et al., Extracellular matrix proteins protect pancreatic cancer cells from death via mitochondrial and nonmitochondrial pathways. Gastroenterology. Oct. 2003;125(4):1188-202.
Vaux et al., Bcl-2 gene promotes haemopoietic cell survival and cooperates with c-myc to inmortalize pre-B cells. Nature. 1988;335(6189):440-42.
Verhoeyen et al., Reshaping Human Antibodies: Grafting an Antilysozyme Activity. Science. 1988;239:1534-6.
Vieira et al., Cell permeable BH3-peptides overcome the cytoprotective effect of Bcl-2 and Bcl-XL. Oncogene. 2002 21:1963-77.
Vitetta et al., Redesigning Nature's Poisons to Create Anti-Tumor Reagents. Science. 1987;238:1098-104.
Vives et al., A Truncated HIV-1 Tat Protein Basic Domain Rapidly Translocates through the Plasma Membrane and Accumulates in the Cell Nucleus. J. Biol. Chem. 1997;272(25):16010-7.
Vo et al., Relative mitochondrial priming of myeloblasts and normal HSCs determines chemotherapeutic success in AML. Cell. Oct. 12, 2012;151(2):344-55.
Wang et al., Bid: A Novel BH3 Domain-Only Death Agonist. Genes Dev. 1996;10(22):2859-69.
Wang et al., Cell Permeable Bcl-2 binding Peptides: A Chemical Approach to Apoptosis Induction in Tumor Cells. Cancer Res. 2000;60:1498-502.
Wang et al., Structure based discovery of an organic compound that binds Bcl-2 protein and induces apoptosis of tumor cells. PNAS. 2000;97:7124-9.
Wang, The Expanding Role of Mitochondria in Apoptosis. Genes Dev. 2001;15:2922-33.
Wei et al., Proapoptotic BAX and BAK: A Requisite Gateway to Mitochondrial Dysfunction and Death. Science. 2001;292(5517):727-30.
Wei et al., tBID, a membrane-targeted death ligand, oligomerizes BAK to release cytochrome c. Genes & Development. 2000;14:2060-71.
Weinstein, Addiction to Oncogenes—the Achilles Heal of Cancer. Science. 2002;297:63-4.
Werner et al., Bcl-2 Family Member Bfl-1/A1 Sequesters Truncated Bid to Inhibit its Collaboration With Pro-Apoptotic Bak or Bax. J. Biol. Chem. 2002;277(25):22781-8.
Westerhoff et al., Magainins and the disruptioin of membrane-linked free-energy transduction. Proc. Natl. Acad. Sci. USA. Sep. 1989;86(17):6597-601.
Wilkinson, Immunochemical techniques inspire development of new antibody purification methods. The Scientist. 2000;14(8):25-8.

(56) References Cited

OTHER PUBLICATIONS

Willis et al., Apoptosis Initiated When BH3 Ligands Engage Multiple Bcl-2Homologs, not Bax or Bak. Science. Feb. 2007;315:856-9.
Willis et al., Proapoptotic Bak is sequestered by Mcl-1 and Bcl-xL, but not Bcl-2, until displaced by BH3-only proteins. Genes Dev. 2005;19:1294-305.
Wolff et al., Monoclonal antibody homodimers: Enhanced antitumor activity in Nude Mice. Cancer Research. 1993;53:2560-5.
Wolter et al., Movement of Bax from the Cytosol to Mitochondria during Apoptosis. J. Cell Biol. 1997;139(5):1281-92.
Yamaguchi et al., Bcl-XL Protects BimEL-induced Bax Conformational Change and Cytochrome c Release Independent of Interacting with Bax or BimEL. J. Biol. Chem. 2002;277(44):41604-12.
Yang et al., Bad, a Heterodimeric Partner for Bcl-X.sub.L and Bcl-2, Displaces Bax and Promotes Cell Death. Cell. 1995;80(2):285-91.
Yang et al., Calculation of Protein Conformation from Circular Dichroism. Methods Enzymol. 1986;130:208-69.
Yasuda et al., BNIP3 α: a Human Homolog of Mitochondrial Proapoptotic protein BNIP3. Cancer Res. 1999;59:533-7.
Yi et al., Inhibition of Bid-induced apoptosis by Bcl-2. tBid insertion, Bax translocation, and Bax/Bak oligomerization suppressed. J Biol Chem. May 9, 2003;278(19):16992-9. Epub Mar. 6, 2003.
Zha et al., BH3 Domain of BAD is Required for Heterodimerization with Bcl-X.sub.L and Proapoptotic Activity. J. Biol. Chem. 1997;272(39):24101-4.
Zha et al., Posttranslational N-Myristoylation of BID as a Molecular Switch for targeting Mitochondria and Apoptosis. Science. 2000;290(5497)1761-5.
Zha et al., Serine Phosphorylation of Death Agonist BAD in Response to Survival Factor Results in Binding to 14-3-3 Not BCL-X.sub.L. Cell. 1996;87:619-28.
Zhou et al., Novel mutant-selective EGFR kinase inhibitors against EGFR T790M. Nature. Dec. 24, 2009;462(7276):1070-4.
Zong et al., BH3-only proteins that bind pro-survival Bcl-2 family members fail to induce apoptosis in the absence of Bax and Bak. Genes & Development. 2001;15:1481-6.
Campos et al., Method for monitoring of mitochondrial cytochrome c release during cell death: Immunodetection of cytochrome c by flow cytometry after selective permeabilization of the plasma membrane. Cytometry A. Jun. 2006;69(6):515-23.
Extended European Search Report for EP16787039.3 dated Oct. 4, 2018.
Extended European Search Report for EP16787045.0 dated Oct. 4, 2018.
EP16787039.3, Oct. 4, 2018, Extended European Search Report.
EP16787045.0, Oct. 4, 2018, Extended European Search Report.
U.S. Appl. No. 16/508,459, filed Jul. 11, 2019, Pending.
Emerman et al., Effects of defined medium, fetal bovine serum, and human serum on growth and chemosensitivities of human breast cancer cells in primary culture: inference for in vitro assays. In Vitro Cell Dev Biol. Feb. 1987;23(2): 134-40.
Akgul et al., In vivo localisation and stability of human Mcl-1 using green fluorescent protein (GFP) fusion proteins. FEBS Lett. Jul. 28, 2000;478(1-2):72-6.
Foight et al., Designed BH3 peptides with high affinity and specificity for targeting Mcl-1 in cells. ACS ChemBiol. Sep. 19, 2014;9(9):1962-8. doi: 10.1021/cb500340w. Epub Jul. 23, 2014.
Pan et al., Selective BCL-2 inhibition by ABT-199 causes on-target cell death in acute myeloid leukemia. Cancer Discov. Mar. 2014;4(3):362-75. doi: 10.1158/2159-8290.CD-13-0609. Epub Dec. 17, 2013.
Rizvi et al., Platelet-derived growth factor primes cancer-associated fibroblasts for apoptosis. J Biol Chem. Aug. 15, 2014;289(33):22835-49. doi: 10.1074/jbc.M114.563064. Epub Jun. 27, 2014.
U.S. Appl. No. 16/919,173, filed Jul. 2, 2020, Letai et al.
U.S. Appl. No. 16/939,736, filed Jul. 27, 2020, Letai et al.
International Search Report and Written Opinion for PCT/US2020/019999 dated Aug. 4, 2020.
Bhola et al., Functionally identifiable apoptosis-insensitive subpopulations determine chemoresistance in acute myeloid leukemia. J Clin Invest. Oct. 3, 2016;126(10):3827-3836. doi: 10.1172/JCI82908. Epub Sep. 6, 2016. PMID: 27599292; PMCID: PMC5096802.
Del Gaizo Moore et al., BH3 profiling—measuring integrated function of the mitochondrial apoptotic pathway to predict cell fate decisions. Cancer Lett. May 28, 2013;332(2):202-5. doi: 10.1016/j.canlet.2011.12.021. Epub Jan. 8, 2012.
Lieber et al., Apoptosis sensitizers enhance cytotoxicity in hepatoblastoma cells. Pediatr Surg Int. Feb. 2012;28(2):149-59. doi: 10.1007/s00383-011-2988-z.

* cited by examiner

|  | ACTIVATORS | | SENSITIZERS | | | | | |
|---|---|---|---|---|---|---|---|---|
|  | BIM | BID | BAD | BIK | NOXA | HRK | PUMA | BMF |
| BCL-2 | ▓ | ▓ | ▓ |  | ▓ | ▓ | ▓ | ▓ |
| BCL-XL | ▓ | ▓ | ▓ | ▓ | ▓ | ▓ | ▓ | ▓ |
| BCL-w | ▓ | ▓ | ▓ | ▓ | ▓ | ▓ | ▓ | ▓ |
| MCL-1 | ▓ | ▓ | ▓ |  | ▓ | ▓ | ▓ | ▓ |
| BFL-1 | ▓ | ▓ | ▓ | ▓ | ▓ | ▓ | ▓ | ▓ |

Fig. 18A

SEQUENCE LISTING

<160> NUMBER OF SEQ ID NOS: 15

<210> SEQ ID NO 1
<211> LENGTH: 20
<212> TYPE: PRT

```
<213> ORGANISM: Artificial sequence
<220> FEATURE:
<223> OTHER INFORMATION: Chemically synthesized peptide

<400> SEQUENCE: 1

Glu Asp Ile Ile Arg Asn Ile Ala Arg His Leu Ala Gln Val Gly Asp
1               5                   10                  15

Ser Met Asp Arg
            20

<210> SEQ ID NO 2
<211> LENGTH: 20
<212> TYPE: PRT
<213> ORGANISM: Artificial sequence
<220> FEATURE:
<223> OTHER INFORMATION: Chemically synthesized peptide

<400> SEQUENCE: 2

Met Arg Pro Glu Ile Trp Ile Ala Gln Glu Leu Arg Arg Ile Gly Asp
1               5                   10                  15

Glu Phe Asn Ala
            20

<210> SEQ ID NO 3
<211> LENGTH: 20
<212> TYPE: PRT
<213> ORGANISM: Artificial sequence
<220> FEATURE:
<223> OTHER INFORMATION: Chemically synthesized peptide

<400> SEQUENCE: 3

Glu Asp Ile Ile Arg Asn Ile Ala Arg His Ala Ala Gln Val Gly Ala
1               5                   10                  15

Ser Met Asp Arg
            20

<210> SEQ ID NO 4
<211> LENGTH: 25
<212> TYPE: PRT
<213> ORGANISM: Artificial sequence
<220> FEATURE:
<223> OTHER INFORMATION: Chemically synthesized peptide

<400> SEQUENCE: 4

Leu Trp Ala Ala Gln Arg Tyr Gly Arg Glu Leu Arg Arg Met Ser Asp
1               5                   10                  15

Glu Phe Glu Gly Ser Phe Lys Gly Leu
            20                  25

<210> SEQ ID NO 5
<211> LENGTH: 20
<212> TYPE: PRT
<213> ORGANISM: Artificial sequence
<220> FEATURE:
<223> OTHER INFORMATION: Chemically synthesized peptide

<400> SEQUENCE: 5

Met Glu Gly Ser Asp Ala Leu Ala Leu Arg Leu Ala Cys Ile Gly Asp
1               5                   10                  15

Glu Met Asp Val
            20

<210> SEQ ID NO 6
<211> LENGTH: 20
```

```
<212> TYPE: PRT
<213> ORGANISM: Artificial sequence
<220> FEATURE:
<223> OTHER INFORMATION: Chemically synthesized peptides

<400> SEQUENCE: 6

Ala Glu Leu Pro Pro Glu Phe Ala Ala Gln Leu Arg Lys Ile Gly Asp
1               5                   10                  15

Lys Val Tyr Cys
            20

<210> SEQ ID NO 7
<211> LENGTH: 20
<212> TYPE: PRT
<213> ORGANISM: Artificial sequence
<220> FEATURE:
<223> OTHER INFORMATION: Chemically synthesized peptide

<400> SEQUENCE: 7

Pro Ala Asp Leu Lys Asp Glu Cys Ala Gln Leu Arg Arg Ile Gly Asp
1               5                   10                  15

Lys Val Asn Leu
            20

<210> SEQ ID NO 8
<211> LENGTH: 20
<212> TYPE: PRT
<213> ORGANISM: Artificial sequence
<220> FEATURE:
<223> OTHER INFORMATION: Chemically synthesized peptide

<400> SEQUENCE: 8

Ser Ser Ala Ala Gln Leu Thr Ala Ala Arg Leu Lys Ala Leu Gly Asp
1               5                   10                  15

Glu Leu His Gln
            20

<210> SEQ ID NO 9
<211> LENGTH: 20
<212> TYPE: PRT
<213> ORGANISM: Artificial sequence
<220> FEATURE:
<223> OTHER INFORMATION: Chemically synthesized peptide

<400> SEQUENCE: 9

Val Val Glu Gly Glu Lys Glu Val Glu Ala Leu Lys Lys Ser Ala Asp
1               5                   10                  15

Trp Val Ser Asp
            20

<210> SEQ ID NO 10
<211> LENGTH: 20
<212> TYPE: PRT
<213> ORGANISM: Artificial sequence
<220> FEATURE:
<223> OTHER INFORMATION: Chemically synthesized peptide

<400> SEQUENCE: 10

Glu Gln Trp Ala Arg Glu Ile Gly Ala Gln Leu Arg Arg Met Ala Asp
1               5                   10                  15

Asp Leu Asn Ala
            20

<210> SEQ ID NO 11
```

```
<211> LENGTH: 20
<212> TYPE: PRT
<213> ORGANISM: Artificial sequence
<220> FEATURE:
<223> OTHER INFORMATION: Chemically synthesized peptide

<400> SEQUENCE: 11

His Gln Ala Glu Val Gln Ile Ala Arg Lys Leu Gln Leu Ile Ala Asp
1               5                   10                  15

Gln Phe His Arg
            20

<210> SEQ ID NO 12
<211> LENGTH: 25
<212> TYPE: PRT
<213> ORGANISM: Artificial sequence
<220> FEATURE:
<223> OTHER INFORMATION: Chemically synthesized peptide

<400> SEQUENCE: 12

Asn Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 13
<211> LENGTH: 25
<212> TYPE: PRT
<213> ORGANISM: Artificial sequence
<220> FEATURE:
<223> OTHER INFORMATION: Chemically synthesized primer

<400> SEQUENCE: 13

Leu Trp Ala Ala Gln Arg Tyr Gly Arg Glu Ala Arg Arg Met Ser Asp
1               5                   10                  15

Glu Phe Glu Gly Ser Phe Lys Gly Leu
            20                  25

<210> SEQ ID NO 14
<211> LENGTH: 20
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(6)
<223> OTHER INFORMATION: Wherein Xaa is any amino acid
<220> FEATURE:
<221> NAME/KEY: MISC_FEATURE
<222> LOCATION: (9)..(10)
<223> OTHER INFORMATION: Wherein Xaa is any amino acid
<220> FEATURE:
<221> NAME/KEY: MISC_FEATURE
<222> LOCATION: (12)..(14)
<223> OTHER INFORMATION: Wherein Xaa is any amino acid
<220> FEATURE:
<221> NAME/KEY: MISC_FEATURE
<222> LOCATION: (17)..(20)
<223> OTHER INFORMATION: Wherein Xaa is any amino acid

<400> SEQUENCE: 14

Xaa Xaa Xaa Xaa Xaa Xaa Ile Ala Xaa Xaa Leu Xaa Xaa Xaa Gly Asp
1               5                   10                  15

Xaa Xaa Xaa Xaa
            20
```

```
<210> SEQ ID NO 15
<211> LENGTH: 20
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(10)
<223> OTHER INFORMATION: Wherein Xaa is any amino acid
<220> FEATURE:
<221> NAME/KEY: MISC_FEATURE
<222> LOCATION: (12)..(15)
<223> OTHER INFORMATION: Wherein Xaa is any amino acid
<220> FEATURE:
<221> NAME/KEY: MISC_FEATURE
<222> LOCATION: (17)..(20)
<223> OTHER INFORMATION: Wherein Xaa is any amino acid

<400> SEQUENCE: 15

Xaa Xaa Xaa Xaa Xaa Xaa Xaa Xaa Xaa Xaa Leu Xaa Xaa Xaa Xaa Asp
1               5                   10                  15

Xaa Xaa Xaa Xaa
            20
```

METHODS OF DETERMINING CELLULAR CHEMOSENSITIVITY

RELATED APPLICATIONS

This application is a continuation of U.S. Ser. No. 13/478,831, filed May 23, 2012, which is a continuation of U.S. Ser. No. 11/695,321, filed Apr. 2, 2007, which claims the benefit U.S. Ser. No. 60/788,138, filed Mar. 31, 2006, the contents of each of which are incorporated herein by reference in their entirety.

STATEMENT AS TO FEDERALLY SPONSORED RESEARCH

This invention was made with government support under grant numbers K08 CA102548 and CA092625 awarded by The National Institutes of Health. The government has certain rights in the invention.

FIELD OF THE INVENTION

The invention relates to generally methods of determining cellular chemosensitivity by determining the pattern of sensitivity of a cell to a panel of BH3 domain peptides.

BACKGROUND OF THE INVENTION

Programmed cell death, referred to as apoptosis, plays an indispensable role in the development and maintenance of tissue homeostasis within all multicellular organisms (Raff, Nature 356: 397-400, 1992). Genetic and molecular analysis from nematodes to humans has indicated that the apoptotic pathway of cellular suicide is highly conserved (Hengartner and Horvitz, Cell 76: 1107-1114, 1994). In addition to being essential for normal development and maintenance, apoptosis is important in the defense against viral infection and in preventing the emergence of cancer.

Diverse intrinsic death signals emanating from multiple subcellular locales all induce the release of cytochrome c from mitochondria to activate Apaf-1 and result in effector caspase activation. Proteins in the BCL-2 family are major regulators of the commitment to programmed cell death as well as executioners of death signals at the mitochondrion. Members of this family include both pro- and anti-apoptotic proteins and share homology in up to four conserved regions termed BCL-2 homology (BH) 1-4 domains (Adams and Cory, 1998). The family can be divided into three main sub-classes. The anti-apoptotic proteins, which include BCL-2 and BCL-$X_L$, are all "multidomain," sharing homology throughout all four BH domains. However, the pro-apoptotic proteins can be further subdivided and include multidomain proteins, such as BAX and BAK, which possess sequence homology in BH1-3 domains. The more distantly related "BH3-only" proteins are to date all pro-apoptotic and share sequence homology within the amphipathic α-helical BH3 region, which is required for their apoptotic function (Chittenden et al., 1995; O'Connor et al., 1998; Wang et al., 1996; Zha et al., 1997).

Multidomain pro-apoptotic proteins such as BAX and BAK upon receipt of death signals participate in executing mitochondrial dysfunction. In viable cells, these proteins exist as monomers. In response to a variety of death stimuli, however, inactive BAX, which is located in the cytosol or loosely attached to membranes, inserts deeply into the outer mitochondrial membrane as a homo-oligomerized multimer (Eskes et al., 2000; Gross et al., 1998; Wolter et al., 1997).

Inactive BAK resides at the mitochondrion where it also undergoes an allosteric conformational change in response to death signals, which includes homo-oligomerization (Griffiths et al., 1999; Wei et al., 2000). Cells deficient in both BAX and BAK are resistant to a wide variety of death stimuli that emanate from multiple locations within the cell (Wei et al., 10 2001).

The BH3-only molecules constitute the third subset of this family and include BID, NOXA, PUMA, BIK, BIM and BAD (Kelekar and Thompson, 1 998). These proteins share sequence homology only in the amphipathic α-helical BH3 region which mutation analysis indicated is required in pro-apoptotic members for their death activity. Moreover, the BH3-only proteins require this domain to demonstrate binding to "multidomain" BCL-2 family members. Multiple binding assays, including yeast two-hybrid, co-immunoprecipitation from detergent solubilized cell lysates and in-vitro pull down experiments indicate that individual BH3-only molecules display some selectivity for multidomain BCL-2 members (Boyd et al., 1995; O'Connor et al., 1998; Oda et al., 2000; Wang et al., 1996; Yang et al., 1995). The BID protein binds pro-apoptotic BAX and BAK as well as anti-apoptotic BCL-2 and BCL-$X_L$ (Wang et al., 1996; Wei et al., 2000). In contrast, BAD, and NOXA as intact molecules display preferential binding to anti-apoptotic members (Boyd et al., 1995; O'Connor et al., 1998; Oda et al., 2000; Yang et al., 1995)

SUMMARY OF THE INVENTION

In various aspects, the invention provides methods of predicting sensitivity of a cell to a therapeutic agent by contacting the cell or a cellular component (e.g., mitochondria) thereof with a BH3 domain peptide and detecting apoptosis. The presence of apoptosis indicates that the cell is sensitive to the therapeutic agent. Alternatively, sensitivity of a cell to a therapeutic agent is determined by providing a BH3 profile of the cancer cell and comparing the BH3 profile to a 30 control profile. A similarity of the BH3 profile in the cancer cell compared to the control profile indicates the cancer cell is sensitive to the therapeutic agent.

Also provided are methods of selecting an agent that is therapeutic for a subject by providing a cancer cell or cellular component thereof, contacting the cell or cellular component with a BH3 domain peptide or mimetic thereof and determining whether or not the BH3 domain peptide or mimetic induces apoptosis in the cancer cell or cellular component thereof to produce a test BH3 profile. The test BH3 profile is compared with a therapeutic agent BH3 profile. A similarity of the test BH3 profile compared to the therapeutic agent BH3 profile indicates that the agent is therapeutic for the subject.

Apoptosis is detected for example by detecting cytochrome c release from mitochondria. The therapeutic agent is a chemotherapeutic agent a BH3 domain mimetic, or antagonist of an anti-apoptotic protein. The BH3 domain peptide is derived from the BH3 domain of a BID, a BIM, a BAD, a BIK, a NOXA, a PUMA a BMF, or a HRK polypeptide. Exemplary BH3 domain peptides include SEQ ID NO: 1-14 and 15. The BH3 domain peptide is an activator or a sensitizer of apoptosis. Preferably, the BH3 domain peptide is a sensitizer.

A profile containing a pattern of mitochondrial sensitivity to BH3 peptides taken from one or more subjects who have cancer is also provided by the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 18A is a chart showing the interaction pattern between BH3 peptides and antiapoptotic proteins.

DETAILED DESCRIPTION OF THE INVENTION

Figure 1A:
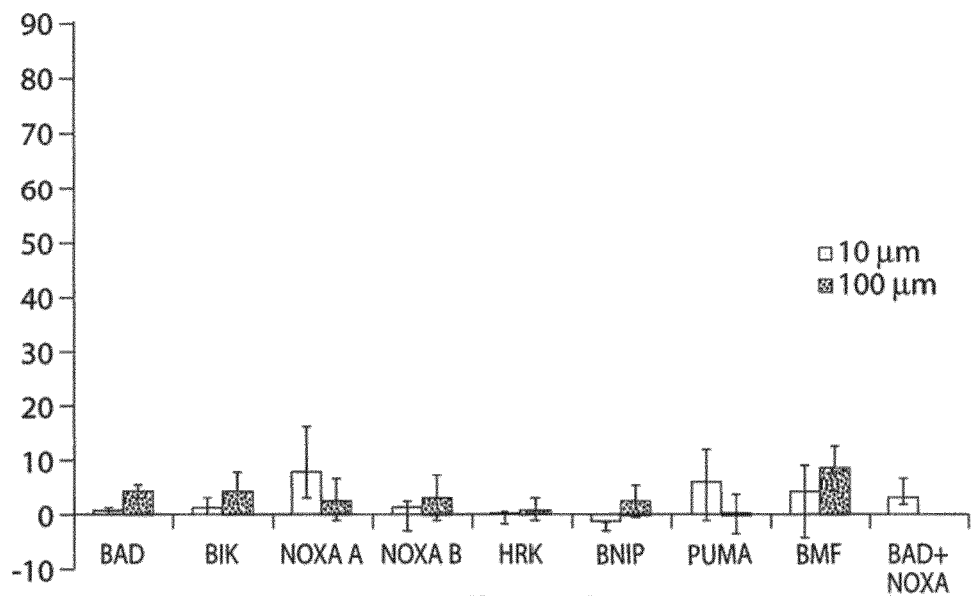
FIG. 1A is a bar chart showing the effects of sensitizer BH3 peptides on cytochrome c release from mouse liver mitochondria. Peptide concentrations were 10 uM unless otherwise indicated; tBID concentration was 13 nM. Average and standard deviation from at least three independent assays performed for each antiapoptotic protein are shown.
Figure 1B:
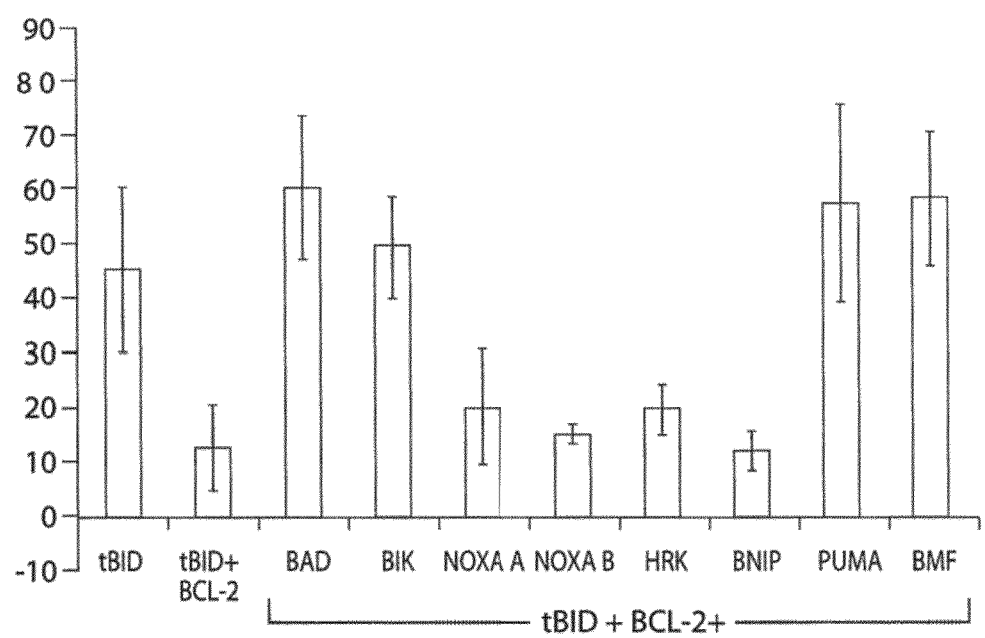
FIG. 1B is a bar chart showing the effects of tBID (first bar) and BCL-2 (1.2 uM, second bar) on cytochrome c release from mitochondria. The effect of sensitizer BH3 peptides on restoration of cytochrome c release is also shown. Note that in each case, restoration of cytochrome c release corresponds to a high affinity interaction in Table 2B.
Figure 1C:
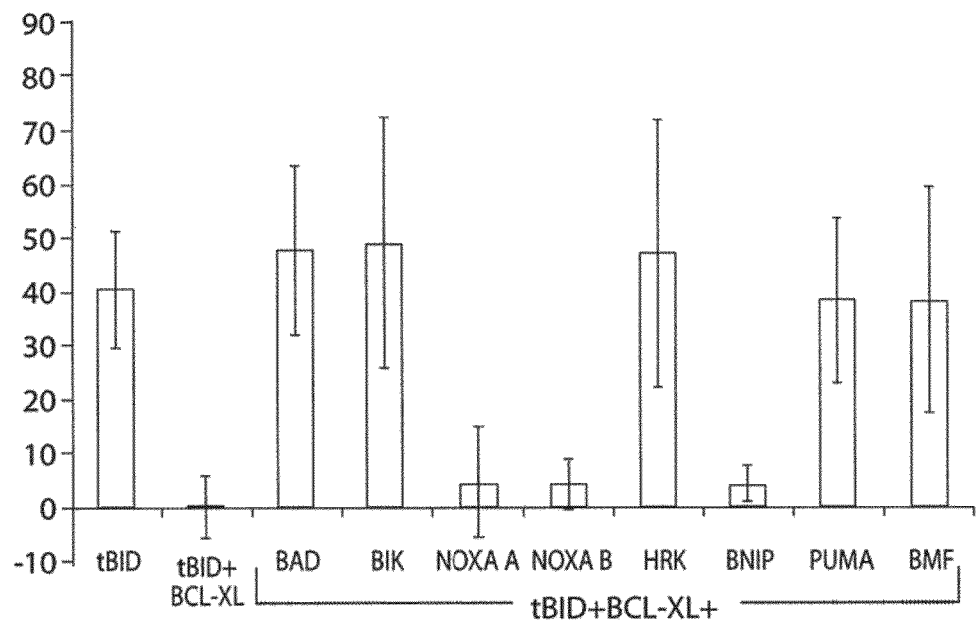
FIG. 1C is a bar chart showing the effects of tBID (first bar) and BCL-XL (0.25 uM, second bar) on cytochrome c release from mitochondria. The effect of sensitizer BH3 peptides on restoration of cytochrome c release is also shown.
Figure 1D:
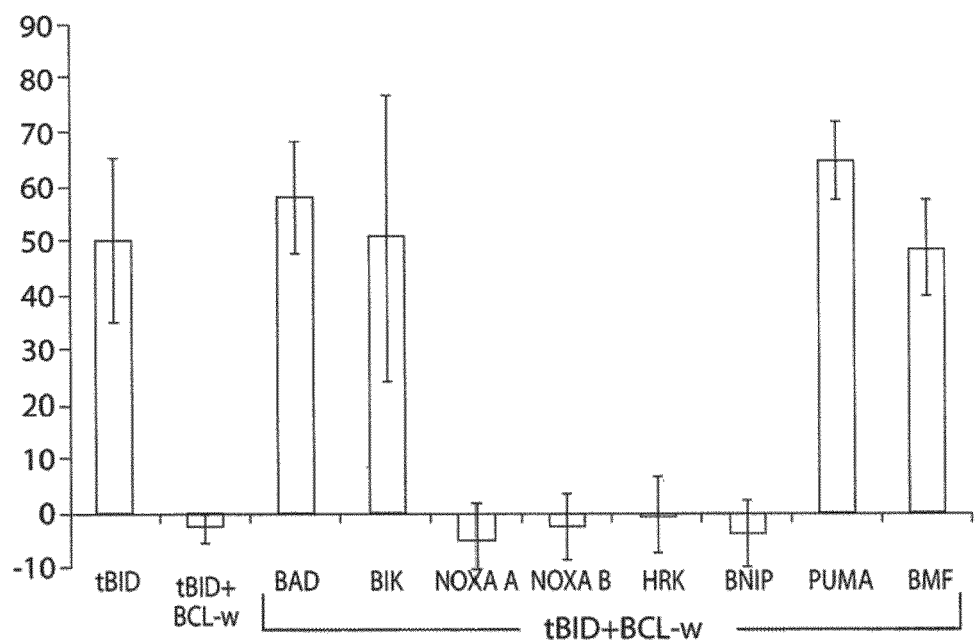
FIG. 1D is a bar chart showing the effects of tBID (first bar; note tBID concentration was 43 nM in this experiment) and BCL-w (6.3 uM; second bar) on cytochrome c release from mitochondria. The effect of sensitizer BH3 peptides on restoration of cytochrome c release is also shown.
Figure 1E:
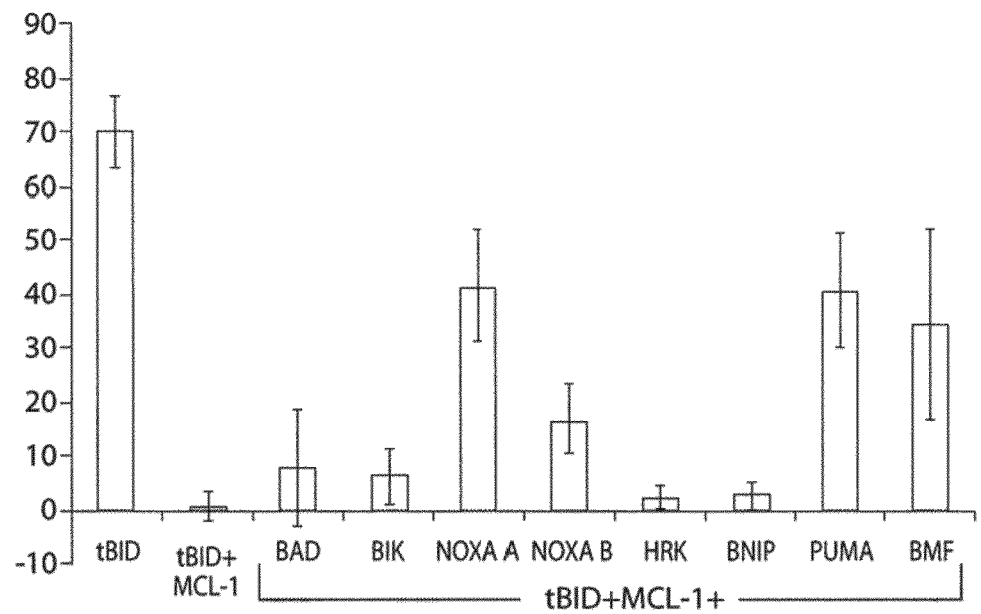
FIG. 1E is a bar chart showing the effects of tBID (first bar) and MCL-1 (1.1 uM; second bar) on cytochrome c release from mitochondria. The effect of sensitizer BH3 peptides on restoration of cytochrome c release is also shown.

The present invention is based in part by the discovery of a third cellular state with respect to programmed cell death. This state has been named "primed for death". Until the present discovery, only two states had been identified with respect to programmed cell death, alive and dead. Cells that are primed for death require tonic antiapoptotic function for survival.

Using a panel of peptides derived from BH3 domains of BH3-only proteins that selectively antagonize individual BCL-2 family members BCL-2, BCL-XL, BCL-w, MCL-1 and BFL-1, it was shown that cellular "addiction" to individual antiapoptotic proteins can be diagnosed based on mitochondrial response to these peptides. This panel of peptides is shown in Table 1 and are referred to herein BH3 domain peptides. Antiapoptotic proteins BCL-2, BCLXL, MCL-1, BFL-1 and BCL-w each bear a unique pattern of interaction with this panel of proteins. Cellular dependence on an antiapoptotic protein for survival is decoded based on the pattern of mitochondrial sensitivity to this peptide panel. This strategy is called BH3 profiling.

TABLE 1

| | AMINO ACID SEQUENCE | SEQ ID NO |
|---|---|---|
| BID | EDIIRNIARHLAQVGDSMDR | 1 |
| BIM | MRPEIWIAQELRRIGDEFNA | 2 |
| BIDmut | EDIIRNIARHAAQVGASMDR | 3 |
| BAD | LWAAQRYGRELRRMSDEFEGSFKGL | 4 |
| BIK | MEGSDALALRLACIGDEMDV | 5 |
| NOXA A | AELPPEFAAQLRKIGDKVYC | 6 |
| NOXA B | PADLKDECAQLRRIGDKVNL | 7 |
| HRK | SSAAQLTAARLKALGDELHQ | 8 |
| BNIP | VVEGEKEVEALKKSADWVSD | 9 |
| PUMA | EQWAREIGAQLRRMADDLNA | 10 |
| BMF | HQAEVQIARKLQLIADQFHR | 11 |
| huBAD | NLWAAQRYGRELRRMSDEFVDSFK K | 12 |
| BADmut | LWAAQRYGREARRMSDEFEGSFKGL | 13 |

Mitochondria were probed to determine a cell's state using our panel of sensitizer BH3-peptides, selective antagonists of antiapoptotic BCL-2 family members. Mitochondria that are primed for death are dependent on antiapoptotic protein function to prevent MOMP, so that they release cytochrome c when exposed to sensitizer BH3 peptides (See, FIG. 1, FIG. 4A, FIG. 5C, and FIG. 6B). In contrast, unprimed cells do not release cytochrome c when exposed to sensitizer BH3 peptides. Any cell from which mitochondria can be isolated can therefore be so tested and categorized as being primed or unprimed. Testing of mitochondria directly has the advantage of eliminating any contribution of transcription, translation, or post-translational modification events that might be triggered by transfection of peptide, protein, or expression vector into a living cell. A "snapshot" of the apoptotic state at a given time may be taken with minimal perturbation of the extant apoptotic machinery. In summary, the methods of the invention allow capture if information about a fundamental aspect of cellular physiology.

Importantly, mitochondrial behavior was correlated to whole cell behavior in several models. Mitochondria were primed when cells were enduring a physiologic challenge, and BH3 profiling revealed a dependence on antiapoptotic proteins only when a cellular dependence was also demonstrated. As shown below in the EXAMPLES, FL5.12 cells and mitochondria became primed for death only after IL-3 withdrawal. For 2B4 cells, cells and mitochondria were primed for death only after dexamethasone treatment. For the primary BCL-2 dependent leukemia cells, the genomic instability, myc oncogene activation and checkpoint violation inherent to the cancer phenotype were sufficient to induce mitochondrial priming without further external intervention. The SCLC cell lines H164 and H1693 revealed a BCL-2 pattern of sensitivity to BH3 profiling likewise are sensitive to the BCL-2 antagonist ABT-737. In each case, mitochondrial studies correctly diagnosed the cellular dependence on an antiapoptotic BCL-2 family member. Furthermore, the identity of the individual family member could be decoded based on the pattern of mitochondrial sensitivity to our peptide panel. These results indicate that in some cells, like IL-3 replete FL5.12-BCL-2 cells, BCL-2 overexpression provides extra antiapoptotic reserve. In others, like the murine leukemias, high levels of BCL-2 are present, but the BCL-2 is so highly occupied by activator BH3 proteins that the cell has very poor antiapoptotic reserve, and is actually primed for death.

Not all cells are sensitive to antagonism of antiapoptotic proteins. Sensitive cells are "primed for death" with death signals carried by a select subset of proapoptotic proteins of the BCL-2 family. Some cancer cells may be tonically primed for death, and thus are selectively susceptible to agents that provoke or mimic sensitizer BH3-only domains. It has been postulated that inhibition of apoptosis is a requirement of oncogenesis (Green and Evan, 2002; Hanahan and Weinberg, 2000). In what may be an attempt to meet this requirement, many types of cancer cells overexpress antiapoptotic BCL-2 family members. Understanding how these proteins function is therefore critical to understanding how cancer cells maintain survival. The methods of the present invention allows the systematic investigation how antiapoptotic BCL-2 family members interact with BH3-only family members to control mitochondrial outer membrane penneabilization (MOMP) and commitment to apoptosis. Antiapoptotic proteins show selective affinity for binding BH3 peptides derived from BH3-only proteins. Furthermore, antagonism of antiapoptotic family members results in MOMP only when the antiapoptotic proteins are "primed" with activator BH3 proteins, validating the critical role of activator BH3 domains in activating BAX/BAK. In cell culture models, activator "priming" can be observed following experimentally-induced death signaling, and that such priming confers dependence on antiapoptotic family members. Remarkably, dependence on antiapoptotic BCL-2 family members can be captured functionally by the pattern of mitochondrial sensitivity to sensitizer BH3 domains. Accordingly, the invention features methods of determining the sensitivity of a cell to a therapeutic agent by identifying whether or not a cell is primed for death by determining the pattern of mitochondrial sensitivity to BH3 domain peptides.

BH3 Profiling

In various methods, sensitivity of a cell to an agent is determined. Cell sensitivity is determined by contacting a cell or cellular component (e.g., mitochondria) with a BH3 domain peptide. A cell is sensitive to an agent if apoptosis is detected. Alternatively, cell sensitivity is determined by providing a test BH3 profile of the cell and comparing the profile to a cancer cell BH3 profile. A similarity of the test profile and the control profile indicates that the cell is sensitive to an agent. A BH3 profile is a pattern of sensitivity to BH3 peptides of the cell. Sensitivity is indicated by apoptosis. A cancer cell BH3 profile is a pattern of sensitivity to BH3 peptides in a cancer cell whose responsiveness or lack thereof to a particular agent is known. Optionally, the test BH3 profile is compared to more than one cancer cell BH3 profile. Thus, by comparing the test BH3 profile to the control BH3 profile sensitivity to an agent is determined.

The cell or cellular component is a cancer cell or a cell that is suspected of being cancerous. The cell is permeabilized to permit the BH3 peptides access to the mitochondria. Cells are permeabilized by methods known in the art. For example, the cell are permeabilized by contacting the cell with digitonin. After the cell is permeabilized, the cells are treated with a potentiometric dye. Examples of potentiometric dyes include the green-fluorescent JC-1 probe (5,5',6,6'-tetrachloro-1,1',3,3'-tetraethylbenzimidazolylcarbocyanine iodide) or dihydrorhodamine 123.

JC-1 is a lipophilic, cationic dye that enters mitochondria in proportion to the membrane potential JC-1 exists as a monomer in water at low membrane potential (M). However, at higher potentials, JC-1 forms red-fluorescent "J-aggregates". As a monomer the dye has an absorption/emission maxima of 527 nm while at high membrane potential the emission maximum is 590 nm. Thus, ratio measurements of the emission of this cyanine dye can be used as a sensitive measure of mitochondrial membrane potential. The dye allows for a dual measurement of dye concentration that does not require the measurement of a nuclear or cytoplasmic reference values. Studies using isolated mitochondria have shown that the 527 nm emission from monomeric JC-1 increases almost linearly with membrane M potentials ranging from 46 to 182 mV, whereas the 590 nm J-aggregate emission is less sensitive to M values less negative than 140 my and is strongly sensitive to potential values in the range of 140 to 182 mV (Di Lisa et al., 1995) Optical filters designed for fluorescein and tetramethylrhodamine can be used to separately visualize the monomer and J-aggregate forms, respectively. Alternatively, both forms can be observed simultaneously using a standard fluorescein long-pass optical filter set.

Dihydrorhodamine 123 an uncharged, nonfluorescent agent that can be converted by oxidation to the fluorescent laser dye rhodamine 123 (R123).

The cell is from a subject known to or suspected of having cancer. The subject is preferably a mammal. The mammal is, e.g., a human, non-human primate, mouse, rat, dog, cat, horse, or cow. The subject has been previously diagnosed as having cancer, and possibly has already undergone treatment for cancer. Alternatively, the subject has not been previously diagnosed as having cancer.

The agent is a therapeutic agent such as a chemotherapeutic agent. For example the agent is a mimetic of sensitizer BH3 domains or an antagonist of an anti-apoptotic protein. Apoptosis, i.e., cell death is identified by know methods. For example, characteristics of apoptosis include the cell shrinks, develop bubble-like blebs on their surface, have the chromatin (DNA and protein) in their nucleus degraded, and have their mitochondria break down with the release of cytochrome c, loss of mitochondrial membrane potential, break into small, membrane wrapped, fragments, or phosphatidylserine, which is normally hidden within the plasma membrane, is exposed on the surface of the cell.

The difference in the level apoptosis of a cell that has been contacted with a BH3 peptide compared to a cell that has not been contacted with a BH3 peptide is statistically significant. By statistically significant is meant that the alteration is greater than what might be expected to happen by chance alone. Statistical significance is determined by method known in the art. For example statistical significance is determined by p-value. The p-value is a measure of probability that a difference between groups during an experiment happened by chance. ($P(z>Z_{observed})$). For example, a p-value of 0.01 means that there is a 1 in 100 chance the result occurred by chance. The lower the p-value, the more likely it is that the difference between groups was caused by treatment. An alteration is statistically significant if the p-value is or less than 0.05. Preferably, the p-value is 0.04, 0.03, 0.02, 0.01, 0.005, 0.001 or less.

The invention also includes a profile of a pattern of mitochondrial sensitivity to BH3 sensitizer peptides taken from one or more subjects who have cancer.

BH3 Domain Peptides

A BH3 domain peptide is less than 195 amino acids in length, e.g., less than or equal to 150, 100, 75, 50, 35, 25 or 15 amino acid in length. For example a BH3 peptide includes the sequence of SEQ ID NO: 1-13 shown in Table 1.

A BH3 domain peptide include a peptide which includes (in whole or in part) the sequence NH$_2$-XXXXXXI-AXXLXXXGDXXXX-COOH (SEQ ID NO: 14) or NH$_2$-XXXXXXXXXXLXXXXDXXXX-COOH (SEQ ID NO: 15). As used herein X may be any amino acid. Alternatively, the BH3 domain peptides include at least 5, 6, 7, 8, 9, 15 or more amino acids of SEQ ID NO: 14 or SEQ ID NO: 15).

Optionally, the BH3 domain peptide is attached to transduction domain. A transduction domain compound that directs a peptide in which it is present to a desired cellular destination Thus, the transduction domain can direct the peptide across the plasma membrane, e.g., from outside the cell, through the plasma membrane, and into the cytoplasm. Alternatively, or in addition, the transduction domain can direct the peptide to a desired location within the cell, e.g., the nucleus, the ribosome, the ER, mitochondria, a lysosome, or peroxisome.

In some embodiments, the transduction domain is derived from a known membranetranslocating sequence. Alternatively, transduction domain is a compound that is known to facilitate membrane uptake such as polyethylene glycol, cholesterol moieties, octanoic acid and decanoic acid.

For example, the trafficking peptide may include sequences from the human immunodeficiency virus (HIV) 1 TAT protein. This protein is described in, e.g., U.S. Pat. Nos. 5,804,604 and 5,674,980, each incorporated herein by reference. The BH3 domain peptide is linked to some or all of the entire 86 amino acids that make up the TAT protein. For example, a functionally effective fragment or portion of a TAT protein that has fewer than 86 amino acids, which exhibits uptake into cells can be used. See e.g., Vives et al., *J. Biol. Chem.*, 272(25):16010-17 (1997), incorporated herein by reference in its entirety. A TAT peptide that includes the region that mediates entry and uptake into cells can be further defined using known techniques. See, e.g., Franked et al., *Proc. Natl. Acad. Sci, USA* 86: 7397-7401 (1989). Other sources for translocating sequences include, e.g., VP22 (described in, e.g., WO 97/05265; Elliott and O'Hare, *Cell* 88: 223-233 (1997)), *Drosophila* Antennapedia (Antp) homeotic transcription factor, HSV, poly-arginine, poly lysine, or non-viral proteins (Jackson et al, *Proc. Natl. Acad. Sci. USA* 89: 10691-10695 (1992)).

The transduction domain may be linked either to the N-terminal or the C-terminal end of BH3 domain peptide. A hinge of two proline residues may be added between the transduction domain and BH3 domain peptide to create the full fusion peptide. Optionally, the transduction domain is linked to the BH3 domain peptide in such a way that the transduction domain is released from the BH3 domain peptide upon entry into the cell or cellular component.

The transduction domain can be a single (i.e., continuous) amino acid sequence present in the translocating protein. Alternatively it can be two or more amino acid sequences, which are present in protein, but in the naturally-occurring protein are separated by other amino acid sequences.

The amino acid sequence of naturally-occurring translocation protein can be modified, for example, by addition, deletion and/or substitution of at least one amino acid present in the naturally-occurring protein, to produce modified protein. Modified translocation proteins with increased or decreased stability can be produced using known techniques. In some embodiments translocation proteins or peptides include amino acid sequences that are substantially similar, although not identical, to that of naturally-occurring protein or portions thereof. In addition, cholesterol or other lipid derivatives can be added to translocation protein to produce a modified protein having increased membrane solubility.

The BH3 domain peptide and the transduction domain can be linked by chemical coupling in any suitable manner known in the art. Many known chemical cross-linking methods are non-specific, i.e.; they do not direct the point of coupling to any particular site on the transport polypeptide or cargo macromolecule. As a result, use of non-specific cross-linking agents may attack functional sites or sterically block active sites, rendering the conjugated proteins biologically inactive.

One way to increasing coupling specificity is to directly chemical coupling to a functional group found only once or a few times in one or both of the polypeptides to be crosslinked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a cross-linking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. There are several intermolecular cross-linking reagents which can be utilized, See for example, Means and Feeney, CHEMICAL MODIFICATION OF PROTEINS, Holden-Day, 1974, pp. 39-43. Among these reagents are, for example, J-succinimidyl 3-(2-pyridyldithio) propionate (SPDP) or N, N'-(1,3-pbenylene) bismaleimide (both of which are highly specific for sulfhydryl groups and form irreversible linkages); N, N'-ethylene-bis-(iodoacetamide) or other such reagent having 6 to 11 carbon methylene bridges (which relatively specific for sulfhydryl groups); and 1,5-difluoro-2, 4-dinitrobenzene (which forms irreversible linkages with amino and tyrosine groups). Other cross-linking reagents useful for this purpose include: p,p'-difluoro-m,m'dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl) cyclohexane-1-carboxylate ("SMCC"), m-maleimidobenzoyl-N-hydroxysuccinimide ester ("MBS"), and succinimide 4-(p-maleimidophenyl) butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis (succinimidylpropionate) ("DSP"), and N-succinimidyl 3-(2-pyridyldithio) propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, CHEMISTRY OF PROTEIN CONJUGATION AND CROSS-LINKING, CRC Press (1991).

Chemical cross-linking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the cross-linking reagent, such as in "long-chain SPDP" (Pierce Chem. Co., Rockford, Ill., cat. No. 21651 H).

The BH3 domain peptides and/or the transduction domain peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., *Nature,* 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

Alternatively, the BH3 domain peptides and/or the transduction domain peptides are cyclic peptides. Cyclic peptides are prepared by methods known in the art. For example, macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology,* 137: 5182-5185 (1996)), or between two amino acid side chains. See, e.g., DeGrado, *Adv Protein Chem,* 39: 51-124 (1988).

BH3 domain peptides and/or the transduction domain peptides are easily prepared using modern cloning techniques, or may be synthesized by solid state methods or by site-directed mutagenesis. A domain BH3 peptide and/or the transduction domain peptides may include dominant negative forms of a polypeptide. In one embodiment, native BH3 domain peptides and/or transduction domain peptides can be isolated from cells or tissue sources by an appropriate purification scheme using standard protein purification techniques. In another embodiment, BH3 domain polypeptides and/or transduction domain peptides are produced by recombinant DNA techniques. Alternative to recombinant expression, BH3 domain peptides and/or transduction domain peptides can be synthesized chemically using standard peptide synthesis techniques.

An "isolated" or "purified" protein or biologically active portion thereof is substantially free of cellular material or other contaminating proteins from the cell or tissue source from which the BH3 domain peptide is derived, or substantially free from chemical precursors or other chemicals when chemically synthesized. The language "substantially free of cellular material" includes preparations of BH3 peptides and/or transduction domain peptides in which the protein is separated from cellular components of the cells from which it is isolated or recombinantly produced. In one embodiment, the language "substantially free of cellular material" includes preparations of BH3 domain peptides and/or the transduction domain peptides having less than about 30% (by dry weight) of non-BH3 domain peptide and/or non-transduction domain peptides (also referred to herein as a "contaminating protein"), more preferably less than about 20% of non-BH3 peptide and/or non-transduction domain peptides, still more preferably less than about 10% of non-BH3 peptide and/or non-transduction domain peptides, and most preferably less than about 5% non-BH3 domain peptide and/or non-transduction domain peptides. When the BH3 domain peptide and/or the transduction domain peptides or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BH3 domain peptides and/or the transduction domain peptides in which the protein is separated from chemical precursors or other chemicals that are involved in the synthesis of the protein. In one embodiment, the language "substantially free of chemical precursors or other chemicals" includes preparations of BH3 domain peptides and/or transduction domain peptides having less than about 30% (by dry weight) of chemical precursors or non-BH3 domain peptide and/or non-transduction domain peptides chemicals, more preferably less than about 20% chemical precursors or non-BH3 domain peptide and/or non-transduction domain peptides chemicals, still more preferably less than about 10% chemical precursors or non-BH3 domain peptide chemicals, and most preferably less than about 5% chemical precursors or non-BH3 domain peptide and/or non-transduction domain peptides chemicals.

The term "biologically equivalent" is intended to mean that the compositions of the present invention are capable of demonstrating some or all of the same apoptosis modulating effects, i.e., release of cytochrome c or BAK oligomerization although not necessarily to the same degree as the BH3 domain polypeptide deduced from sequences identified from cDNA libraries of human, rat or mouse origin or produced from recombinant expression symptoms.

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to sequences as indicated above for identity comparisons. Conservative amino acid changes satisfying this requirement are: R-K; E-D, Y-F, L-M; V-I, Q-H.

BH3 domain peptides can also include derivatives of BH3 domain peptides which are intended to include hybrid and modified forms of BH3 domain peptides including fusion proteins and BH3 domain peptide fragments and hybrid and modified forms in which certain amino acids have been deleted or replaced and modifications such as where one or more amino acids have been changed to a modified amino acid or unusual amino acid and modifications such as glycosylation so long as the hybrid or modified form retains the biological activity of BH3 domain peptides. By retaining the biological activity, it is meant that cell death is induced by the BH3 polypeptide, although not necessarily at the same level of potency as that of the naturally-occurring BH3 domain polypeptide identified for human or mouse and that can be produced, for example, recombinantly. The terms induced and stimulated are used interchangeably throughout the specification.

Preferred variants are those that have conservative amino acid substitutions made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a BH3 domain polypeptide is replaced with another amino acid residue from the same side chain family. Alternatively, in another embodiment, mutations can be introduced randomly along all or part of a BH3 coding sequence, such as by saturation mutagenesis, and the resultant mutants can be screened to identify mutants that retain activity.

Also included within the meaning of substantially homologous is any BH3 domain peptide which may be isolated by virtue of cross-reactivity with antibodies to the BH3 domain peptide described herein or whose encoding nucleotide sequences including genomic DNA, mRNA or cDNA may be isolated through hybridization with the complementary sequence of genomic or subgenomic nucleotide sequences or cDNA of the BH3 domain peptides herein or fragments thereof.

The invention will be further illustrated in the following non-limiting examples.

Example 1: General Methods

Reagents

ABT-737 and its negative control enantiomer which has lower affinity for BCL-2 family members were obtained from Abbott Laboratories (OltersdorfT, 2005).

GST-Pulldown 10 ug GST-BCL-w (or BH3 binding-defective R96P point mutant) were incubated with glutathione-agarose beads for one hour at 4° C. in binding buffer (140 mM NaCl, 10 mM Tris pH7.4). Beads were rinsed and incubated with approximately 0.2 ug tBID for 1 hr at 4° C. Beads were washed again and incubated with peptides for 1 hour at 4° C. tBTD protein was eluted from beads with 50 mM glutathione and loaded on a denaturing NuPAGE gel.

Cytochrome c Release

Mitochondria were purified from liver and FL5.12cells as previously described (Letai et al., 2002). Mitochondria were purified from leukemia cells and 2B4 cells as previously described for FL5.12 cells. Mitochondria were incubated with treatments for 45 (mouse liver mitochondria) or 35 minutes (FL5.12, 2B4, and leukemic mitochondria). Release of cytochrome c was determined by a comparison of cytochrome c in the pellet and supernatant following treatment, quantitated by ELISA (R&D systems). When results of multiple experiments were averaged, results from solvent-only (DMSO) treatments values were subtracted from each, so that 0 release reflects that observed in solvent-only treatments.

Alternatively, mitochondria were purified from freshly isolated CLL cells and cell lines by mechanical disruption followed by differential centrifugation, as previously described (Letai et al., 2002). Mitochondrial suspensions were made at 0.5 mg protein/ml, except for the case of ABT-737 and negative control enantiomer treatments, where 0.1 mg/ml was used. Release of cytochrome c was determined by a comparison of cytochrome c in the pellet and supernatant quantitated by ELISA (R&D systems).

Peptides

Peptides were synthesized by Tufts University Core Facility and purified by HPLC. Identity was confirmed by mass spectrometry. Stock solutions were made in DMSO. Peptides used for fluorescence polarization were synthesized with an N-terminus fluorescein tag and a 6-aminohexanoic acid linker. Sequences were taken from published sequences of murine BAD (LWAAQRYGRELRRMSDEFEGSFKGL; SEQ ID NO: 4) (Kelekar et al., 1997), BADmu (LWAAQRYGREARRMSDEFEGSFKGL; SEQ ID NO: 13, note L→A, a point mutation abrogating binding to BCL-2) (Zha et al., 1997), NOXA A (AELPPE-FAAQLRKIGDKVYC; SEQ ID NO: 6) (Oda et al., 2000), BMF (HQAEVQIARKLQLIADQFHR; SEQ ID NO: 11) (Puthalakath et al., 2001) and human BID (EDIIRNIAR-HLAQVGDSMDR; SEQ ID NO: 1) (Wang et al., 1996), BIM (MRPEIWIAQELRRIGDEFNA; SEQ ID NO: 2) (O'Connor et al., 1998), BIK (MEGSDALALR-LACIGDEMDV; SEQ ID NO: 5) (Boyd et al., 1995), BNIP3-a (VVEGEKEVEALKKSADWVSD; SEQ ID NO:

9) (Yasuda et al., 1999), hari-kiri (HRK) (SSAAQLTAARL-KALGDELHQ; SEQ ID NO: 8) (Inohara et al., 1997) and PUMA (EQWAREIGAQLRRMADDLNA; SEQ ID NO: 10) (Nakano and Vousden, 2001).

Recombinant Proteins

Antiapoptotic proteins were expressed in bacteria and affinity purified using glutathioneagarose (for GST-linked proteins) as previously described (Letai et al., 2002) or by nickel-NTA agarose beads (for His-tagged MCL-1) according to manufacturer protocol (Qiagen). Selected samples were additionally purified by anion exchange FPLC to obtain sufficient purity as judged by Coomassie staining of a denaturing gel. In each case, the C-terminus transmembrane domain was truncated to maintain solubility in aqueous solution. For binding assays, GST-linked proteins were used for BCL-2, BCL-XL, BCL-w and BFL-1; His-tagged MCL-1 was used. For the mitochondrial assays, the same proteins were used except for MCL-1, where a GST-linked protein was used. Constructs expressing GST-MCL-1, GST-BFL-1, and GST-BCL-w were kind gifts of Tilman Oltersdorf; His-tagged MCL-1 construct was a kind gift of Ruth Craig. The human sequence was used for each. Recombinant tBID was made as previously described; it contained double cysteine to serine substitutions which maintains wild-type ability to induce cytochrome c release (Oh et al., 2005).

Fluorescence Polarization Binding Assays

Binding assays were performed using fluorescence polarization as previously described (Letai et al., 2002). A minimum of three independent experiments were used to determine each dissociation constant. For BIM BH3 displacement assays, 25 nM fluorescein-linked BIM BH3 peptide was bound to 0.5 uM GST-BCL-2 or 0.1 uM GST-MCL-1 in binding buffer. NOXA or BAD BH3 peptides were then titrated and displacement of BIM BH3 monitored by loss of fluorescence polarization.

Immunoprecipitation

Cell lysates (250 ug) were incubated with 6C8 hamster anti-human BCL-2 antibody (3 ug) for at least 1 hour at room temperature in 1% CHAPS buffer (5 mM sodium phosphate pH 7.4; 2.5 mM EDTA; 100 mM sodium chloride; 1% w/v CHAPS, in the presence of protease inhibitors (Complete tablets; Roche)). Protein A-sepharose beads (Sigma) were added to precipitate complexes containing BCL-2. The beads were mixed with loading buffer prior to loading supernatant onto gel. For FLAG-MCL-1 immunoprecipitation, 2B4 cells were treated with 100 nM dexamethasone for 24 hours and lysed in 1% CHAPS buffer. 250 ug protein lysate was incubated with anti-FLAG antibody-conjugated agarose beads (Sigma) for 1 hour at 4° C. Protein was eluted from washed beads with 2.5 ug FLAG peptide. Eluant was loaded onto denaturing gel for electrophoresis.

Alternatively, Cell lysates (250 µg) were incubated with 6C8 hamster anti-human BCL-2 antibody (3 µg) for at least 1 hour at 4° C. in 0.1% Triton-X100 buffer. Protein A-sepharose beads (Sigma) were added to precipitate complexes containing BCL-2. The beads were mixed with loading buffer prior to loading supernatant onto a 100% Bis-Tris polyacrylamide gel for analysis. For displacement reactions, 50 µg of lysate were incubated with 3 µg 6C8 BCL-2 antibody for at least 1 hour at 4° C. in 0.1% Triton-X100 buffer or CHAPS buffer. Protein A-sepharose beads were added and incubated for 1 hour. Then the beads were pelleted and washed 3 times and resuspended in HE buffer (1 mM EDTA and 10 mM HEPES, pH 7.4, as in (Chipuk et al. 2004)). 1 µM ABT-737, 1 µM negative control enantiomer, or DMSO was added to the tube, incubated overnight; the supernatant was loaded onto a 10% Bis-Tris polyacrylamide gel (Invitrogen) for analysis.

Immunoblots

Protein lysates were obtained by cell lysis in 1% CHAPS buffer. Protein samples were size fractionated on NuPAGE 10% Bis-Tris polyacrylamide gels (Invitrogen). Antibodies were used to detect the following proteins on membrane: BIM (Calbiochem, 22-40); BCL-2 (Pharmingen,/100); PUMA (Prosci, NT); rabbit polyclonal anti-murine BID (Wang et al., 1996); BAK (Upstate, NT); BAX (Santa Cruz, N-20); Actin (Chemicon, MAB1501); CD-40 (Pharmingen, HM40-3); MCL-1 (Rockland). BAX oligomerization performed as previously described (Letai et al., 2002).

Alternatively, protein lysates were obtained by cell lysis in Triton-X100 (142.5 mM NaCl, 5 mM MgCl2, 10 mM HEPES, 1 mM EGTA, 0.1% Triton-X100 (Sigma)), RIPA (150 mM NaCl, 2 mM EDTA, 0.1 M Na2HPO4 pH 7.2, 0.2 mM NaVO4, 50 mM NaF, 1% sodium deoxycholate, 0.1% SDS, and % NP-40(Sigma)) or CHAPS (100 mM NaCl, 5 mM NaPO4, 2.5 mM EDT A, 1% CHAPS (Sigma)) buffer supplemented with a Complete protease inhibitor cocktail tablet (Roche). Protein samples were electrophoretically separated on NuPAGE 10% Bis-Tris polyacrylamide gels (Invitrogen). Antibodies were used to detect the following proteins on membrane: BIM (Calbiochem 22-40 or Abgent BH3 domain); BCL-2 (Pharmingen, /100); MCL-1 (Chemicon, RC-13).

Annexin-V Assay

Cells were stained with fluorescent conjugates of Annexin-V (BioVision) and propidium iodide (PI) and analyzed on a FACSCalibur machine (Becton-Dickinson).

Figure 11:
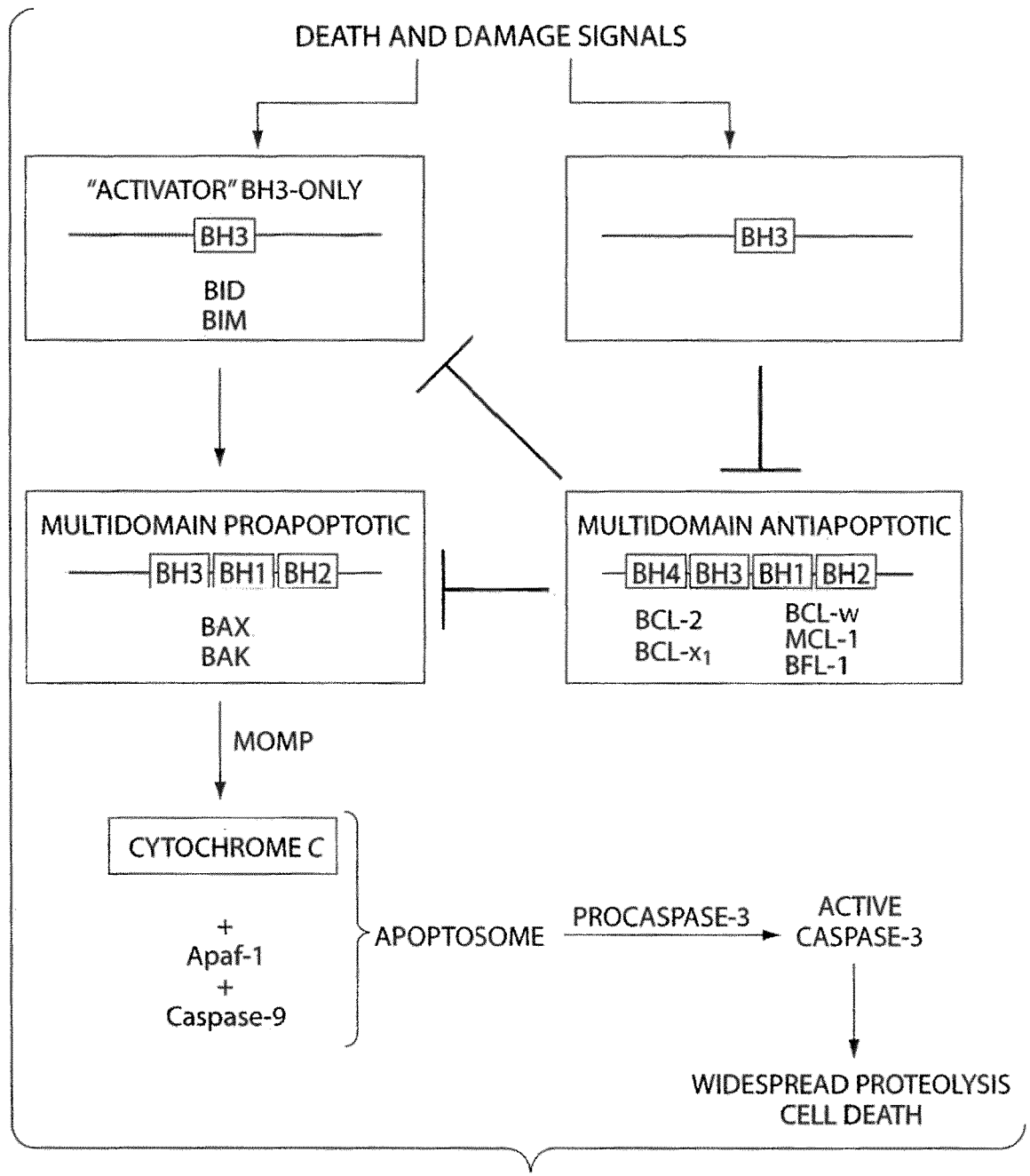
FIG. 11 is a diagram depicting the intrinsic or mitochondrial programmed cell death pathway. In response to death signaling, activator BH3-only proteins are triggered to interact with BAX and BAK, inducing BAX and BAK oligomerization. This oligomerization is followed by permeabilization of the mitochondrial outer membrane, which releases proapoptotic factors like cytochrome c to the cytosol. Cytosolic cytochrome c forms a complex with APAF-1 and Caspase-9 to make the holoenzyme known as the apoptosome, which in turn activates effector Caspase-3, leading to widespread proteolysis. This pathway can be interrupted by antiapoptotic members like BCL-2, which can bind activator BH3-only proteins, preventing their interaction with BAX and BAK. This inhibitory interaction can itself be antagonized by sensitizer BH3-only domains, which compete for the binding site in BCL-2, displacing activators bound by BCL-2.

Isolation and Short-Term Culture of Human Cells 15 ml of blood in heparin treated tubes was obtained from each anonymous CLL patient and processed without freezing. Equal volume of media (RPMI medium, 10% human bovine serum, supplemented with 10m/ml insulin and 10 mg/ml transferrin) was mixed with each sample and CLL cells isolated by centrifugation through Ficoll-PAQUE Plus (Amersham). Cells were washed twice in media and cultured at a density of 2.0×106 cells/ml for up to 48 hours. Samples for FIG. 11A were obtained from 24 consecutive patients identified with WBC >50,000/µl. All guidelines and regulations were followed in accordance with IRB protocols #99-224 (Dana-Farber Cancer Institute). Normal PBMC's were obtained from tubing discarded following platelet donation by anonymous normal donors and processed as above, except cultured without insulin and transferrin.

CLL Clinical Criteria

FISH analysis was performed by the Brigham and Women's Hospital cytogenetics laboratory using a CLL panel of multicolor probe sets (Vysis, Inc.) (Dohner et al., 2000). CLL cells were processed and IgVH and ZAP70 status were determined by the CLL Research Consortium Tissue core using previously established methods (Rassenti et al. 2004). Somatic hypermutation in the IgVH locus was classified as absent when >98% homology to germline was measured. Patient samples were classified as ZAP70 positive when >20% cells were positive; CD38 positive when >30% cells were positive. Multiple Myeloma Cell culture LP1 and L363 cells (kind gift from Ruben Carrasco) were cultured in Iscove's modified Dulbecco's medium with 10% fetal bovine serum.

Cell Culture

FL5.12 cells were cultured as described previously in Iscove's modified Dulbecco's medium, 10% fetal bovine serum, 1000 ug/ml G418 with or without IL-3 provided by 10% WEHI-3B supplement (supernatant of IL-3 secreting WEHI-3B cells). FL5.12 cells were stably transfected with a vector containing a neomycin resistance construct and either human BCL-2 cDNA (FL5.12-BCL-2) or no insert (wt). 2B4 cells were cultured in RPMI 1640 supplemented with 10% fetal bovine serum, 100 U/ml penicillin, 100 ug/ml streptomycin, 10 uM non-essential amino acids and 8 ul/L betamercaptoethanol. Stably transfected 2B4 cells were isolated after transfection with pLZR-GFP retroviral vector or vector with Flag-Mc1-1 (kind gift from Joe Opferman).

Caspase Inhibition Experiment $10^6$ cells/mL Neo or BCL-2 FL5.12 cells were plated in the media containing IL-3, or $2.0 \times 10^6$ cells/mL cells were washed twice with 1×PBS and plated in media without IL-3 for 24 hours. Cells receiving caspase inhibitor were incubated with 200 µM ZVAD.fmk (Calbiochem) for 1 hour prior to any additional treatment. Cells were treated with 1 µM ABT-737 or NCE for 30 minutes, 1, 2, 3 or 4 hours as indicated and then stained with Annexin-V/PI to assess apoptotic status. For protein analysis, cells were harvested, washed with 1×PBS twice and lysates made in 1% CHAPS buffer. 10 ug was loaded onto a 10% Bis-Tris protein gel. Resulting immunoblots were probed with anti-PARP antibody (BioVision), which recognizes both cleaved and uncleaved PARP protein.

BAX Oligomerization $10^7$ freshly isolated CLL cells were incubated with DMSO, 10 nM, 100 nM, or 1 µM ABT-737 or negative control enantiomer for 4 hours, % dead assessed by Annexin-V staining and FACS analysis, then treated with 0.3% saponin and 10 µM BMH for 30 minutes on ice. Cells were then lysed, loaded onto a 10% BISTris polyacrlyamide gel, transferred, and immunoblotted for BAX.

Mice

Leukemia prone mice were generated as previously described (Letai, 2004). Mouse experimental protocols conform to the relevant regulatory standards and were approved by the Dana-Farber Cancer Institute Animal Care and Use Committee.

Statistical Analyses

Experimental replicates were performed using lysates or mitochondria from different CLL samples. In main body, where a P value is given, it was obtained by using a two-tailed Students t-test, and P<0.05 was considered statistically significant. GraphPad Prism software was used to determine EC50 values by non-linear dose-response curve fitting and to perform Mann-Whitney nonparametric testing in Table 5.

Example 2: Antiapoptotic Proteins Demonstrate Distinct Profiles of Binding Sensitizer BH3 Peptides To determine selectivity in interactions among antiapoptotic BCL-2 family members and BH3 domains of BH3-only proteins, fluorescence polarization binding assays (FPA) were used. Antiapoptotic proteins BCL-2, BCL-XL, MCL-1, BCL-w, and BFL-1 were purified from transfected bacteria as GST fusion proteins. BH3-domains were synthesized as 20-25-mers as shown in Table 2A. Oligopeptides used for FPA were tagged with an N-terminal FITC moiety. Table 2B quantitates binding by dissociation constants.

TABLE 2A

| | | |
|---|---|---|
| BID | EDIIRNIARHLAQVGDSMDR | (SEQ ID NO: 1) |
| BIM | MRPEIWIAQELRRIGDEFNA | (SEQ ID NO: 2) |
| BIDmut | EDIIRNIARHAAQVGASMDR | (SEQ ID NO: 3) |
| BAD | LWAAQRYGRELRRMSDEFEGSFKGL | (SEQ ID NO: 4) |
| BIK | MEGSDALALRLACIGDEMDV | (SEQ ID NO: 5) |
| NOXA A | AELPPEFAAQLRKIGDKVYC | (SEQ ID NO: 6) |
| NOXA B | PADLKDECAQLRRIGDKVNL | (SEQ ID NO: 7) |
| HRK | SSAAQLTAARLKALGDELHQ | (SEQ ID NO: 8) |
| BNIP | VVEGEKEVEALKKSADWVSD | (SEQ ID NO: 9) |
| PUMA | EQWAREIGAQLRRMADDLNA | (SEQ ID NO: 10) |
| BMF | HQAEVQIARKLQLIADQFHR | (SEQ ID NO: 11) |

TABLE 2B

| | BID | BIM | BIDmut | BAD | BIK | NOXA A | NOXA B | HRK | BNIP | PUMA | BMF |
|---|---|---|---|---|---|---|---|---|---|---|---|
| BCL-2 | 66 (6) | <10 | — | 11 (3) | 151 (2) | — | — | — | — | 18 (1) | 24 (1) |
| BCL-XL | 12 (9) | <10 | — | <10 | 10 (2) | — | — | 92 (11) | — | <10 | <10 |
| BCL-w | <10 | 38 (7) | — | 60 (19) | 17 (12) | — | — | — | — | 25 (12) | 11 (3) |
| MCL-1 | <10 | <10 | — | — | 109 (33) | 19 (2) | 28 (3) | — | — | <10 | 23 (2) |
| BFL-1 | 53 (3) | 73 (3) | — | — | — | — | — | — | — | 59 (11) | — |

It is immediately notable that the antiapoptotic family members may be distinguished from each other based on affinity for individual BH3 domains. For instance, BCL-XL may be distinguished from BCL-2 and BCL-w by its much greater affinity for HRK BH3. Otherwise, though there are quantitative distinctions among binding patterns of BCL-2, BCL-XL and BCL-w, the qualitative binding patterns are quite similar, suggesting similarity in the hydrophobic binding pockets of these three molecules.

In contrast with this group, MCL-1 does not bind BAD BH3, in agreement with data generated by pull-down (Opferman et al., 2003), yeast two-hybrid (Leo et al., 1999); and surface plasmon resonance (Chen et al., 2005) assays. Murine NOXA is unique among the known BH3-only proteins in that it possesses two 5 putative BH3 domains (Oda et al., 2000). It is notable that while the other four proteins interact with neither of the NOXA BH3 domains tested, MCL-1 interacts with both. This suggests that the interaction between NOXA and MCL-1 is indeed biologically significant. The ability to bind both BH3 domains suggests the possibility of novel multimeric interactions between MCL-1 and murine NOXA, or alternatively differential control over exposure of the two BH3 domains in NOXA.

Also distinct is BFL-1. While it binds BID and BIM, it binds only PUMA among the sensitizers tested. It is also notable that the activators BID and BIM BH3 are bound by all of the antiapoptotics tested, distinguishing them from the sensitizers which, except PUMA, show a more selective pattern of binding. Of additional note is that the BH3 domain obtained from BNIP-3a binds to none of the proteins tested, and does not activate BAX or BAK. While the possibility that BNIP BH3 interacts with an untested multi-domain pro- or antiapoptotic BCL-2 family member cannot be excluded, it is also possible that BNIP-3a does not function as a BH3-family member at all (Ray et al., 2000).

Example 3: Dependence on Individual Antiapoptotic Proteins May be Deduced by Pattern of Sensitivity to Sensitizer BH3 Peptides; Inhibition of Antiapoptotic Protein is Insufficient for MOMP Unless Activator TBID is Present Previous results have shown that the BH3 domains of BID and BIM possess the ability to induce BAX and BAK oligomerization and cytochrome c release in a purified mitochondrial system (Letai et al., 2002). This class is referred to as the BIB domain "activators." BH3 domains from BAD and BIK (termed "sensitizers") were unable to induce cytochrome c release on their own. However, when an activator was bound and sequestered by BCL-2, preventing interaction of the activator with BAX or BAK, sensitizers could provoke mitochondrial apoptosis by competitively inhibiting BCL-2's binding of the activator, freeing the activator to oligomerize BAX or BAK and induce cytochrome c release. Thus, the two sensitizer BH3 domains were shown to be antagonists of BCL-2 antiapoptotic function. The ability to antagonize BCL-2 function correlated with high-affinity binding to BCL-2.

In Table 2B above, the expanded range of BH3 domains tested in the present study demonstrate distinct patterns of binding to antiapoptotic proteins. To test if selective binding corresponded to ability of individual BH3 domains to selectively antagonize antiapoptotic function, a purified mitochondrial system was constructed in which the critical apoptosis decision making molecular machinery was reconstituted. For the activator function, caspase-8 cleaved BID protein, tBID, was used. tBID is an archetypical activator protein, capable of inducing BAX/BAK oligomerization and cytochrome c release in purified mitochondria (Wei et al., 2000) and synthetic liposomes (Kuwana et al., 2005; Kuwana et al., 2002). tBID's induction of cytochrome c release and apoptosis requires BAX or BAK (Cheng et al., 2001; Wei et al., 2001). The multidomain proapoptotic function was provided by the BAK which resides in mouse liver Mitochondria; mouse liver mitochondria contain no detectable BAX protein (Letai et al., 2002). The dominant antiapoptotic function was provided by one of the five different recombinant antiapoptotic proteins used in the binding assays. BH3 peptides provided the sensitizer function.

As cytochrome c release is the readout for the system, it was important to test whether the peptides by themselves release cytochrome c in mouse liver mitochondria like activators BID or BIM BH3 (Letai et al., 2002). FIG. 1A is a confirmatory assay that shows none of the sensitizer BH3 peptides by themselves can induce cytochrome c release significantly above background, even at concentrations 10-fold higher than those used in FIGS. 1B-1F. While this has previously been shown for BAD, BIK, NOXA A, and NOXA B BH3's, this is a novel finding for the HRK, BNIP, PUMA and BMF BH3 domains.

Figure 1F:
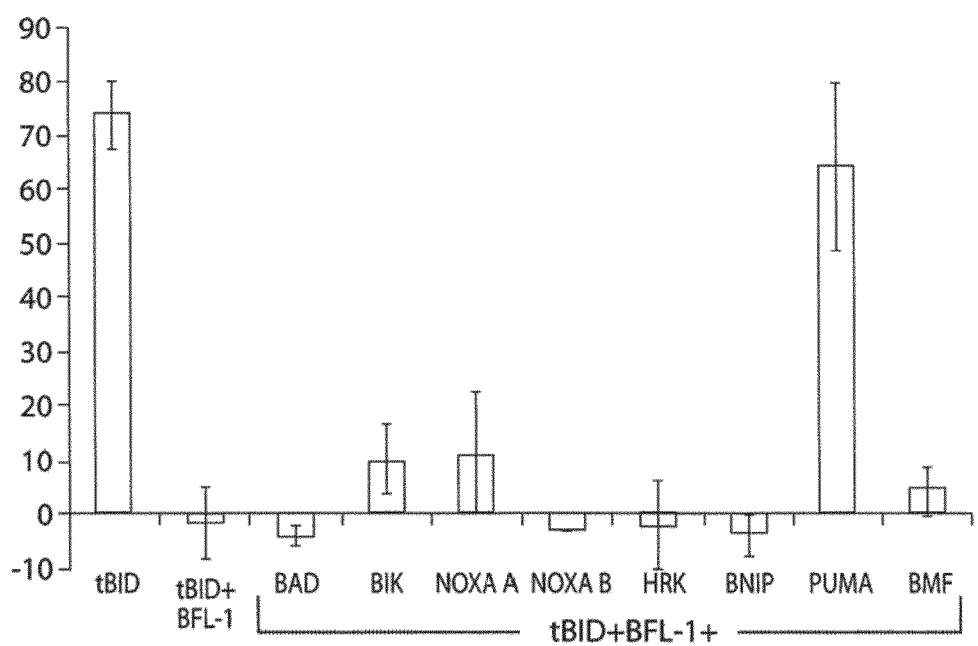
FIG. 1F is a bar chart showing the effects of tBID (first bar) and BFL-1 (2.4 uM; second bar) on cytochrome c release from mitochondria. The effect of sensitizer BH3 peptides on restoration of cytochrome c release is also shown.

In each of the subsequent panels, cytochrome c release by tBID is demonstrated, followed by inhibition of cytochrome c release by addition of either BCL-2 (FIG. 1B), BCL-XL (FIG. 1C), BCL-w (FIG. 1D), MCL-1 (FIG. 1E), or BFL-1 (FIG. 1F). The ability of the panel of BH3 domains to antagonize antiapoptotic protection as measured by cytochrome c release was determined. Remarkably, in each case, the ability to antagonize antiapoptotic function maps to the binding specificities in Table 2B. This is important confirmation that the binding pattern elucidated in Table 2B corresponds to biological function.

Figure 2:
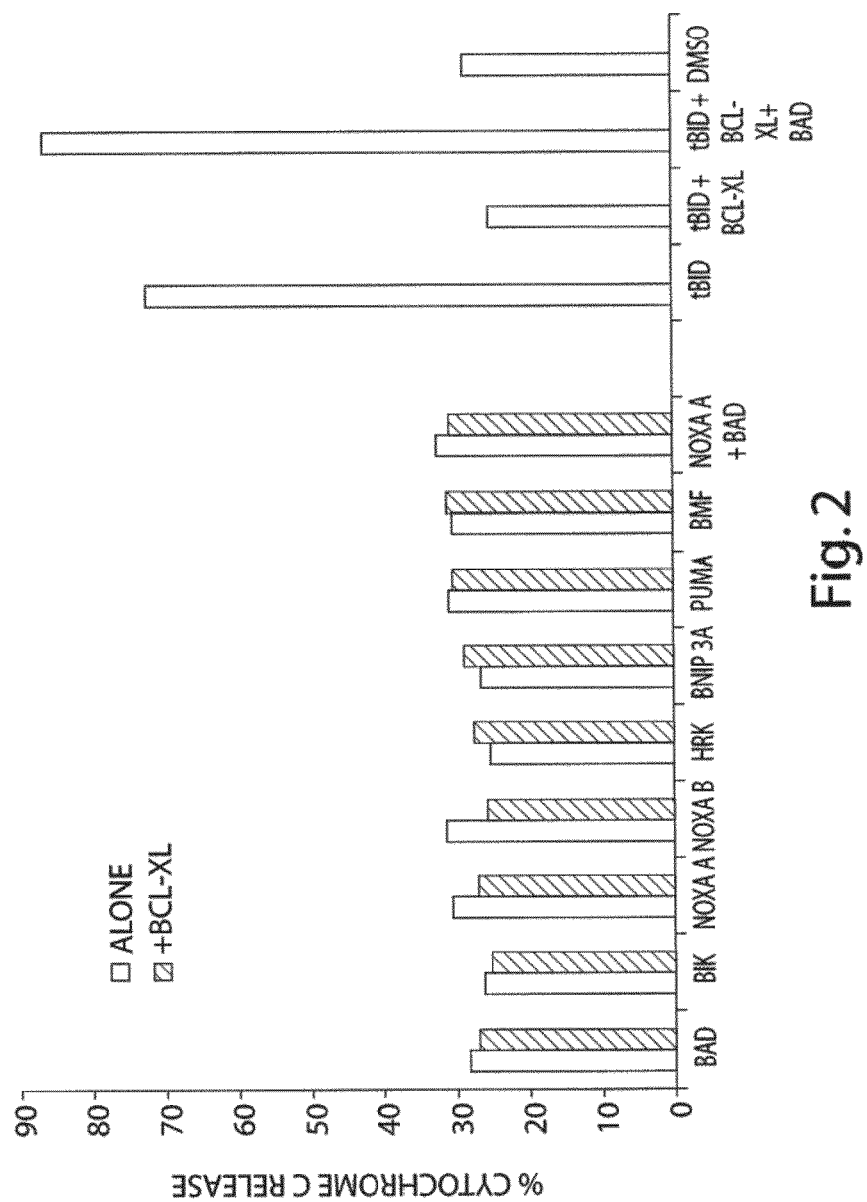
FIG. 2 is a bar chart showing the effect of BH3 peptides on cytochrome c release. MLM were treated with the indicated peptides at 10 uM in the presence or absence of 0.2 uM BCL-XL protein.

It is important to emphasize that treatment with sensitizer peptides alone, even those that bind and antagonize all the antiapoptotics tested, such as PUMA BH3, or the combination of NOXA and BAD BH3 is insufficient to cause cytochrome c release (FIG. 1A). Furthermore, when the panel of sensitizer BH3 peptides was tested in the presence of the antiapoptotic protein BCL-XL, there was still no cytochrome c release, formally ruling out the possibility that the BH3 peptides were somehow directly converting antiapoptotic proteins to a proapoptotic function (FIG. 2). To induce MOMP and cytochrome c release, there appears to be an absolute requirement for an activator function, here provided by the tBID protein.

These data critically demonstrate that the panel of peptides can determine whether a mitochondrion depends on an antiapoptotic protein to maintain integrity. Furthermore, the identity of the critical antiapoptotic protein can be deduced based on the pattern of sensitivity to the panel of sensitizer BH3 peptides. This strategy is termed BH3 profiling.

Example 4: Sensitizers Displace Activators from Antiapoptotic Proteins

Figure 3A:
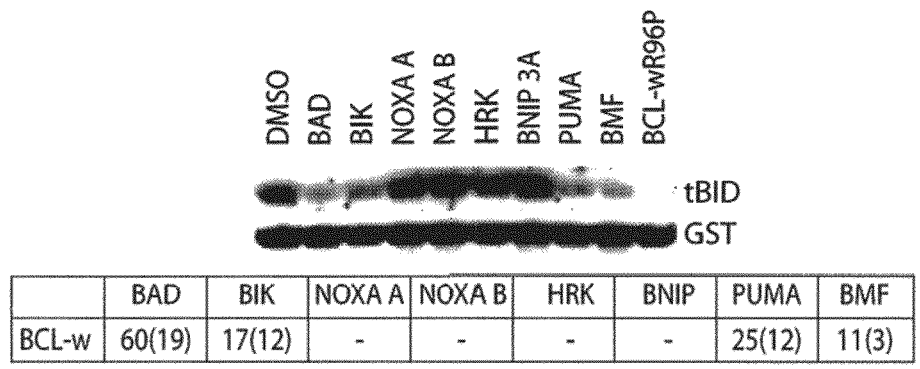
FIG. 3A is a photograph of a Western blot showing the results of a GST-pulldown assay in which GST-BCL-w (or point mutant R96P) was combined with tBID protein and the indicated BH3 peptides (10 μM). The BH1 domain R96P mutant of BCL-w lacks the ability to bind BH3 domains. For convenience, BCL-w binding pattern from Table 2B is excerpted below.
Figure 3B:
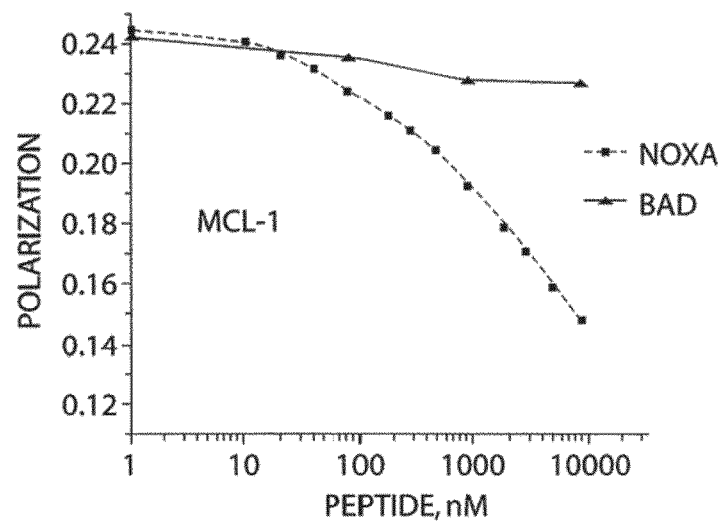
FIG. 3B and FIG. 3C are line graphs showing the effects of BAD and NOXA BH3 peptides on displacement of a fluorescein tagged BIM BH3 peptide from BCL-2 and MCL-1 proteins by fluorescence depolarization. Shown are representative plots from three independent experiments for each combination.
Figure 3C:
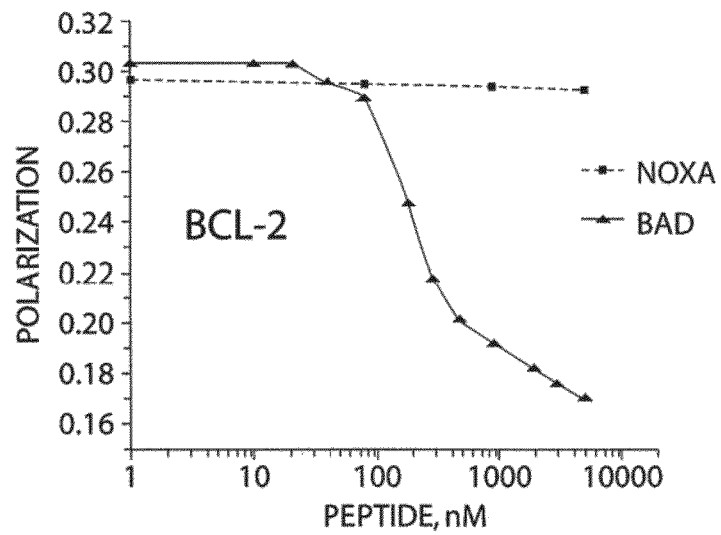

Since sensitizer BH3 peptides cannot induce cytochrome c release on their own, but can induce cytochrome c release when activator and antiapoptotic proteins are present, in a pattern that mirrors their binding to antiapoptotic proteins, it was hypothesized that the sensitizers are displacing activators from the antiapoptotic proteins. As one test of this hypothesis, the ability of sensitizer peptides to displace tBID from antiapoptotic protein Bcl-w was examined utilizing a GST-pulldown assay. Proteins bound to glutathioneagarose beads were eluted with glutathione and analyzed by Western blot. In FIG. 3A, tBID is displaced from BC1-w by sensitizer BH3 peptides in a pattern that replicates the pattern in FIG. 1D. As an additional test, the displacement of the activator BIM BH3 peptide from BCL-2 and MCL-1 by BAD and NOXA BH3 peptides was determined. In FIG. 3B, consistent with Table 2B, BAD BH3 efficiently displaces BIM BH3 from BCL-2, but not MCL-1, whereas NOXA A BH3 7 efficiently displaces BIM from MCL-1, but not BCL-2. These experiments support the ability of sensitizer BH3 peptides to displace activators from the antiapoptotic binding cleft.

Figure 4A:
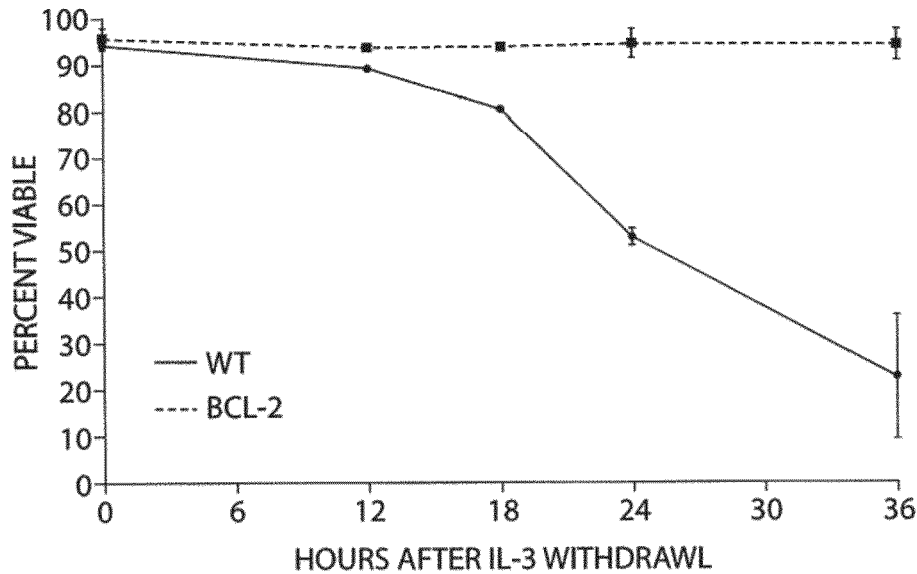
FIG. 4A is a line graph showing the effects of IL-3 withdrawal on the survival of wtFL5.12 and FL5.12-BCL-2 cells. Survival was imputed for cells not staining with Annex in V by FACS analysis. Shown is average and standard deviation of three independent experiments.

Example 5: A Cellular Requirement for BCL-2 Corresponds to a "BCL-2 Pattern" of Mitochondrial Sensitivity to the Sensitizer BH3 Panel In order to test whether mitochondrial dependence on individual antiapoptotic protein function can be correlated with cellular behavior, cellular models of defined antiapoptotic dependence were investigated. First, it was determined if cellular requirement for BCL-2 for cellular survival correlates with the BCL-2 signature of mitochondrial sensitivity to sensitizer BH3 domains found in FIG. 1B. The prolymphocytic murine FL5.12 cell line requires IL-3 to maintain survival. Apoptosis induced by IL-3 withdrawal is inhibited by overexpression of BCL-2 (FIG. 4A). Therefore, BCL-2-overexpressing FL5.12(FL5.12-BCL-2) cells deprived of IL-3 are a model of BCL-2 dependent survival. FL5.12-BCL-2 cells grown in the presence of IL-3 are examples of BCL-2 independent cells.

Figure 4B:
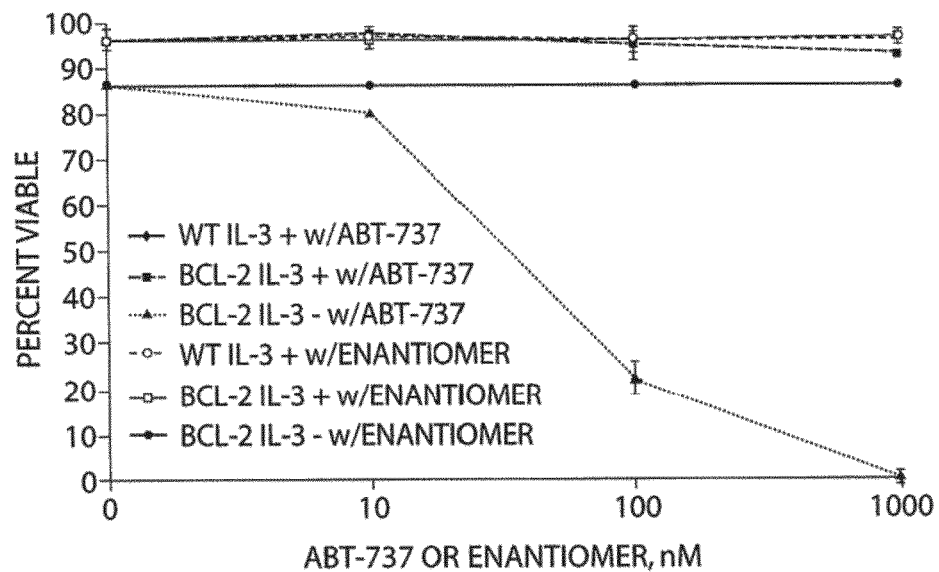
FIG. 4B is a line graph showing the effects of ABT-737, a BCL-2 antagonist, on the survival of IL-3 replete and IL-3 starved FL5.12-BCL-2 cells. Viability was assayed by absence of Annex in V staining. Shown is average and standard deviation of three independent experiments.
Figure 4C:
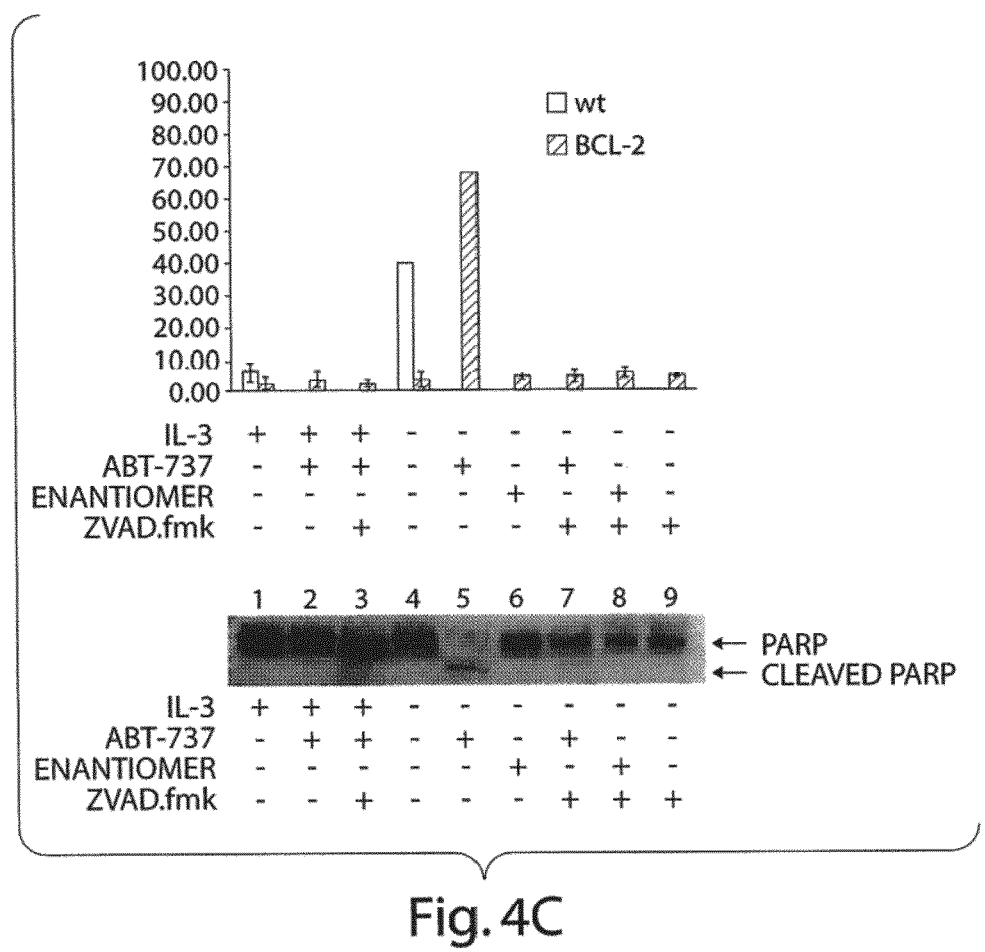
FIG. 4C is a bar chart showing the effects of ABT-737 and ZVAD.fmk on the survival of FL5.12 cells (top). Also, a photograph of an immunoblot shows the effect of ABT-737 on PARP cleavage (bottom).

While the dependence on BCL-2 of IL-3 deprived FL5.12 cells is demonstrated genetically in FIG. 4A, the dependence was confirmed using a cell-permeable BCL-2 antagonist. ABT-737 has been shown to antagonize BCL-2 (and BCL-XL and BCL-w) (Oltersdorf et al., 2005). In agreement with the prior report, ABT-737 induced cell death in the IL-3 starved, but not the IL-3 replete BCL-2 protected cells (FIG. 4B). Moreover, ABT-737 was non-toxic to the unstressed IL-3 replete wt FL5.12 cells. This cell death was caspase dependent, demonstrating that death occurred using the apoptotic pathway (FIG. 4C). IL-3-cells were grown in the absence of IL-3 for 24 hours prior to initiation of treatment with compound. All cells were treated with compounds for 24 hours prior to harvest.

Figure 5:
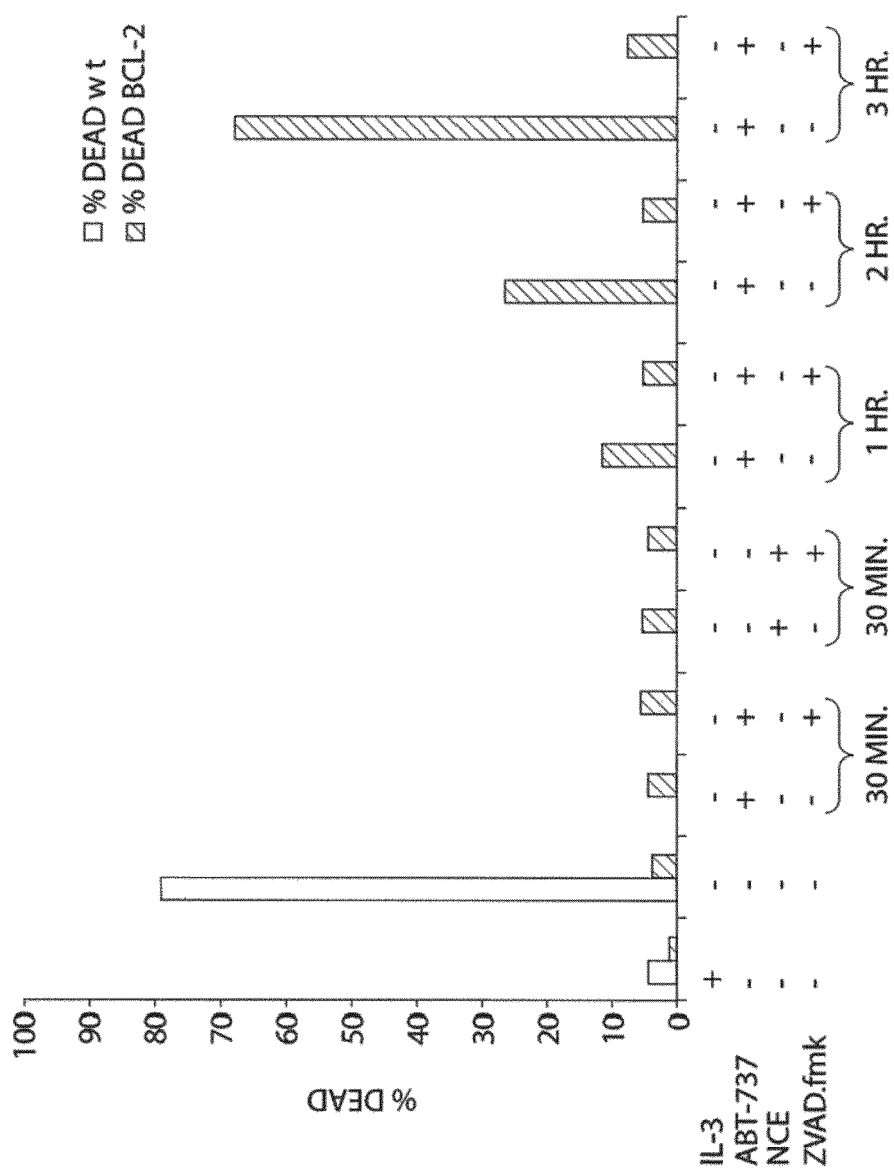
FIG. 5 is a bar chart showing the effect of ABT-737 and ZVAD.fmk on FL5.12 viability. FL5.12 were grown either with IL-3 or in the absence of IL-3 for 24 hours, then treated as indicated for either 30 minutes or 1, 2, or 3 hours. Cell death was measured by Annexin V staining via FACS analysis.

Having credentialed a BCL-2 dependent cellular system, it was next determined if BCL-2 dependence could be isolated at the level of mitochondria. It was hypothesized that removal of IL-3 would "load" the BCL-2 on the mitochondria with activator BH3 proteins. It was further hypothesized that mitochondria bearing "loaded" BCL-2 would release cytochrome c when treated with sensitizer BH3 peptides which compete for the BCL-2 binding cleft. ABT-737 inhibition of BCL-2 in FL5.12-BCL-2 cells primed by IL-3 withdrawal induced an apopiosis that is caspase dependent and very rapid (FIG. 5). The interpretation that the IL-3 starved FL5.12-BCL-2 cells were "primed" for death is supported by the rapidity of their death following ABT-737 treatment (FIG. 5).

Figure 6A:
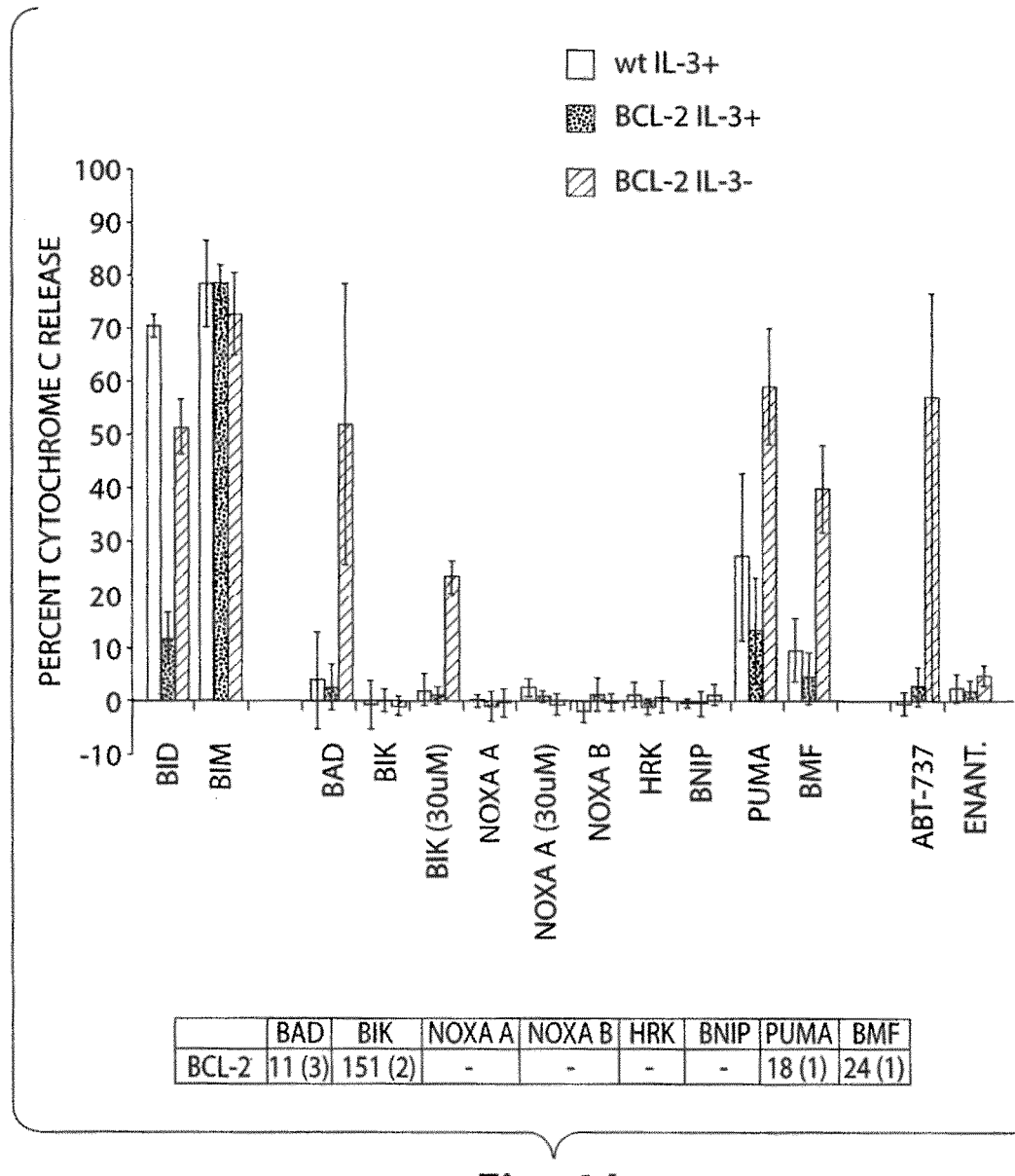
FIG. 6A is a bar chart showing the effects of BH3 peptides (10 uM) on cytochrome c release from mitochondria isolated from wtFL5.12 cells grown in the presence of IL-3 (no fill bars); FL5.12-BCL-2 cells grown in the presence (speckled bars) or absence (slashed bars) of IL-3 for 24 hours. Shown is average and standard deviation of three independent experiments. For convenience, BCL-2 binding pattern from Table 2B is excerpted below.
Figure 6B:
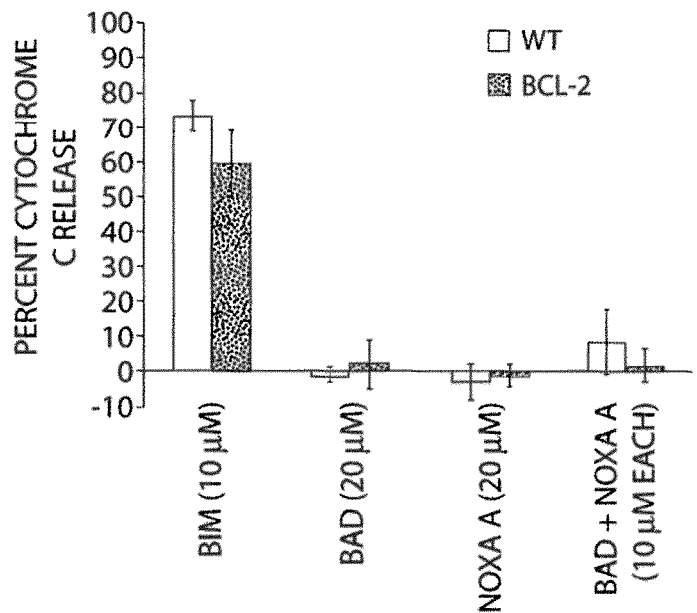
FIG. 6B is a bar chart showing the effects of NOXA and BAD BH3 on cytochrome c release from mitochondria isolated from wt and BCL-2 FL5.12 cells grown in the presence of IL-3. Shown is average and standard deviation of three independent experiments.
Figure 6C:
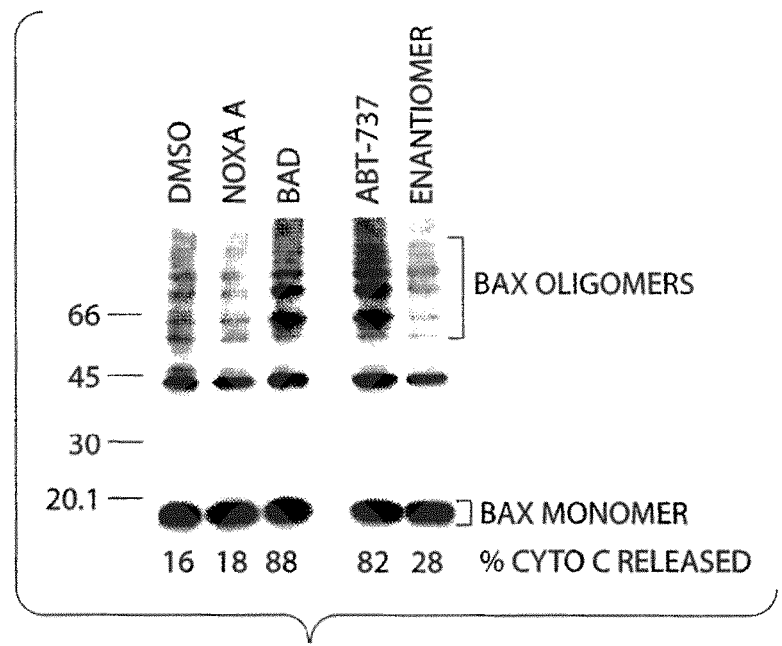
FIG. 6C is a photograph of a Western blot depicting the effects of NOXA A, BAD, ABT-737, or control enantiomer on cytochrome c release from FL5.12 cells grown in the absence of IL-3 for 24 hours.

Mitochondria were isolated from wt FL5.12 cells and FL5.12-BCL-2 cells in the presence of IL-3, and from FL5.12-BCL-2 cells following 24 hours of IL-3 deprivation. Due to advanced apoptosis, mitochondria could not be isolated in sufficient quantities from wt FL5.12 cells after IL-3 deprivation. FIG. 6A shows that while activators BID and BIM potently induce cytochrome c release from mitochondria isolated from wt FL5.12 cells, the remaining sensitizer peptides do not (blue bars). Thus, inhibition of antiapoptotic family members is by itself not sufficient to induce MOMP. Next, BCL-2 overexpression inhibits release induced by 10 μM BID BH3, but not 10 μM BIM BH3, in accordance with dose-response curves previously demonstrated (red bars) (Letai et al., 2002). When mitochondria from FL5.12-BCL-2 cells deprived of IL-3 were tested, however, certain sensitizer peptides demonstrated the ability to induce cytochrome c release (tan bars), and sensitivity to 10 μM BID BH3 is restored. It is most notable that only those sensitizer peptides with high affinity for BCL-2 cause MOMP. BIK BH3 does not induce cytochrome c release in this setting, but it should be noted that it has approximately 10-fold lower affinity than BAD, PUMA or BMF BH3 for BCL-2. It can be seen, therefore, that cellular BCL-2 dependence can be "diagnosed" from the pattern of mitochondrial sensitivity to the panel of sensitizer BH3 peptides. This dependence can be "diagnosed" whether the activator involved is a recombinant protein, as in FIG. 1, or a more complex mix involving more than one molecule, as is likely the case following IL-3 withdrawal. Note that inhibition of BCL-2 alone is not sufficient to induce cytochrome c release, as seen by the failure of all of the sensitizer peptides to induce release in the IL-3 replete FL5.12-BCL-2 mitochondria (FIG. 6A). In fact, even the combination of peptides, BAD and NOXA BH3, which provide a broad spectrum of antiapoptotic protein binding, cannot induce cytochrome c release in the absence of an activator molecule (FIG. 6B). To induce MOMP, the BCL-2 must first be "primed" by molecules communicating a death signal, generated by IL-3 withdrawal. Mitochondria isolated from FL5.12-BCL-2 cells grown in the absence of IL-3 for 24 hours were treated with NOXA A or BAD peptides (30 uM) or ABT-737 or control enantiomer at 10 uM for 35 minutes. Mitochondrial pellets were subjected to chemical crosslinking as previously described (Letai et al., 2002). BCL-2 blocks apoptosis upstream of BAX oligomerization, and BAD BH3 and ABT-737 inhibition of BCL-2 on IL-3 starved mitochondria results in BAX oligomerization (FIG. 6C). Therefore, it was hypothesized that this death signal might be an activator BH3 protein.

Figure 6D:
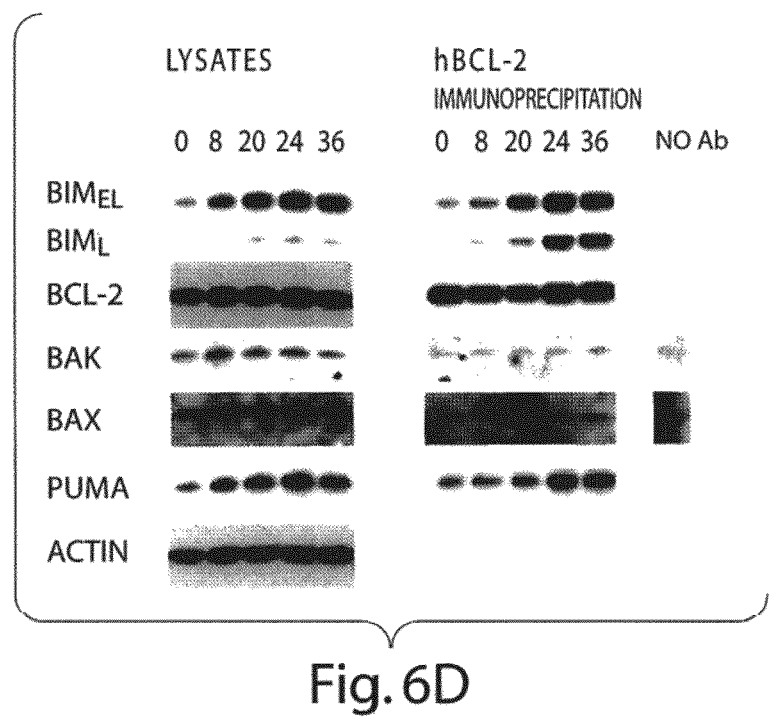
FIG. 6D shows photographs of immunoblots depicting the effects of IL-3 withdrawal on BIM levels in FL512-BCL-2 whole cell lysates (left) and samples immunoprecipitated by an antibody directed against the human BCL-2 transgene product (right). Numbers at top refer to hours after IL-3 withdrawal. Control lane performed without antihuman BCL-2 antibody in pulldown at right.

BIM has previously been shown to play a role in death following IL-3 withdrawal in FL5.12 cells (Harada et al., 2004). FIG. 6D shows that total cellular BIM levels, as well as levels of BIM complexed to BCL-2, dramatically increase following IL-3 withdrawal. It is notable that levels of BCL-2, BAX, and BAK stay roughly constant during the same time period. These results suggest that the activator BIM (and perhaps PUMA) is a dynamic mediator of the death response following IL-3 withdrawal in FL5.12 cells, and that it is sequestered to prevent apoptosis. Cells and mitochondria bearing "loaded" BCL-2 are then "addicted" to BCL-2, and die when BCL-2 function is antagonized. Furthermore, cellular BCL-2 addiction can be diagnosed by the pattern of mitochondrial sensitivity to sensitizer BH3 domains. The negative control of immunoprecipitation using anti-human BCL-2 antibody on lysates from IL-3 starved FL5.12-BCL-XL cells yielded no bands, not shown.

Figure 6E:
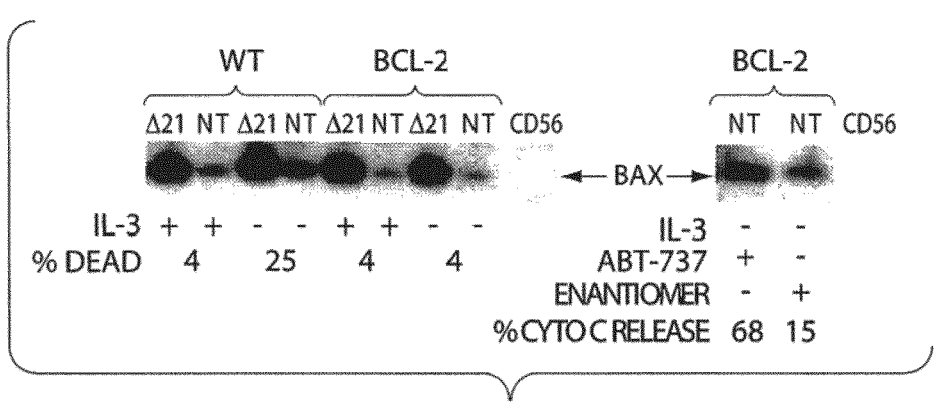
FIG. 6E is a photograph of a Western blot showing the results of an immunoprecipitation assay. BAX was immunoprecipitated using an antibody recognizing all BAX conformations (Δ21) or only the activated conformation with N-terminal exposure (NT). Death induced in the cells is indicated below. At right, mitochondria isolated from IL-3 starved cells were treated with ABT-737 or control enantiomer, and immunoprecipitation with NT performed as indicated. CD56 indicates control immunoprecipitation by an irrelevant antibody recognizing CD56.

This model predicts that BCL-2 acts upstream of BAX activation by intercepting activator BH3 molecules. To test this prediction, in FIG. 6E, immunoprecipitation was performed with an antibody that recognizes only the activated form of BAX which exposes an N-terminus epitope (Desagher ct al., 1999; Hsu and You le, 1997). wt or BCL-2 expressing FL5.12 cells were exposed to IL-3 withdrawal as indicated. IL-3 withdrawal induced BAX activation in wt FL5.12 cells, while total BAX levels remained constant. However, when BCL-2 protected against death from IL-3 withdrawal, it also prevented BAX conformational change, consistent with BCL-2's sequestering activators like BIM prior to their interaction with BAX (compare fourth and eight lanes). Furthermore, treatment with ABT-737 restored cytochrome c release and BAX activation, consistent with ABT-737 functioning by displacing activators from BCL-2. Taken together, these results indicate that BCL-2 blocks apoptosis upstream of BAX activation.

Figure 7A:
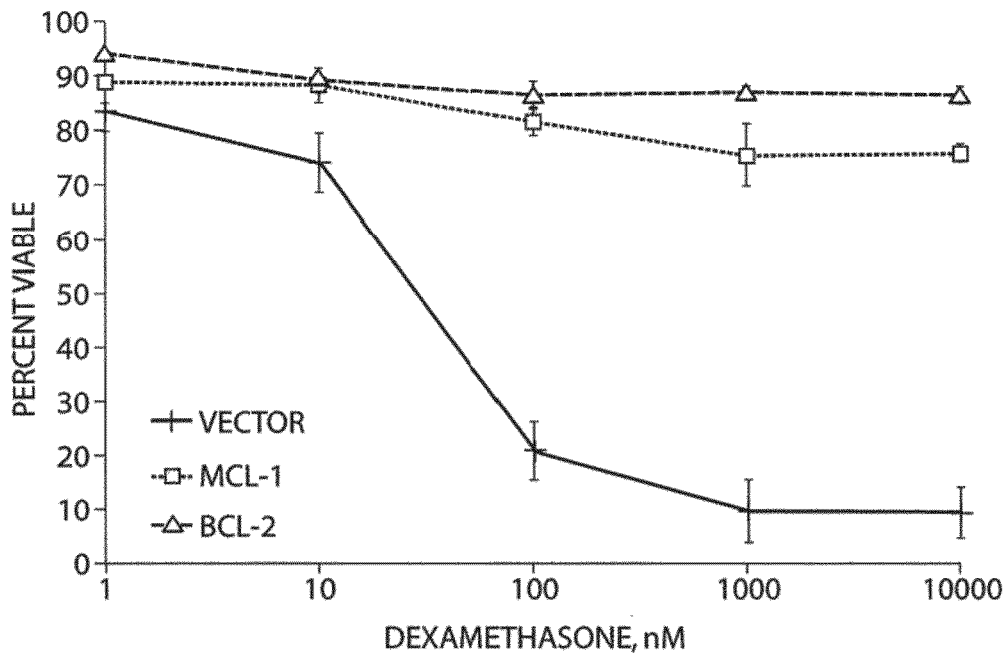
FIG. 7A is a line graph showing the effects of MCL-1 and BCL-2 on cell death induced by dexamethasone in 2B4 cells. Viability determined by absence of Annexin V staining by FACS. Shown is average and standard deviation of three independent experiments.
Figure 7B:
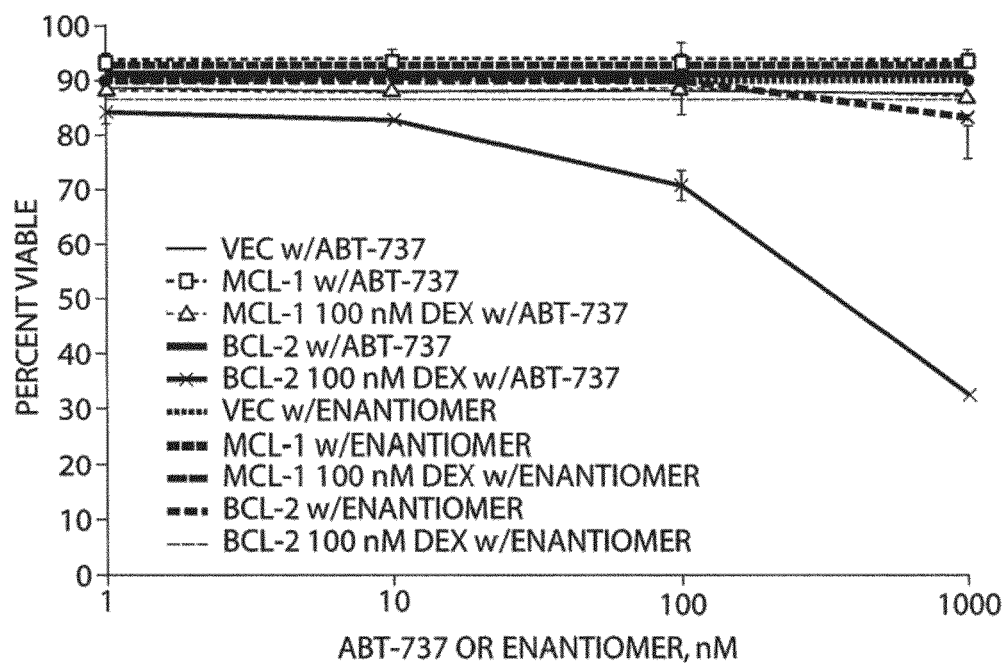
FIG. 7B is a line graph showing the effects of BCL-2 antagonist ABT-737 on MCL-1 dependent 2B4 cells and BCL-2 dependent 2B4 cells. Shown is average and standard deviation of three independent experiments.

Example 6: BH3 Profiling can Discriminate MCL-1 Cellular Dependence from BCL-2 Cellular Dependence To test if the model of antiapoptotic "priming" could be extended beyond BCL-2 to other antiapoptotic proteins, the behavior of cells protected by BCL-2 was compared to those protected by MCL-1. 2B4 cells transfected with Flag-MCL-1, BCL-2, or empty vector constructs were cultured for 24 hours in the presence of the indicated concentration of dexamethasone. The murine hybridoma 2B4 cell line is sensitive to dexamethasone treatment. Overexpression of FLAGtagged MCL-1 or BCL-2 confers resistance to dexamethasone-induced apoptosis (FIG. 7A). Therefore, dexamethasone-treated, FLAG-MCL-1 expressing cells are a model of cellular MCL-1 dependence, while dexamethasone-treated, BCL-2 expressing cells are a model of cellular BCL-2 dependence. 2B4 cells were incubated with dexamethasone and either ABT-737 or enantiomer for 24 hours. Treatment of the MCL-1-protected dexamethasone-treated cells with ABT-737 has no effect, showing the cells are not dependent on BCL-2 for survival. In stark contrast, 2B4 cells protected from dexamethasone-induced apoptosis by BCL-2 are very sensitive to ABT-737 (FIG. 7B).

Figure 7C:
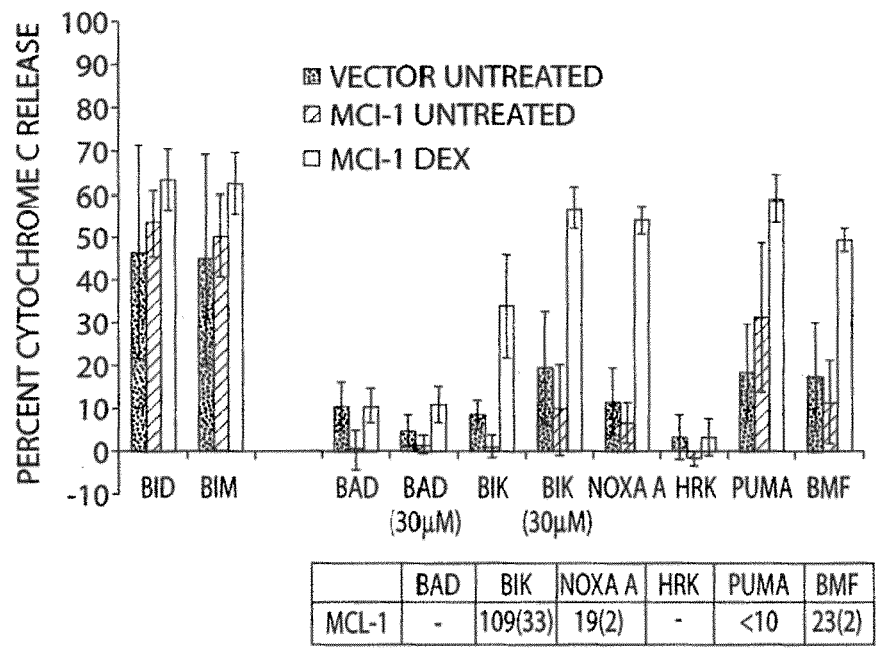
FIG. 7C is a bar chart showing the effects of BH3 peptides on cytochrome c release from mitochondria isolated from MCL-1-expressing 2B4 cells treated as indicated. Shown is average and standard deviation of three independent experiments. For convenience, MCL-1 binding pattern from Table 2B is excerpted below.
Figure 7D:
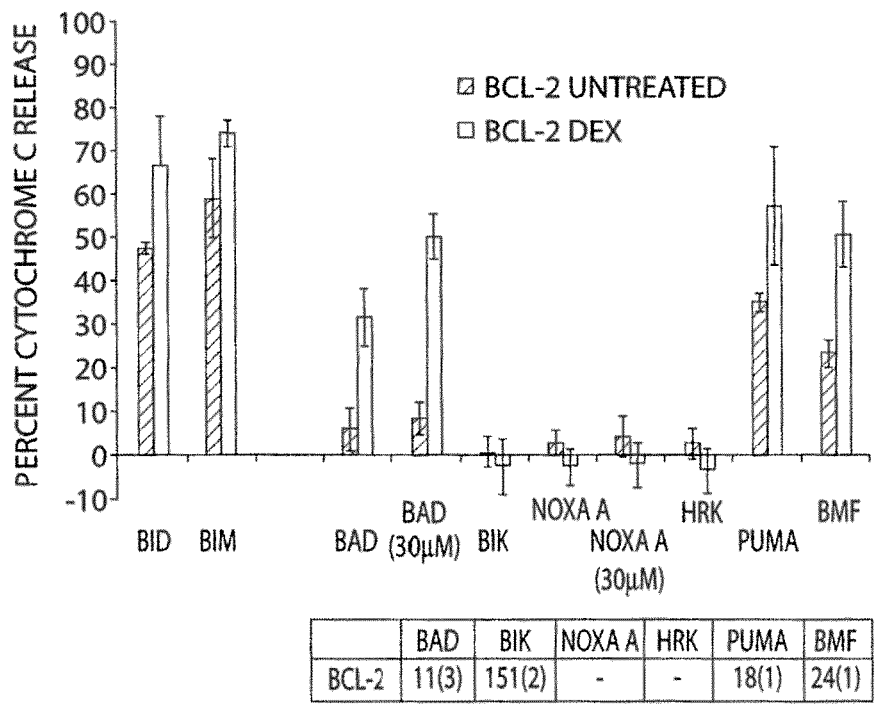
FIG. 7D is a bar chart showing the effects of BH3 peptides on cytochrome c release from mitochondria isolated from BCL-2-expressing 2B4 cells treated as indicated. For convenience, BCL-2 binding pattern form Table 2B is excerpted below.

The cellular data provoke the prediction that mitochondria isolated from 2B4-MCL-1 cells treated with dexamethasone would be sensitive to NOXA and insensitive to BAD BH3, the opposite of the pattern observed with IL-3-starved FL5.12-BCL-2 cells. Mitochondria were isolated from dexamethasone-treated and untreated vector-transfected and FLAG-MCL-1-transfected 2B4 cells. Apoptosis was too advanced to permit isolation of mitochondria from dexamethasone treated vector-transfected 2B4 cells. As can be seen in FIG. 7C, only mitochondria isolated from the MCL-1 dependent cells recapitulate an "MCL-1 pattern" of sensitivity to sensitizer BH3 peptides. As with the FL5.12 cells, since sensitizer BH3 peptides cause little cytochrome c release in untreated cells, it is clear that sensitizer BH3 peptide inhibition of MCL-1 (and other antiapoptotic proteins that might be present) is not by itself sufficient to induce apoptosis. An additional death signal (initiated by dexamethasone treatment in this case) is needed to "prime" MCL-1 so that MCL-1 antagonism by sensitizers results in mitochondrial penneabilization. To demonstrate the robustness of this strategy, BH3 profiling was performed on 2B4 cells treated with dexamethasone, but this time protected with BCL-2. Consistent with the priming model, a BCL-2 pattern is revealed (FIG. 7D). Thus, MCL-1 dependence, like BCL-2 dependence, also can be "diagnosed" by mitochondrial sensitivity to the sensitizer BH3 panel.

Figure 7E:
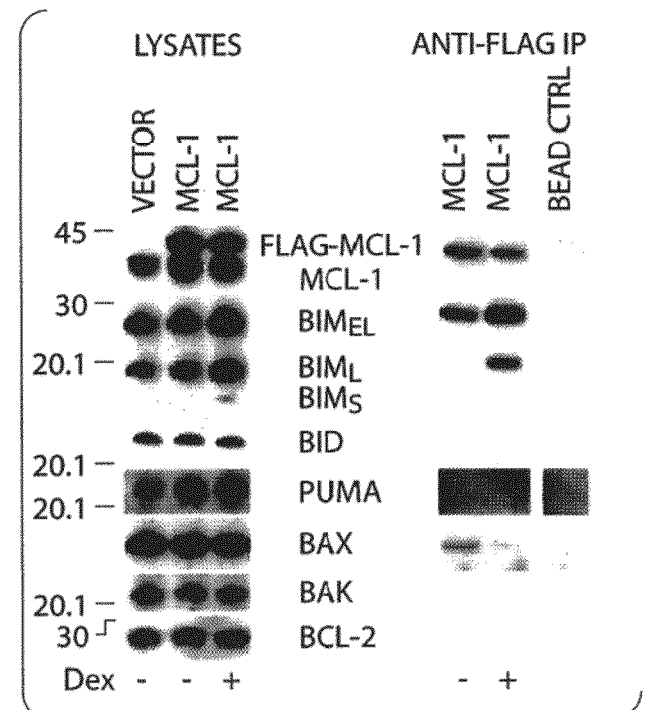
FIG. 7E is a photograph of an immunoblot showing the effects of dexamethasone on FLAG-MCL-1 transfected 2B4 cells. FLAG antibody linked to agarose beads immunoprecipitated proteins complexing with FLAG-MCL-1. Increased BIM sequestration by MCL-1 correlates with MCL-1 dependence.
Figure 7F:
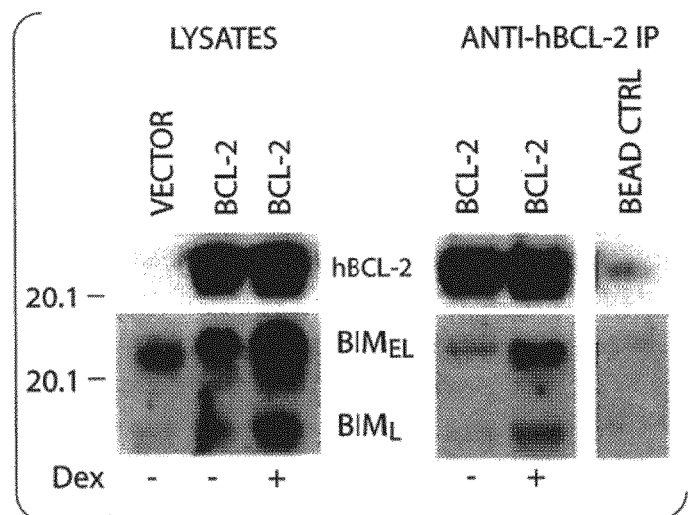
FIG. 7F is a photograph of an immunoblot showing the effects of dexamethasone on FLAG-BCL-2 transfected 2B4 cells.

As with the FL5.12cells, it was determined if dexamethasone treatment resulted in increased sequestration of an activator BH3 protein by MCL-1 and BCL-2. Vector or FLAG-MCL-1 transfected 2B4 cells were treated with 0 or 100 nM dexamethasone and lysed. FIG. 7E shows that FLAG-MCL-1 sequesters increased amounts of BIM following the death signaling induced by dexamethasone treatment, as does BCL-2 (FIG. 7F). Note that levels of BAX and BAK stay constant during the treatment. Also note that it appears that the small amount of BAX bound to cells before treatment with dexamethasone decreases after treatment. One interpretation is that the BAX is displaced by increased levels of BIM binding to BCL-2. This is significant because it suggests that displacement of BAX from MCL-1 is insufficient to induce MOMP and death.

Figure 7G:
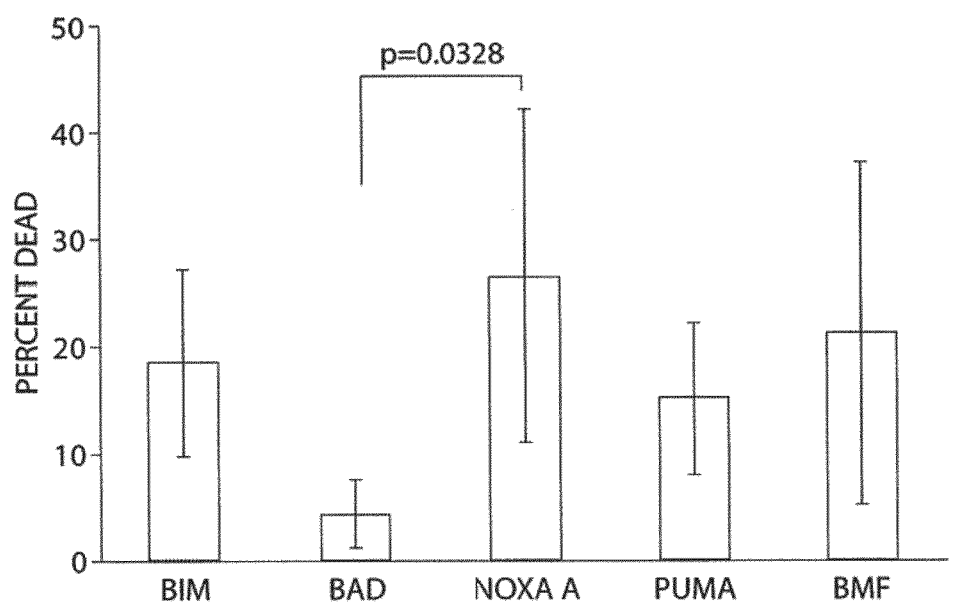
FIG. 7G is a bar chart showing the effects of BH3 peptides on dexamethasone-treated FLAG-MCL-1 2B4 cells. Primed FLAG-MCL-1 2B4 cells transfected with BH3 peptides illustrate an MCL-1 pattern.

To further demonstrate that the mitochondrial assays reflect true cellular dependence, peptides were transfected via electroporation into FLAG-MCL-1-transfected 2B4 cells that had been treated with dexamethasone, putatively priming MCL-1 with death signals, carried at least in part by BIM. Percent killing was ascertained by Annexin-V staining. Note that killing by transfection with NOXA A is significantly greater than that with BAD, recapitulating the same MCL-1 pattern observed in isolated mitochondria from this same cell line (FIG. 7G, compare with Table 2B, FIG. 1E, FIG. 7C). N=3 and the error bars represent the standard deviation. These results support the cellular relevance of the mitochondrial BH3 profiling assays.

Example 7: Dependence on BCL-2 in a Leukemia Corresponds to Mitochondrial Sensitivity to Sensitizers in a "BCL-2 Pattern" and Sequestration of BIM Dependence on antiapoptotic proteins is perhaps of greatest importance in the context of cancer, in which antiapoptotic BCL-2 family proteins are subjects of intense investigation as therapeutic targets. While the concept of oncogene addiction has received attention recently (Jonkers and Berns, 2004; Weinstein, 2002), the molecular details of the addiction to specific oncogenes is poorly understood. A validated model of oncogene addiction, a BCL-2 dependent murine leukemia, was used to examine the molecular basis for BCL-2 "addiction."

Previous results have described a mouse acute lymphocytic leukemia model in which c-myc is constitutively expressed and human BCL-2 is repressibly expressed. In this model, when BCL-2 transgene expression is eliminated by administration of doxycycline, the leukemic cells undergo apoptosis, resulting in rapid resolution of the leukemia (Letai, 2004). This provides an ideal in vivo model of a BCL-2 dependent cancer. It was hypothesized that dependence on BCL-2 was due to a similar mechanism to that of the IL-3 deprived FL5.12-BCL-2 cells—that is, a death signal was being initiated and carried by an activator BH3 molecule, but BCL-2 was binding it and preventing its interaction with multidomain proapoptotic proteins.

Figure 8A:
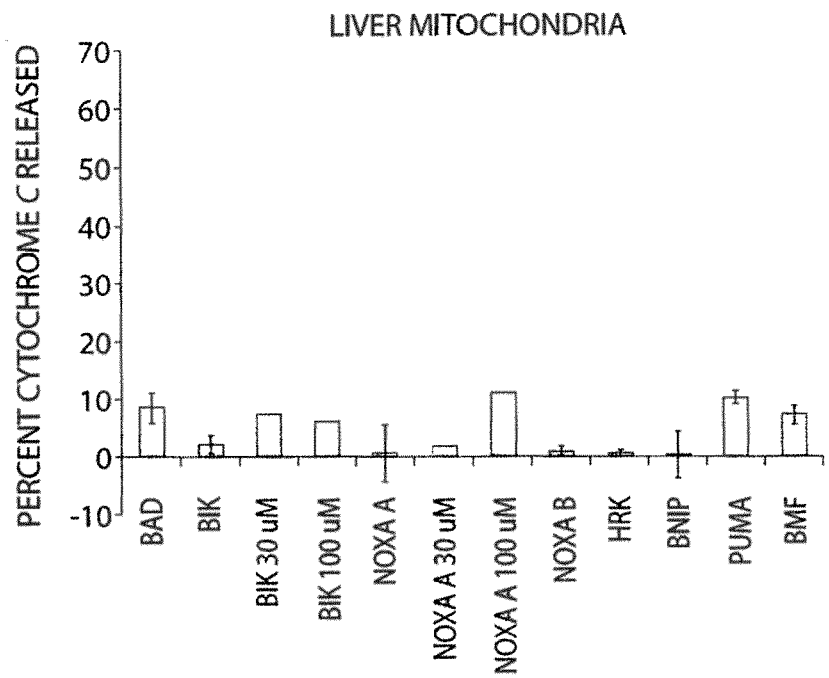
FIG. 8A is a bar chart showing the effects of BH3 peptides (10 µM, unless otherwise noted) on cytochrome c release from mitochondria isolated from liver.
Figure 8B:
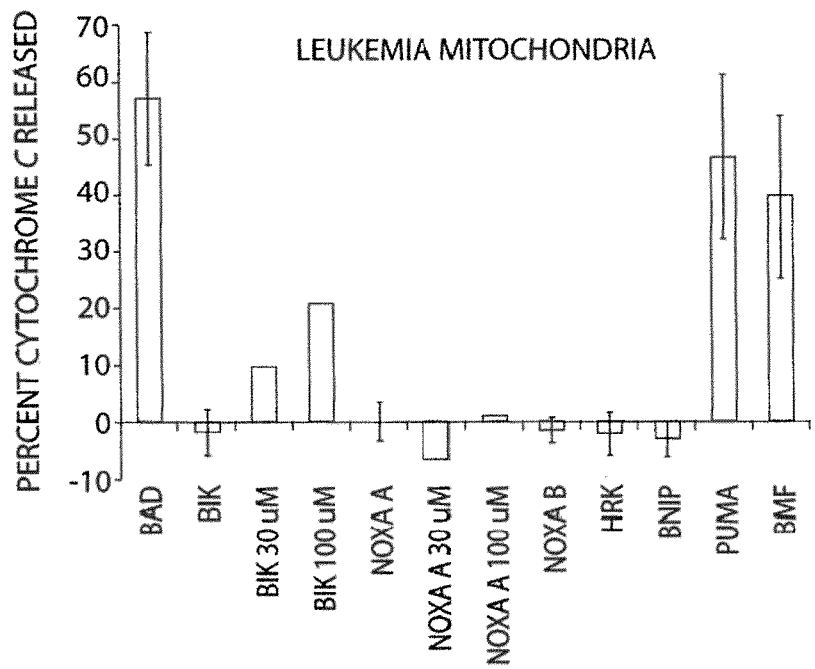
FIG. 8B is a bar chart showing the effects of BH3 peptides on cytochrome c release from mitochondria isolated from BCL-2-dependent leukemia. For convenience, BCL-2 binding pattern from Table 2B is excerpted below. Shown is average and standard deviation of three independent experiments, except 30 and 100 µM treatments which were performed once.

Mitochondria were isolated from leukemia cells and exposed to sensitizer BH3 peptides. Subsequently, cytochrome c release was measured. As an internal control, mitochondria were isolated from liver from the leukemic mice in parallel (FIG. 8A). The sensitizer BH3 peptides were unable to induce cytochrome c release from non-malignant hepatocyte mitochondrias from the leukemic mice, just as they were unable to induce cytochrome c release from non-malignant liver mitochondria from normal mice (FIG. 1A) or from non-malignant FL5.12 (FIG. 6A) or 2B4 mitochondria (FIG. 7C). Intriguingly, certain sensitizer BH3 peptides were capable of inducing near total cytochrome c release from the leukemic mitochondria (FIG. 8B). Significantly, the pattern of peptides which induced release corresponded exactly to those peptides which bind with high affinity to BCL-2 (Table 2B), namely BAD, BIK, PUMA, and BMF. Note that, consistent with its approximately ten-fold lower affinity than BAD BH3 for BCL-2, BIK BH3 requires a ten-fold higher concentration to demonstrate cytochrome c release. A ten-fold increase in NOXA A peptide concentration has no effect, consistent with the extremely low affinity NOXA A has for BCL-2.

Figure 8C:
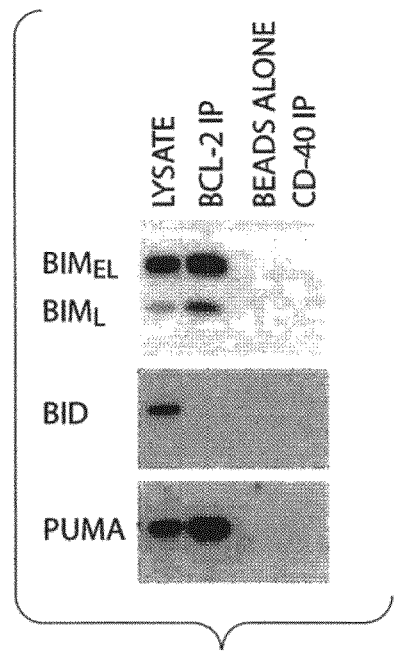
FIG. 8C is a picture of an immunoblot of samples from a BCL-2 dependent leukemia. First lane shows a whole cell lysate, 25 ug loaded; second lane—products of an immunoprecipitation using an antibody against the human BCL-2 transgene product; third lane—a control with Protein A beads alone; fourth lane—control immunoprecipitation using an irrelevant hamster monoclonal antibody recognizing murine CD-40.

These results suggest that in this leukemia model, death signals are being continually initiated, and BCL-2 is required to sequester the activator BH3 molecule to prevent apoptosis. In contrast to the non-malignant systems tested above, leukemic cell BCL-2 behaves as if already "primed" with activator protein(s) without any further intervention, such as growth factor withdrawal or dexamethasone treatment. FIG. 8C shows that BIM is expressed in the leukemia cells, and it is bound by BCL-2. Supporting the signal importance of BIM in transmitting death signals in this model, BID is also present in the lysate, but is not bound by BCL-2. Note that PUMA is also found to be bound by BCL-2, consistent with a report showing PUMA deficiency could accelerate myc-induced lymphomagenesis (Hemann et al., 2004). Since the PUMA BH3 lacks the ability to directly activate BAX or BAK, it was hypothesized that PUMA is acting as a sensitizer in this context, in effect decreasing the amount of BCL-2 available to bind BIM and possibly BAX or BAK.

If BCL-2 maintains survival of this leukemia cell primarily by sequestering BIM, then one would predict that BIM loss of function could substitute for BCL-2 overexpression to cooperate with c-myc in leukemogenesis. In fact, this experiment has already been performed. It was found that BIM deficiency can indeed cooperate with c-myc to produce a pre-B lymphocytic leukemia like the one produced here by the cooperation of BCL-2 overexpression with c-myc (Egle et al., 2004). These results support a model in which BCL-2 is necessary for survival of leukemia largely because it is required to sequester BIM, preventing activation of BAX/BAK and subsequent MOMP. The leukemia cells are therefore neither normal and healthy, nor dead, but rather primed for death.

Example 8: BH3 Profiling Predicts Sensitivity to ABT-737

Figure 8D:
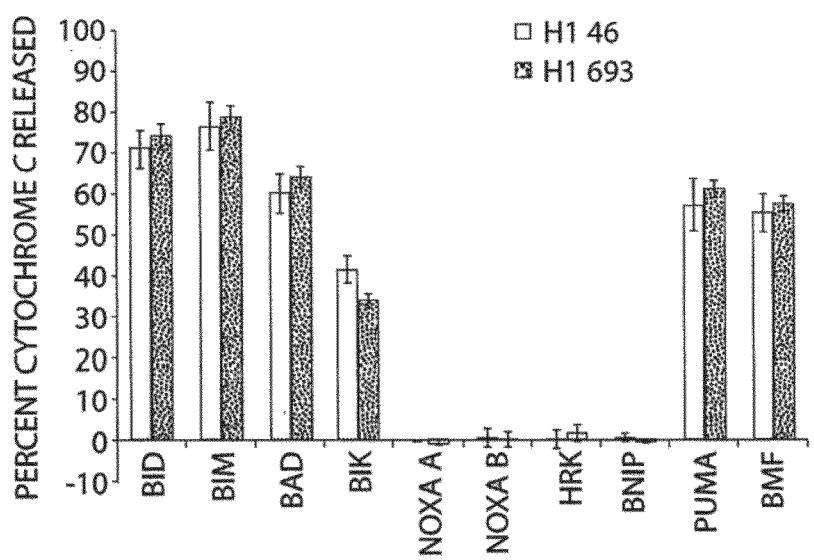
FIG. 8D is a bar chart showing the effects of BH3 peptides on cytochrome c release from mitochondria isolated from two SCLC cell lines, H146 and H1963. N=3 for each and the error bars represent the standard deviation.
Figure 9:
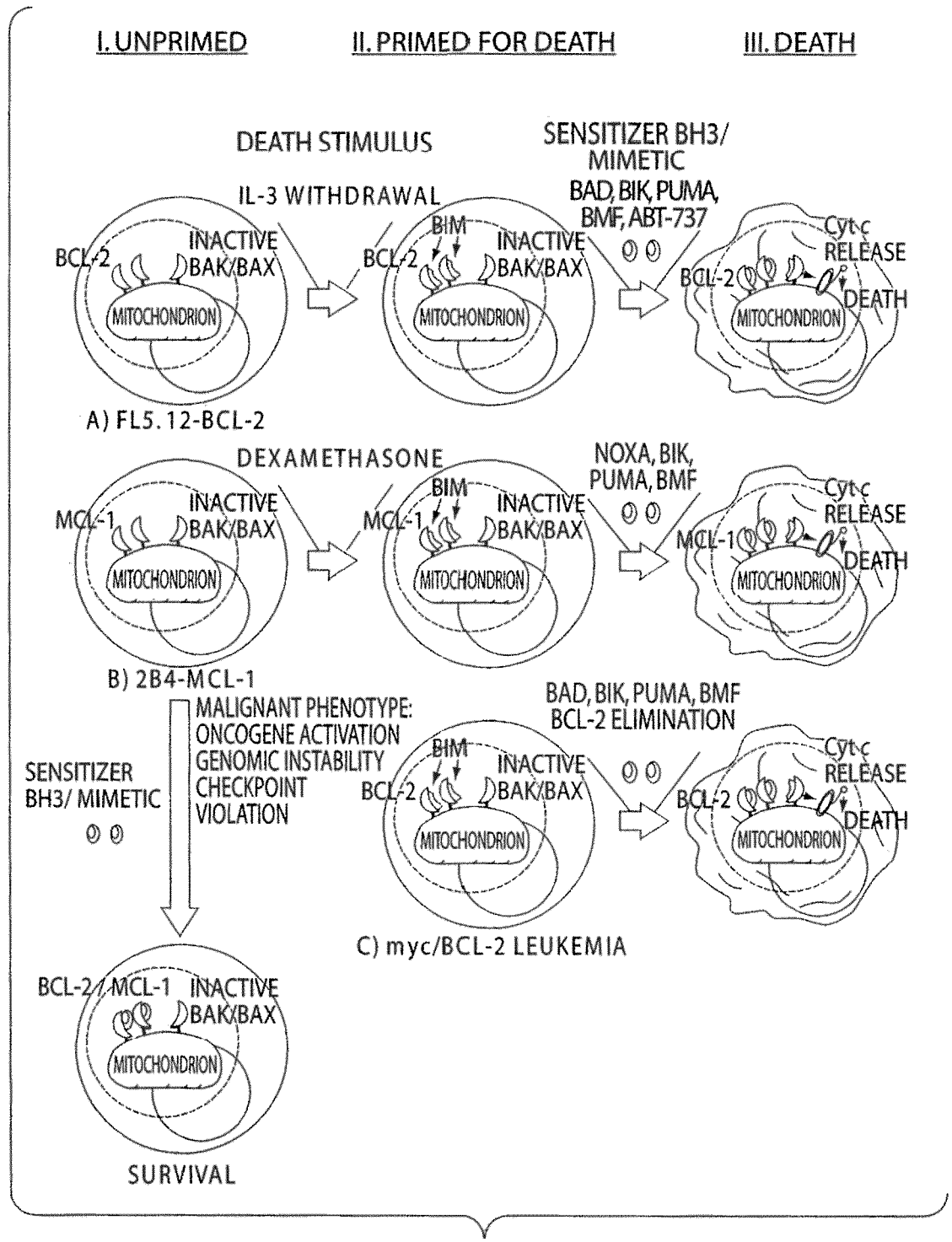
FIG. 9 is a model of selective cancer sensitivity to sensitizer BH3 mimetic treatment. Living unprimed cells (I) are primed for death following death stimuli (II). The leukemia cell is tonically primed for death without external intervention (II). Cells in the primed state undergo apoptosis in response to antiapoptotic antagonists (III)—those in the unprimed state do not. A) FL %.12-BCL-2. B) 2B4-MCL-1. C) myc/BCL-2 leukemia cells.
Figure 10:
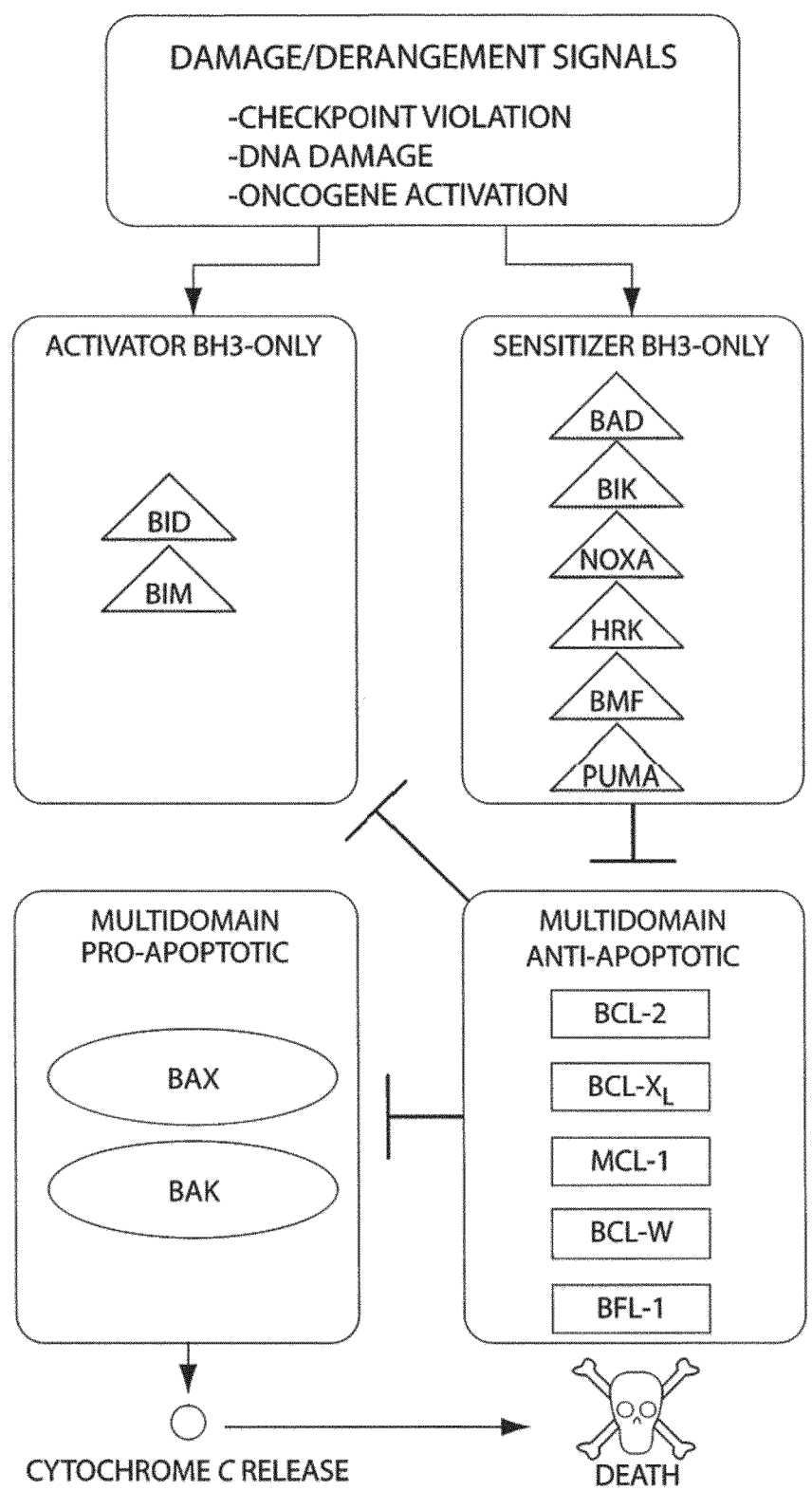
FIG. 10 is a diagram depicting a model of BCL-2 family control of programmed cell death. Death signals cause induction or post-translational activation of BH3-only proteins. Activator BH3-only proteins, including BID and BIM, induce oligomerization of BAX and/or BAK, causing MOMP, cytochrome c release and caspase activation resulting in cell death. Antiapoptotic proteins prevent apoptosis by sequestering activator BH3-only proteins and BAX/BAK, upstream of BAX/BAK oligomerization. Sensitizer BH3-only proteins promote cell death by binding the antiapoptotic proteins, displacing activator BH3-only proteins to trigger BAX/BAK oligomerization.

As another test of the ability of BH3 profiling to detect in vivo BCL-2 dependence, two small cell lung cancer (SCLC) cell lines were examined. Mitochondria were isolated from two SCLC cell lines, H146 and H1963 and exposed to panel of BH3 peptides. Cytochrome c release quantitated by ELISA. Both were sensitive to treatment with ABT-737 in vitro and in an in vivo murine xenograft model (Oltersdorf T, 2005). Both H146 and H1963 demonstrate a pattern of sensitivity diagnostic of BCL-2 sensitivity (FIG. 8D). This provides further support, in addition to the results of FIG. 4B and FIG. 7E, that mitochondrial BH3 profiling is a powerful predictor of what cells are sensitive to BH3 mimetic drugs in vitro and in vivo.

Example 9: ABT-737 Kills CLL Cells in the Low Nanomolar Range

Figure 12A:
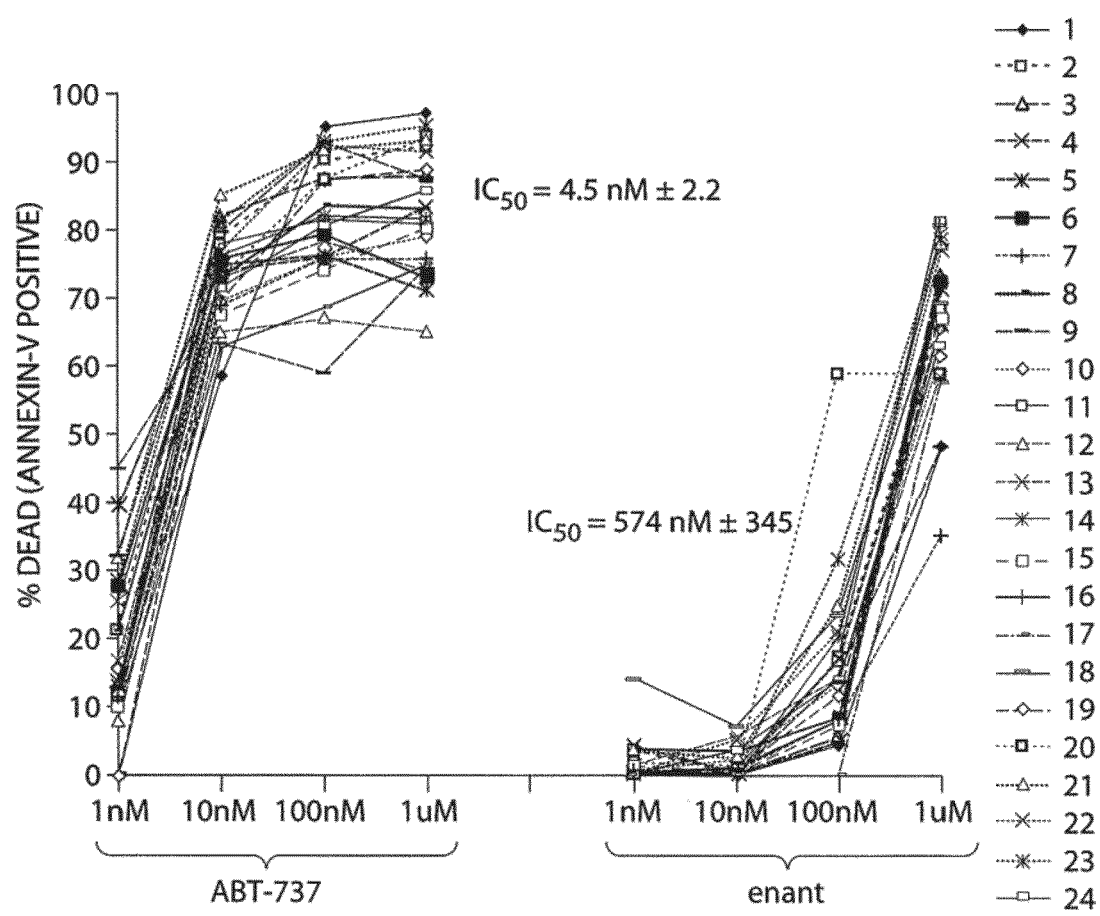
FIG. 12A is a line graph showing the effect of ABT-737 on CLL cell viability. CLL cells from 24 patient samples were cultured for 48 hours with different concentrations of compounds. Death was quantitated by Annexin-V staining and normalized to solvent (DMSO) treated controls.
Figure 12B:
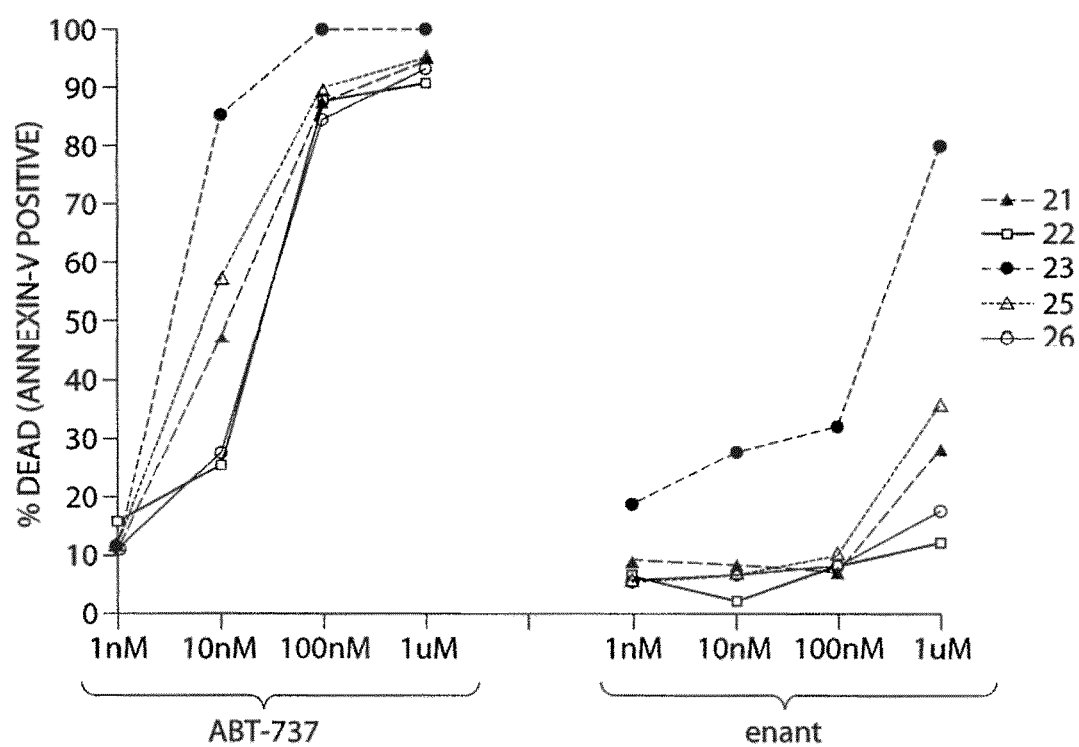
FIG. 12B is a line graph showing the effect of ABT-737 on CLL cell viability. CLL cells harvested from 5 patient samples were cultured for 4 hours with different concentrations of compounds. Death was quantitated as in FIG. 12A.
Figure 12C:
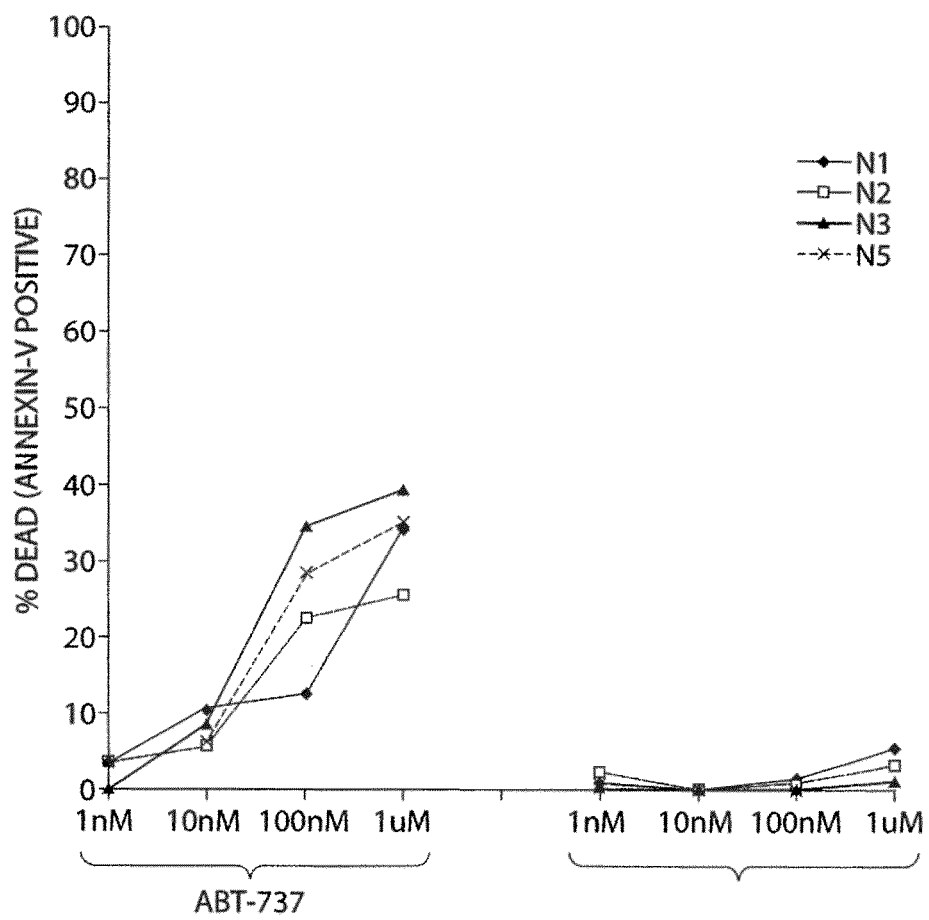
FIG. 12C is a line graph showing the effect of ABT-737 on normal PBMC viability. PBMC's were cultured for 24 hours in the presence of the indicated concentrations of compounds.

ABT-737 is a cell-permeant small molecule with affinity to BCL-2, BCL-XL, and BCL-w in the sub-nanomolar range. The negative control enantiomer (enant) is a stereoisomer of ABT-737 that binds to BCL-2 with lower affinity, and has been used as a loss of function control (Oltersdorf et al., 2005). CLL cells have shown sensitivity to ABT-737, so they were selected as a possible initial cancer model of BCL-2 dependence (Oltersdorf et al., 2005). Freshly isolated primary CLL cells were incubated with ABT-737 or negative control enantiomer. After 48 hours, death was assessed using Annexin-V staining. In all twenty-four CLL samples tested, apoptosis was induced within 48 hours by ABT-737 with an EC50 of 4.5+2.2 nM (FIG. 12A) (range 1.9-9.4 nM, see Table 3). The negative control enantiomer was less potent (mean EC50 574 nM) (FIG. 12A). Directly targeting the apoptotic machinery might be expected to induce apoptosis rapidly. Five samples treated for four hours responded similarly compared to 48-hour treatment (FIG. 12B). Non-malignant peripheral blood mononuclear cells (PBMC) from normal donors were resistant to ABT-737 with an EC50>1000 nM (FIG. 12C).

TABLE 3

| Patient | EC50 ABT-737 (nM) | EC50 NCE (nM) | Age | RaI Stage | WBC (×10E-3/ul) | CD38 | LDH (313-618) | beta-2 (0-2.7) | treatment History | IgVH Status |
|---|---|---|---|---|---|---|---|---|---|---|
| V1  | 7.0 | 1114 | 74 | 2 | 282   | nd  | 819  | 4.1 | untreated   | nd  |
| V2  | 3.2 | 473  | 75 | 1 | 72.5  | nd  | 337  | 3.7 | untreated   | mut |
| V3  | 3.5 | 622  | 63 | 3 | 89.4  | neg | 2138 | 2.5 | untreated   | un  |
| V4  | 3.6 | 496  | 57 | 1 | 164.6 | nd  | 563  | 5.6 | C; R        | mut |
| V5  | 2.1 | 619  | 62 | 2 | 61.2  | nd  | 431  | 5.3 | untreated   | mut |
| V6  | 3.1 | 493  | 65 | 2 | 126   | neg | 533  | 4.5 | F; F + Cy; R | mut |
| V7  | 1.9 | 1783 | 58 | 2 | 47.1  | nd  | 444  | 1.7 | untreated   | nd  |
| V8  | 4.1 | 500  | 43 | 2 | 216.4 | nd  | 398  | 3   | untreated   | mut |
| V9  | 8.7 | 1009 | 76 | 1 | 108.3 | nd  | 434  | 2.6 | untreated   | un  |
| V10 | 5.8 | 630  | 55 | 1 | 66.3  | pos | 613  | 3.2 | untreated   | un  |
| V11 | 3.1 | 334  | 57 | 1 | 85.3  | nd  | 501  | 1.9 | untreated   | nd  |
| V12 | 6.0 | 679  | 74 | 2 | 257.1 | nd  | 473  | 3.2 | untreated   | mut |
| V13 | 4.5 | 683  | 41 | 1 | 307.9 | pos | 1310 | 5.3 | untreated   | un  |
| V14 | 3.3 | 318  | 89 | 2 | 233.9 | neg | 463  | 1.8 | untreated   | mut |
| V15 | 6.4 | 582  | 63 | 3 | 201.8 | nd  | 431  | 3.2 | untreated   | un  |
| V16 | 2.9 | 343  | 60 | 1 | 72.2  | nd  | 444  | 1.9 | untreated   | mut |
| V17 | 9.4 | 861  | 47 | 3 | 244.1 | nd  | 424  | 2.6 | untreated   | mut |
| V18 | 2.3 | 317  | 46 | 1 | 89.9  | nd  | 450  | 2   | untreated   | mut |
| V19 | 6.4 | 572  | 55 | 1 | 162   | nd  | 156  | 2.7 | untreated   | mut |
| V20 | 4.8 | 119  | 66 | 3 | 502   | neg | 563  | 5.3 | S:C:F:R     | mut |
| V21 | 2.1 | 215  | 68 | 1 | 107.9 | nd  | 647  | 3.5 | untreated   | mut |
| V22 | 4.0 | 310  | 62 | 3 | 343   | nd  | 583  | 4.3 | untreated   | mut |
| V23 | 7.4 | 239  | 64 | 2 | 140.5 | nd  | 458  | 2.4 | untreated   | mut |
| V24 | 6.1 | 616  | 55 | 1 | 55    | pos | 503  | 2.6 | untreated   | mut | nd = not determined
C = chlorambucil
R = rituximab
F = fludarabine
Cy = cyclophosphamide
S = splenectomy

Example 10: BCL-2 and BIM Levels are Consistent Among CLL Samples

Figure 13A:
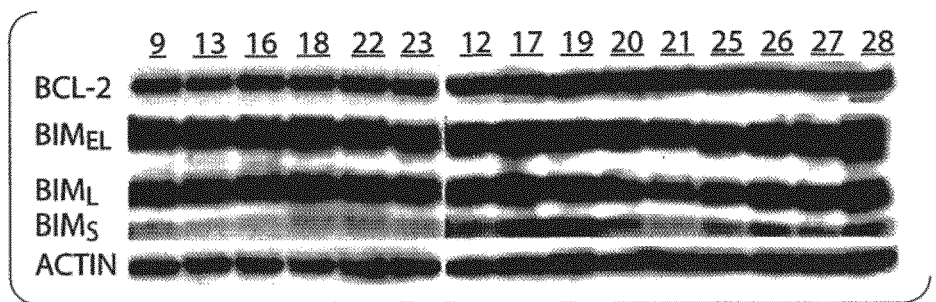
FIG. 13A is a photograph of an immunoblot showing BCL-2 and BIM protein levels in whole cell lysates from CLL samples (number corresponds to patient number in FIG. 12A). Three isoforms of BIM (BIM extra long-BIMEL, BIM long-BIML, and BIM short-BIMS) are shown.
Figure 13B:
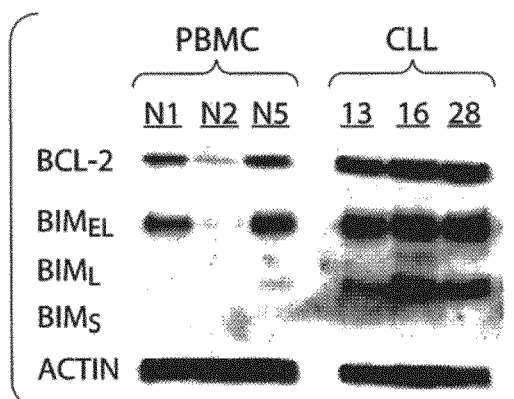
FIG. 13B is a photograph of an immunoblot showing BCL-2 and BIM protein levels in whole cell lysates from PBMC. Three normal PBMC lysates are at left, CLL lysates at right.
Figure 13C:
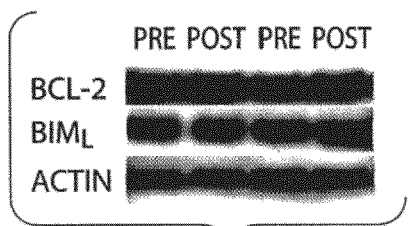
FIG. 13C is a photograph of an immunoblot showing BCL-2 and BIM protein levels in whole cell lysates from two independent CLL primary samples made at time of cell harvest (pre) and 48 hours post-culture (post).

Given the consistency of response to ABT-737, it was hypothesized that BCL-2 protein expression was also uniform in CLL cells. In addition, proapoptotic BIM has been shown to be an important determinant of commitment to apoptosis in lymphocytic cells (Bouillet et al., 1999; Opfennan et al., 2003). Antiapoptotic BCL-2 and proapoptotic BIM levels among 15 CLL samples were remarkably uniform (FIG. 13A); levels of BCL-2 and BIM in PBMC's were consistently lower (FIG. 13B). To ensure that short-term culture did not affect BCL-2 or BIM levels and perhaps alter response to ABT-737, protein lysates were made from CLL samples at time of isolation and after 48 hours in culture. Neither BCL-2 nor BIM levels changed during culture (FIG.

Figure 13D:
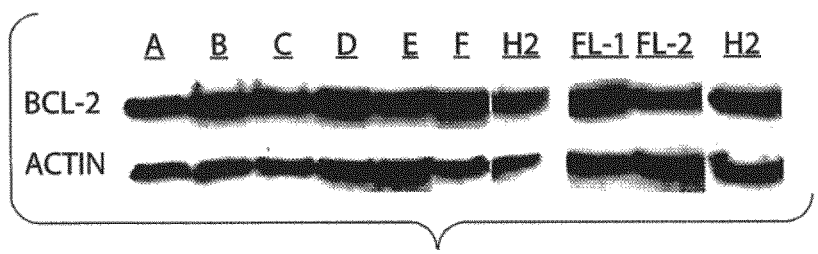
FIG. 13D is a photograph of an immunoblot showing BCL-2 protein levels in primary CLL cells (A-F) and primary follicular lymphoma cells (FL). The immunoblots are indexed to lysates from the t(14;18)-containing H2 human lymphoma cell line.

13C). BCL-2 levels in CLL cells were compared to levels in follicular lymphoma, a cancer in which BCL-2 is overexpressed due to the t(14;18) translocation (FIG. 13D). BCL-2 levels were notably similar in the two diseases.

Table 4 summarizes the clinical characteristics of the source patients in FIG. 12A. EC50 values were compared between groups dichotomized by factors previously identified as prognostically useful in CLL. This analysis revealed that in no case did a difference in mean EC50 between groups exceed 2 nM. A nonparametric statistical comparison of the groups showed that none differed with statistical significance except the groups dichotomized by leukocyte count (Table 5). Thus, biological response to ABT-737 appears to be largely independent of traditional prognostic factors.

TABLE 4

| | # | | Median | Range |
|---|---|---|---|---|
| Rai stage | | Age | 82.5 | 41-70 |
| 0 | 0 | years | | |
| 1-2 | 19 | Leukocyte count | 133.2 | 47-502 |
| 3-4 | 5 | at range 4.8-10.8 × | | |
| CD28 | | 1000/ul | | |
| positive | 3 | LDH | 487 | 185-2138 |
| negative | 4 | at range 813-648 ul | | |
| not assessed | 17 | S2 microglobulin | 3.1 | 1.7-5.5 |
| | | at range 0-2.7 mg/ml | | |
| Treatment history | | | | |
| prior treatment | 5 | | | |
| untreated | 21 | | | |
| IgvH status | | | | |
| mutated | 13 | | | |
| immolated | 5 | | | |
| not assessed | 3 | | | |
| ZAP79 | | | | |
| positive | 9 | | | |
| negative | 9 | | | |
| not assessed | 9 | | | |

TABLE 5

| parameter | dichotomy | p value | |
|---|---|---|---|
| CD38 | pos vs neg | 0.11 | |
| beta-2 | 0-27 vs >2.7 | 0.56 | |
| age | 0-55 vs >65 | 0.14 | |
| LDH | 0-618 vs >618 | 0.89 | |
| WBC | 0-133 vs >133 | 0.02 | Higher WBC correlates with higher EC50 |
| Rai stage | 0-2 vs 3-4 | 0.14 | |
| prior treatment | yes vs no | 0.93 | |
| IgVH mutated | pos vs neg | 0.10 | |
| ZAP70 | pos vs neg | 0.69 | |

Example 11: CLL Mitochondria Reveal a Tonic Dependence on BCL-2 Function to Maintain Outer Membrane Integrity Since BCL-2 opposes the intrinsic, or mitochondrial, pathway of apoptosis, it was hypothesized that the toxicity of ABT-737 was based on a mitochondrial requirement for BCL-2 function in CLL. A panel of peptides has been characterized, which derived from the BH3 domains of BH3-only proteins that behave as selective antagonists of BCL-2 function in several genetically defined model systems (Letai et al., 2002) (and MC, VDM, Nishino M, Wei G, Korsmeyer S, Annstrong S, AL, in preparation). For instance, BH3 peptides from BAD, PUMA, BMF, and, with lower potency, BIK bind and inhibit BCL-2 function, whereas BH3 domains from NOXA, HRK and BNIP-3A do not interact with BCL-2. This panel has been validated on other antiapoptotic family members, and this pattern of interaction is distinct for each antiapoptotic protein, so that the function of each may be specifically detected by this "BH3 profiling." Therefore, mitochondria that depend on BCL-2 function for maintenance of their outer membrane integrity show induction of outer membrane permeability when treated with BAD, PUMA and BMF, but not NOXA, HRK, and BNIP-3A peptides.

Figure 14:
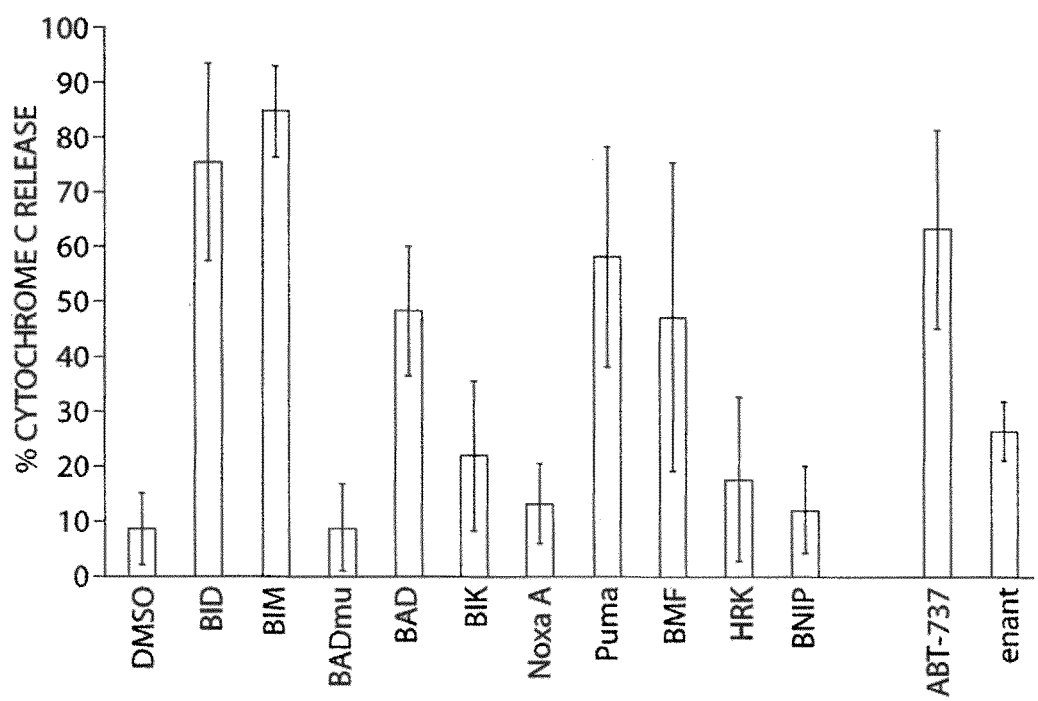
FIG. 14 is a bar chart showing the effects of BH3-only domain peptides (100 µM) or compounds (100 µM) on cytochrome c release (measured by ELISA) from mitochondria isolated from independent primary CLL patient samples. BADmu=a point mutant of the BAD BH3-only domain, used as a negative control. N=7, except for BADmu where N=5, ABT-737 and negative control enantiomer N=3. Error bars represent the standard deviation.

CLL mitochondria were incubated with BH3 peptides as well as ABT-737 and negative control enantiomer (FIG. 14). Note that activators BID and BIM BH3 peptides interact with all antiapoptotic proteins tested and furthermore can directly activate BAX and BAK (Letai, et al., 2002), so that they act as positive controls for cytochrome c release assays. BAD, PUMA and BMF induce cytochrome c release, whereas the NOXA, HRK, and BNIP-3A peptides, and a point null mutant of BAD BH3, do not. This pattern is diagnostic of mitochondrial BCL-2 dependence. ABT-737 also induced cytochrome c release, validating that its target is located at the mitochondria of CLL cells and required to maintain mitochondrial outer membrane integrity. Therefore, these "BH3 profiling" experiments demonstrate that the CLL mitochondria depend on BCL-2 function to maintain outer mitochondrial membrane integrity, elucidating a mechanism for the exquisite sensitivity of CLL cells to ABT-737 treatment. Since the BH3 peptides in the sensitizer panel lack the ability to directly activate BAX and BAK, these experiments also implicated the presence of an activator molecule constitutively sequestered by BCL-2 in CLL.

Example 12: BIM Bound to Bcl-2 Primes CLL Cells for Killing by Abt-737

Previously studies have shown that ABT-737 and the sensitizer BH3 peptides act as antagonists of antiapoptotic BCL-2, but lack the ability to directly activate BAX and BAK. In order to induce MOMP, sensitizers require the presence of an activator like BIM or BID (Letai et al., 2002; Oltersdorf et al., 2005). The results above, therefore, suggest an activator is bound to BCL-2, then displaced by ABT-737 or the BCL-2 binding BH3 peptides. Following displacement, it was hypothesized that the freed activator could induce MOMP via interaction with BAX and BAK.

Figure 15A:
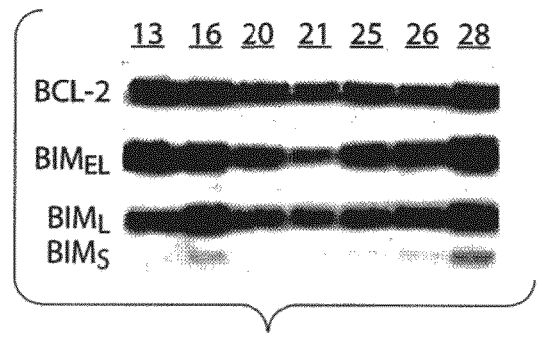
FIG. 15A is a photograph of an immunoblot of BCL-2 and BIM proteins in whole cell lysates of seven independent CLL samples.
Figure 15B:
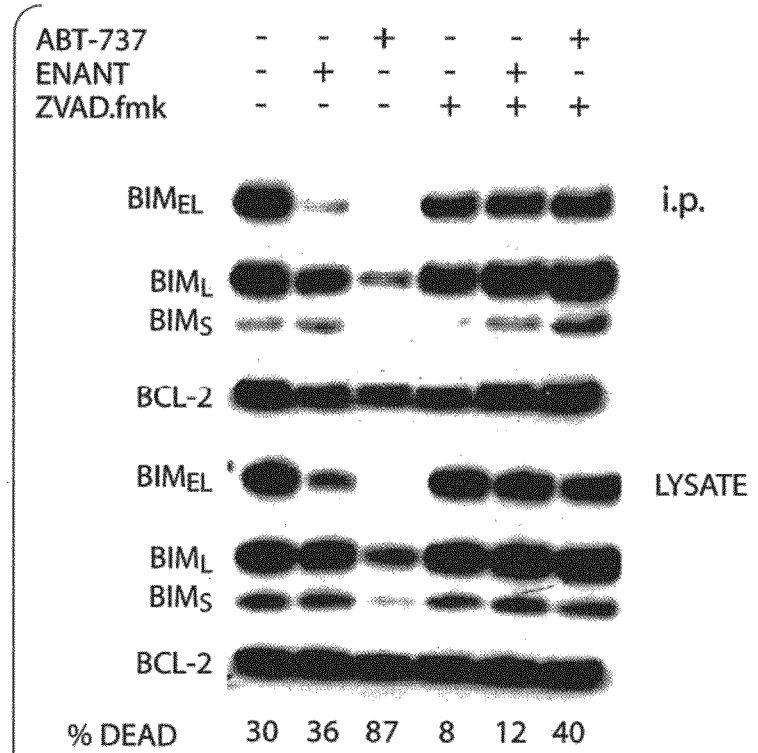
FIG. 15B is a photograph of an immunoblot of BCL-2 and BIM proteins in whole cell lysates of primary CLL cells. Primary CLL cells were cultured for 24 hours with 100 nM ABT-737, 100 nM negative control enantiomer, or vehicle (DMSO)+200 µM ZVAD.fmk. Death was then quantitated by Annexin-V staining. Immunoprecipitation (i.p.) using lysates from each treatment group was performed using an anti-BCL-2 antibody. Results shown are representative of three independent experiments.

FIG. 13 demonstrated the presence of BIM in CLL samples. Levels of BID, the other established activator BH3-only protein, were very faint by immunoblot, and cleaved, activated BID was almost to completely undetectable (not shown). It was hypothesized that BIM was indeed bound by BCL-2. FIG. 15A shows that BIM is sequestered by BCL-2 in primary CLL cells. Furthermore, treatment with ABT-737, and to a lesser degree, the less potent negative control enantiomer, causes a dramatic reduction in the amount of BIM bound to BCL-2 (FIG. 15B). Interestingly, displaced BIM seems to be rendered less stable, as total cellular levels of BIM, but not BCL-2, are reduced following ABT-737 treatment. Co-treatment with a pancaspase inhibitor ZVAD-fmk protects against ABT-737-induced death, further implicating an apoptotic death. ZVAD-fmk also preserves cellular BIM levels, suggesting that displaced BIM may be cleaved by caspases as previously reported (Chen and Zhou, 2004). Detergents in lysates can interfere with the binding of sensitizers to the BCL-2 hydrophobic cleft (not shown), so it was hypothesized that the observed persistence of BIM bound to BCL-2 after ABT-737 and ZVAD-fmk treatment might be an artifact due to detergent in the lysate inhibiting ABT-737's binding to BCL-2. Two competing hypotheses of ABT-737 mechanism of action were generated. In the first, ABT-737 displaces BIM from BCL-2, inducing BAX oligomerization and caspase activation, and finally caspase cleavage of the displaced BIM. In the second, BIM degradation is merely a consequence of MOMP and caspase activation that is initiated by a mechanism independent of BIM displacement.

Figure 15C:
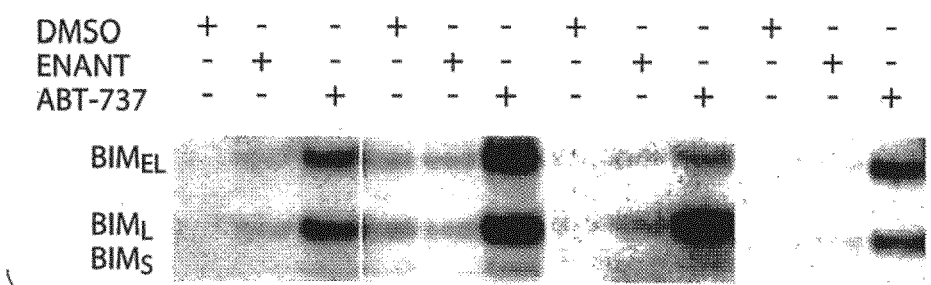
FIG. 15C is a photograph of an immunoblot. A BCL-2 antibody was used to immunoprecipitate BCL-2 from CLL lysates from four independent patient samples. After rinsing detergent away, the complex bound to the beads was then incubated with DMSO, 1 µM negative control enantiomer, or 1 μM ABT-737. Shown is the resulting immunoblot of the fraction displaced to the supernatant, probed for BIM.
Figure 15D:
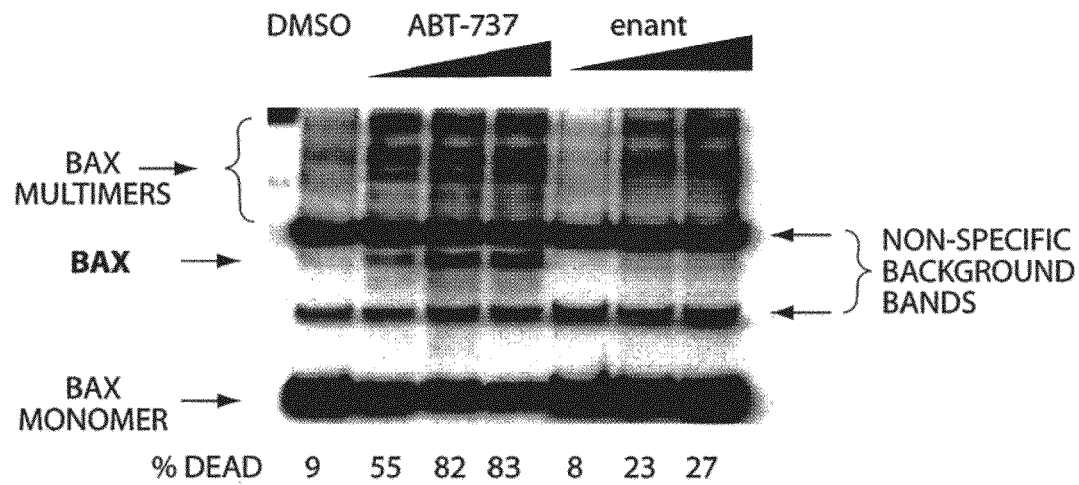
FIG. 15D is a photograph of an immunoblot. Freshly isolated CLL cells were incubated with DMSO, 10 nM, 100 nM, or 1 μM ABT-737 or negative control enantiomer for 4 hours. % dead was assessed by Annexin-V staining. Oligomerization of BAX was evaluated by anti-BAX immunoblot of chemically crosslinked whole cell lysates.

To test these competing hypotheses, whole cell lysates were examined for BCL-2:BIM complex levels in the presence or absence of ABT-737. In detergent-free conditions, ABT-737, but not the negative control enantiomer, displaces BIM from BCL-2 into the supernatant (FIG. 15C). BIM has been shown to activate BAX and induce its oligomerization (Letai et al., 2002; Marani, et al., 2002; Yamaguchi and Wang, 2002). Consistent with this mechanism, CLL cells display oligomerization of BAX within four hours of treatment with ABT-737 (FIG. 15D).

Figure 15E:
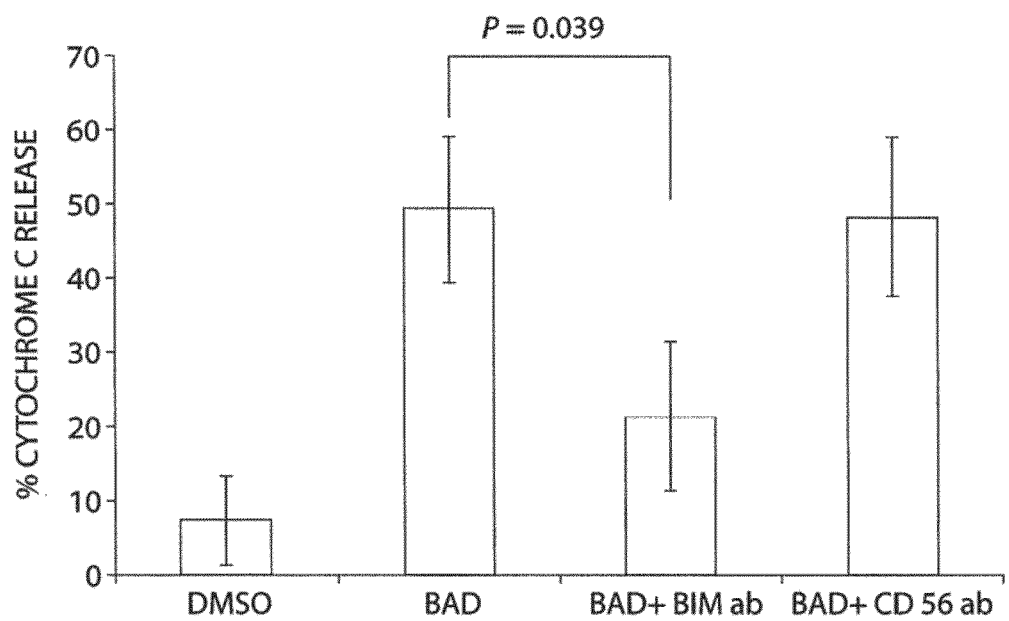
FIG. 15E is a bar chart showing the effect of 1% DMSO or 100 μM BAD BH3 peptide on mitochondria isolated from CLL samples. Samples were pre-incubated with antibodies directed against either the human BIM BH3 domain (Agent) or an irrelevant antigen (CD56) as indicated. N=5, bars show+standard deviation.
Figure 16A:
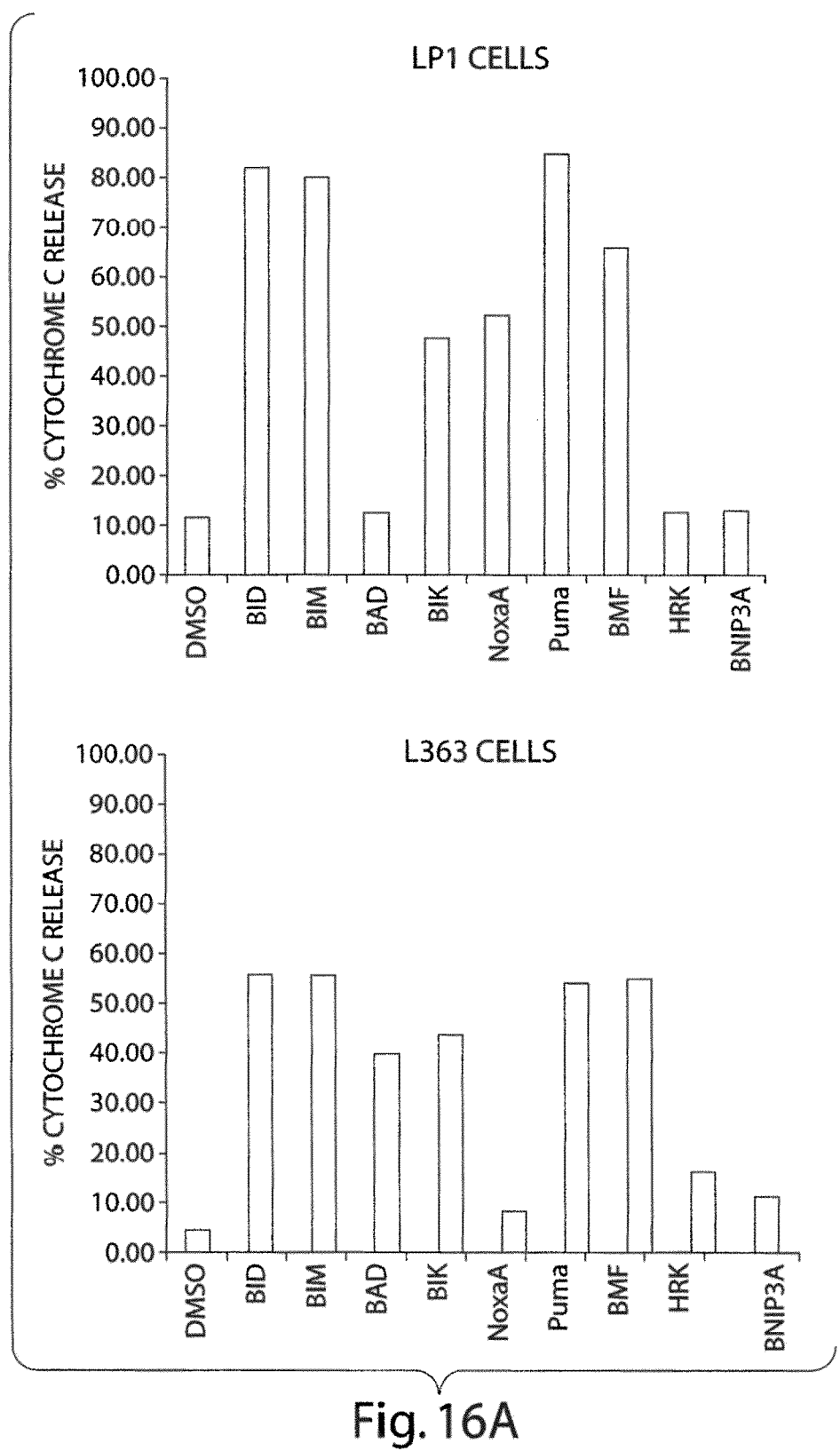
FIG. 16A is a bar chart showing the effect of 100 μM BH3 peptides on cytochrome c release from mitochondria isolated from LP1 cells.
Figure 16B:
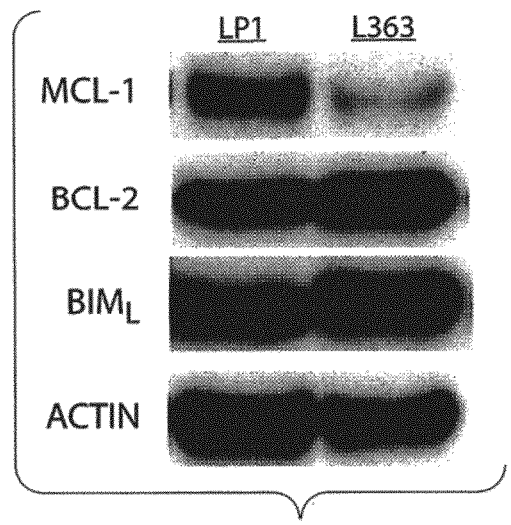
FIG. 16B is a photograph of an immunoblot of LP1 and L363 cell lines comparing levels of MCL-1, BCL-2, and BIM.
Figure 16C:
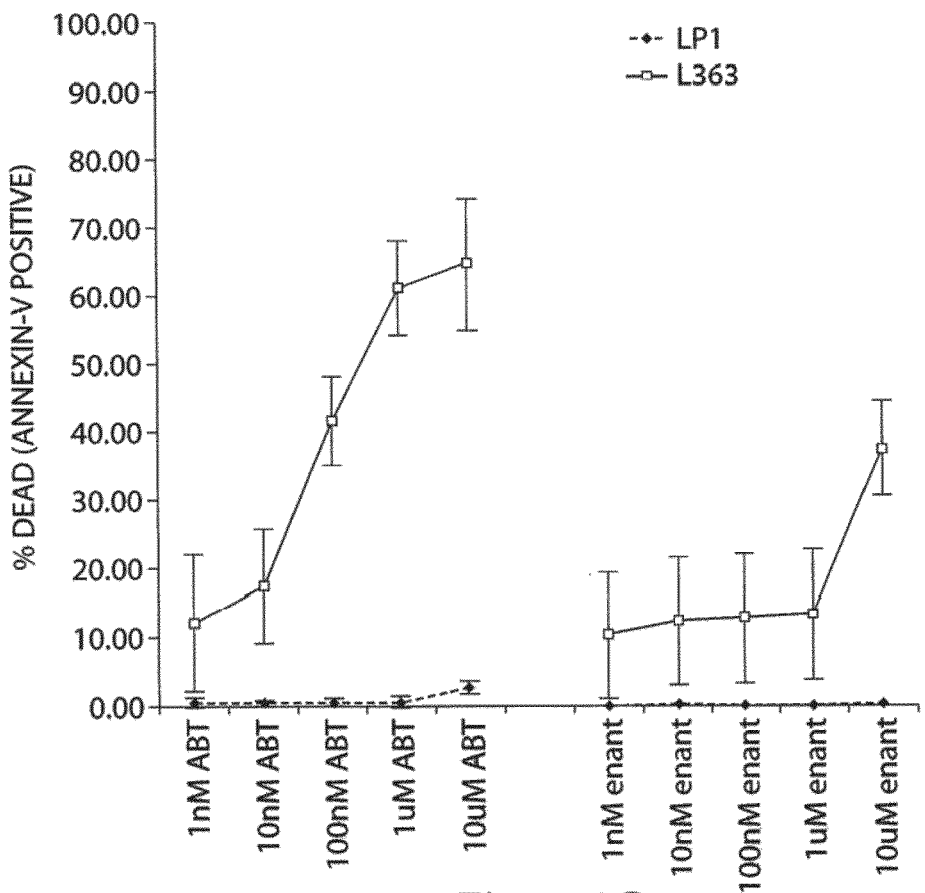
FIG. 16C is a line graph showing the effect of 48-hour treatment with ABT-737 on the viability of L363 cells and LP1 cells. N=3, bars show+standard deviation.
Figure 17:
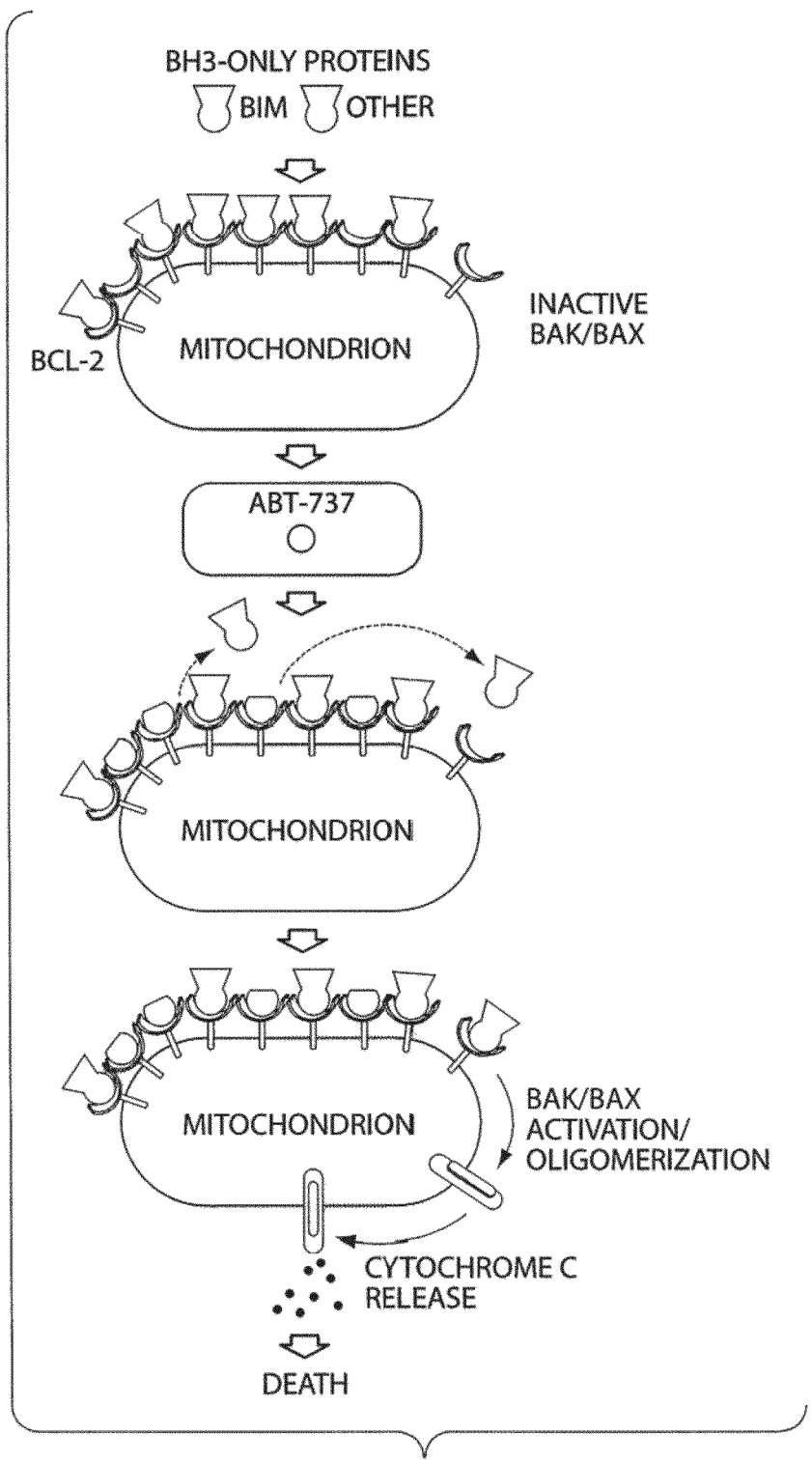
FIG. 17 is a diagram depicting a model of ABT-737 induced death at the mitochondria. Mitochondrial BCL-2 sequesters BIM in CLL cells. Upon addition of ABT-737, BIM is displaced and BCL-2 becomes occupied by ABT-737. Freed BIM then interacts with BAX or BAK, inducing oligomerization leading to cytochrome c release and irreversible commitment to programmed cell death. BCL-2 primed with activator BH3-only proteins renders the cancer cell sensitive to treatment with ABT-737 and possibly other chemotherapeutic agents.

If the first hypothesis is correct, and BIM is required for inducing the MOMP following BCL-2 antagonism, selective sequestration of BIM should cause a reduction in cytochrome c release following antagonism of BCL-2 on CLL mitochondria. In FIG. 15E, BCL-2 function is antagonized with the sensitizer BAD BH3 peptide. As shown in FIG. 12, BAD BH3 by itself induced cytochrome c release. However, addition of an antibody that binds the BH3 domain of BIM caused a dramatic reduction in cytochrome c release. An irrelevant antibody had no effect. Prevention of cytochrome c release by masking BIM supports the first hypothesis, that antagonism of ABT-737 is toxic to CLL cells due to the displacement of BIM (FIG. 15C) from a BCL-2:BIM complex. Displaced BIM then induces BAX oligomerization (FIG. 15D), MOMP and commitment to programmed cell death. An important implication of these results is that BCL-2 expression is necessary but not sufficient to dictate response to antagonism of BCL-2 by ABT-737 or sensitizer BH3 peptides. Activator BH3-only proteins like BIM must be sequestered by BCL-2 for the cell to be sensitive to BCL-2 antagonism.

Example 14: Predication of Drug Response by BH3 Profiling

Figure 18B:
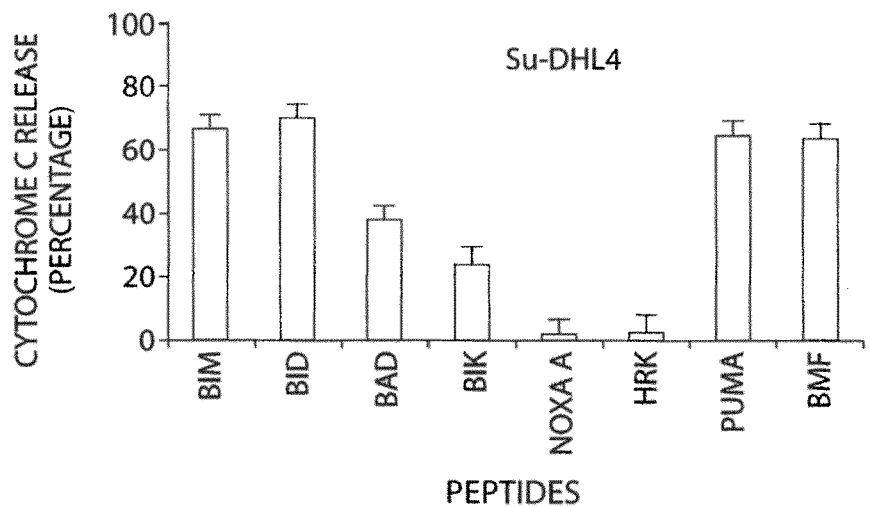
FIGS. 18B-18E are a series of bar charts showing BH3 profiles for various lymphoma cell lines.
Figure 18C:
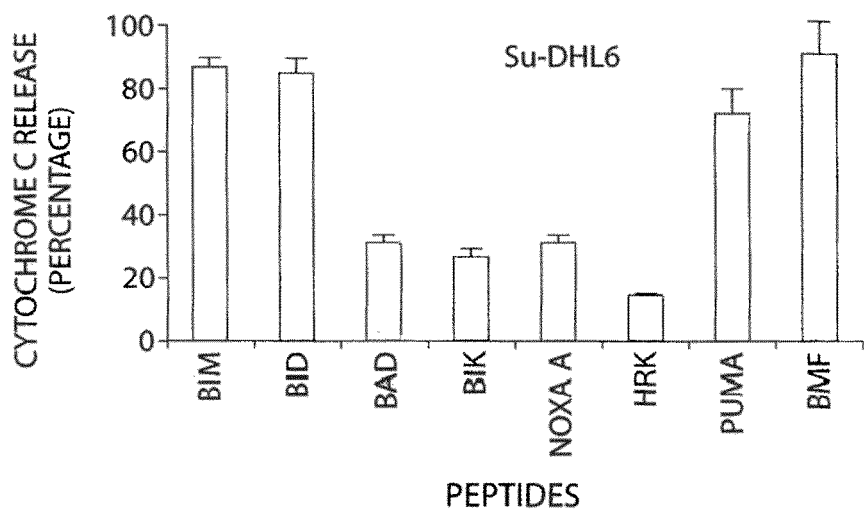
Figure 18D:
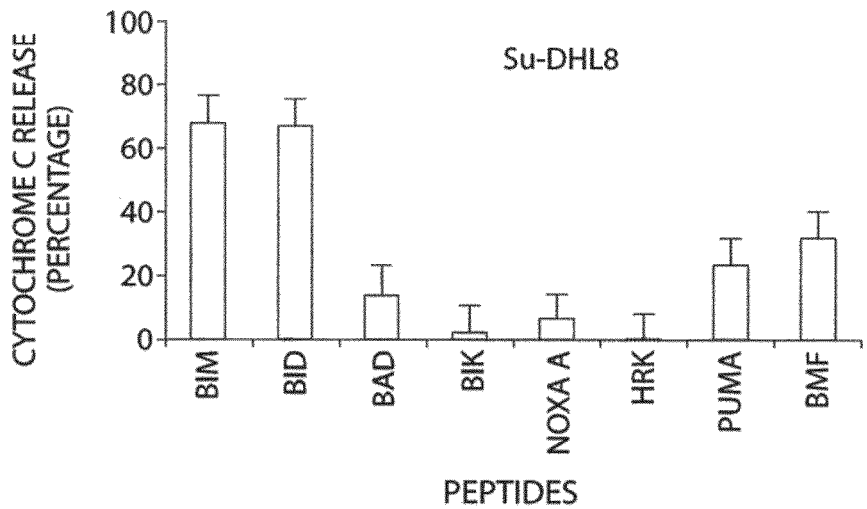
Figure 18E:
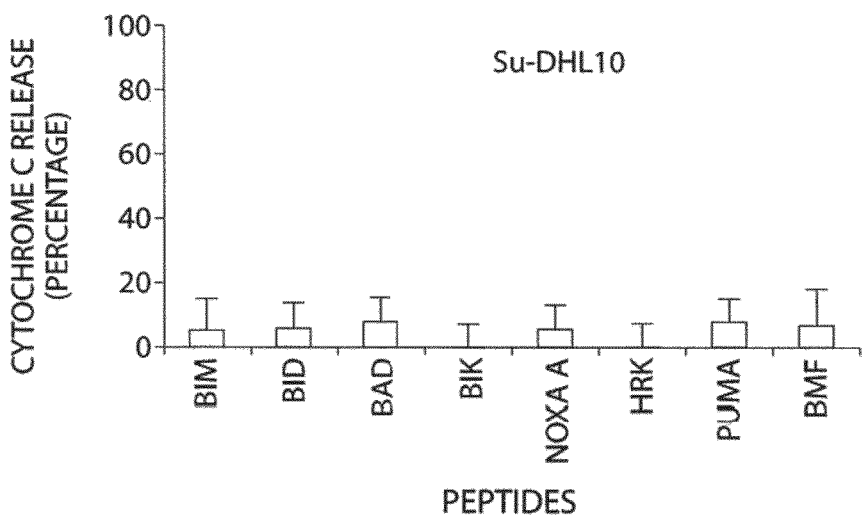

BH3 profiling allows for the prediction of response of cancer cells to anti-cancer therapeutics. For the purposes of this application, therapeutics can be divided into those that target anti-apoptotic BCL-2 proteins, and conventional agents. As a model test system, four lymphoma cell lines SU-DHL4, SU-DHL6, SU-DHL8, and SU-DHL 10 were employed. To perform BH3 profiling, the ability of a panel of sensitizer peptides to induce mitochondrial outer membrane permeabilization (MOMP) in mitochondria isolated from the lymphoma cells were tested. For easy reference, FIG. 18A shows the interaction pattern between the BH3 peptides and anti-apoptotic proteins. MOMP was measured by quantifying cytochrome c release by ELISA.

As shown in FIG. 18B-E, BH3 profiling proved able to distinguish these three classes of blocks in our sample of four lymphoma lines. SU-DHL4 and SU-DHL6 a "primed" phenotype, based on the sensitivity to sensitizer BH3 peptides. Note that a strong response to the PUMA BH3 peptide, which interacts with all of the antiapoptotic proteins, provides a useful gauge of whether the mitochondria are primed. The pattern of sensitivity (PUMA, BMF, BAD, +/−BIK) indicated a dependence on BCL-2 for SU-DHL-4. SU-DHL 6 also was primed, as shown by a strong PUMA BH3 and BMF BH3 signal. The weaker, but definite, response to both of the more selective BH3 peptides BAD BH3 and NOXA A BH3 implicate combined dependence on BCL-2 and MCL-1. SU-DHL-8 appeared to be poorly primed, given the limited response to PUMA BH3 and other sensitizers, but nonetheless demonstrated an intact effector arm by responding strongly to activators BIM BH3 and BID BH3. SU-DHL-10 responded poorly to both sensitizer and activator peptides, indicating the loss of the effector arm.

Figure 19A:
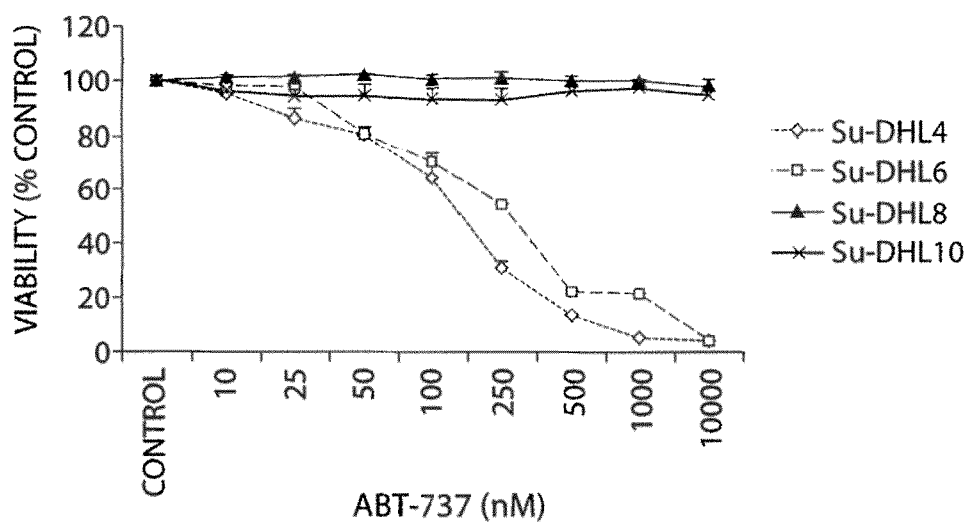
FIGS. 19A-19B are a series of line graphs showing cell sensitivity to various agents
Figure 19B:
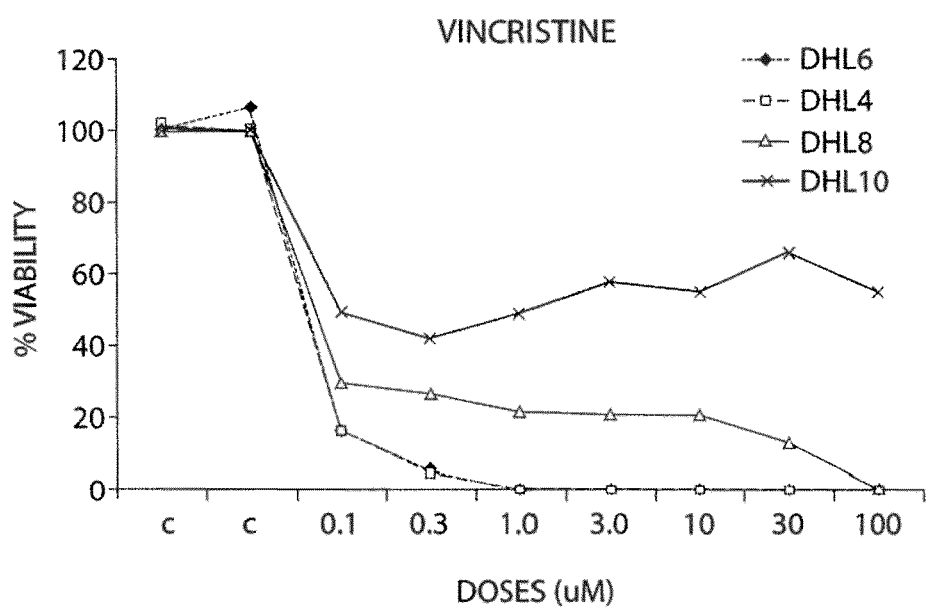
Figure 20A:
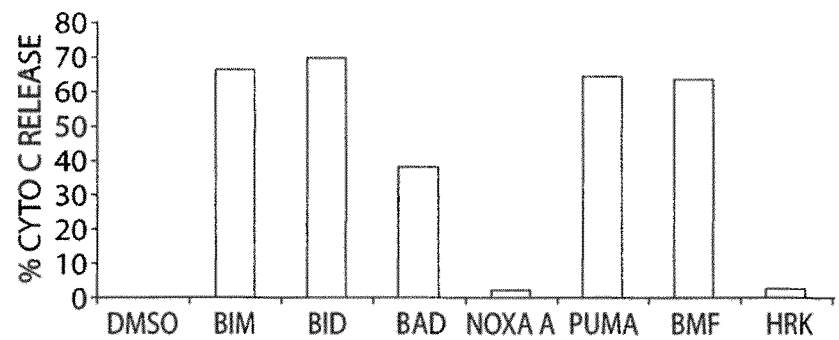
FIGS. 20A-20D are a series of bar charts showing a comparison of mitochondrial and cell-based BH3 profiling.
Figure 20B:
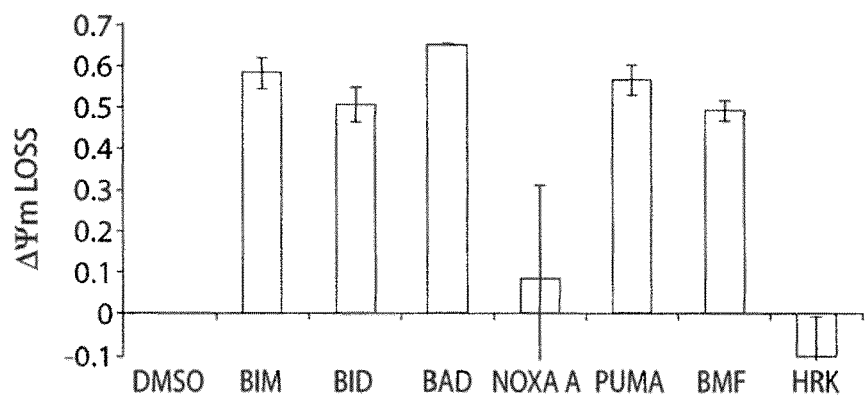
Figure 20C:
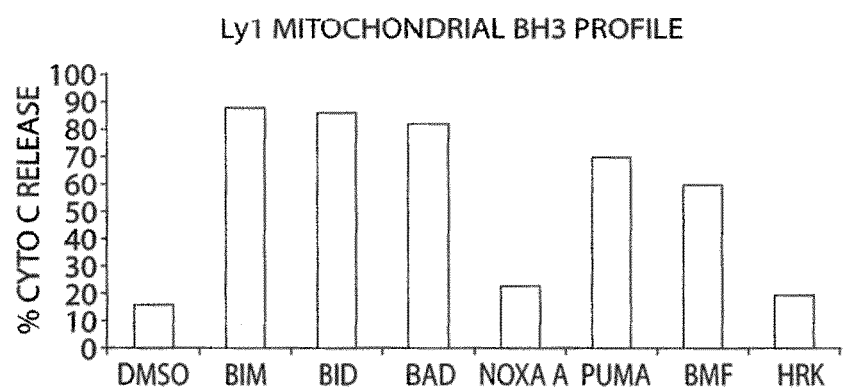
Figure 20D:
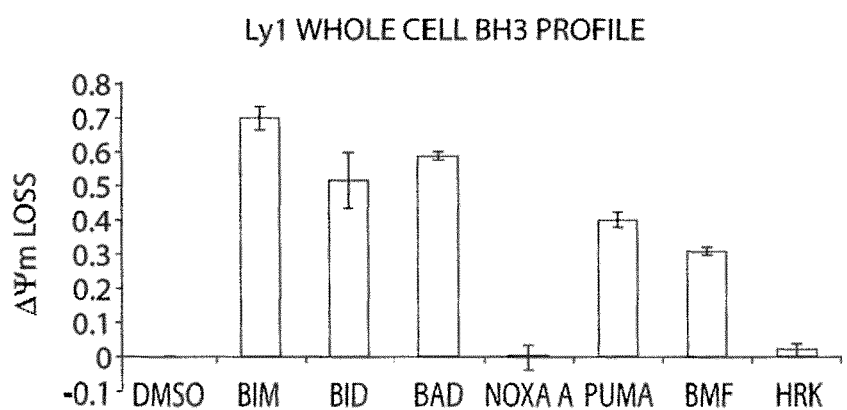

Only cells that are dependent on BCL-2 for survival are predicted to respond to BCL-2 antagonists like ABT-737. Therefore, BH3 profiling predicts that SU-DHL4 and SU-DHL6 should respond to ABT-737. This hypothesis was tested and confirmed that BH3 profiling accurately predicted response to ABT-737 (FIG. 19A). Furthermore, BH3 profiling would predict that SU-DHL4 and SU-DHL6 might be more sensitive to other chemotherapy agents, as they are "primed" for death and SU-DHL-8 and SU-DHL-10 were not. To test this, cells were treated with vincristine. As predicted by BH3 profiling SU-DHL4 and SU-DHL6 were the most sensitive cell lines (FIG. 19B).

Example 15: Cell Based BH3 Profiling

A method that converts the mitochondrial-based BH3 profiling to a cell-based assay was developed. In this assay, cells are permeabilized by digitonin to permit peptide access to mitochondria. Cells are treated with the fluorescent dye JC-1 to evaluate loss of mitochondrial transmembrane electrochemical potential due to treatment with the peptides. Loss of mitochondrial integrity due to apoptosis can be observed by a shift in the fluorescence peak from 590 nm to 520 nm. Multiple assays may be read in parallel on a 96- or 384-well plate in the TECAN Safire2 fluorimeter. To test this system, it has been applied it to several cell lines of known BCL-2 dependence, and have obtained excellent correlation between results of mitochondrial BH3 profiling and cellular BH3 profiling. Two examples may be seen in FIGS. 20A-20D.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining whether a chemotherapeutic agent will induce cell death in cancer cells of a cancer cell sample, the method comprising:
   contacting a cancer cell of the cancer cell sample with a BH3 domain peptide, wherein the cancer cell is a primary human cancer cell; and
   detecting BH3 domain peptide-induced mitochondrial outer membrane permeabilization of said cancer cell,
   wherein the method is performed in the absence of contacting the cancer cell with the chemotherapeutic agent and wherein the presence of BH3 domain peptide-induced mitochondrial outer membrane permeabilization indicates treatment comprising the chemotherapeutic agent will induce cell death in cancer cells of the cancer cell sample, wherein said treatment comprising the chemotherapeutic agent does not comprise treatment with a BH3 domain mimetic or an antagonist of antiapoptotic BCL-2 family members.

2. A method of determining whether a chemotherapeutic agent will induce cell death in cancer cells of a cancer cell sample, the method comprising:
   contacting mitochondria from a cancer cell of the cancer cell sample with a BH3 domain peptide or mimetic thereof, wherein the cancer cell is a primary human cancer cell; and
   detecting cytochrome c release from said mitochondria, wherein the method is performed in the absence of contacting the cancer cell with the chemotherapeutic agent and wherein the cytochrome c release indicates treatment comprising the chemotherapeutic agent will induce cell death in cancer cells of the cancer cell sample, wherein said treatment comprising the chemotherapeutic agent does not comprise treatment with a BH3 domain mimetic or an antagonist of antiapoptotic BCL-2 family members.

3. The method of claim 1, wherein said cancer cell is permeabilized prior to contacting with said BH3 domain peptide.

4. The method of claim 3, further comprising contacting said permeabilized cell with a potentiometric dye.

5. The method of claim 4, where said potentiometric dye is JC-1 or dihydrorhodamine 123.

6. The method of claim 4, where said BH3 domain peptide-induced mitochondrial outer membrane permeabilization is measured by detecting a change in emission of said potentiometric dye.

7. The method of claim 1, wherein said BH3 domain peptide is derived from the BH3 domain of a BID, a BIM, a BAD, a BIK, a NOXA, a PUMA, a BMF, or a HRK polypeptide.

8. The method of claim 1, wherein said BH3 domain peptide comprises an amino acid sequence selected from the group consisting of SEQ ID NO: 1-14 and 15.

9. The method of claim 1, wherein said cancer cell is a lymphoma cell, a leukemia cell, or a small cell lung cancer cell.

10. The method of claim 1, wherein said BH3 domain peptide is derived from the BH3 domain of a NOXA polypeptide, and wherein the presence of BH3 domain peptide-induced mitochondrial outer membrane permeabilization indicates said cancer cell is an MCL-1-dependent cancer cell.

11. The method of claim 1, wherein the BH3 domain peptide is less than or equal to 50 amino acids in length, less than or equal to 35 amino acids in length, less than or equal to 25 amino acids in length, or less than or equal to 15 amino acids in length.

12. The method of claim 8, wherein the amino acid sequence comprises at least one of a tryptophan substitution or a tyrosine substitution at one or more amino acid positions.

* * * * *